(12) United States Patent
Basson et al.

(10) Patent No.: US 11,452,764 B2
(45) Date of Patent: Sep. 27, 2022

(54) INHIBITING FAK-AKT INTERACTION TO INHIBIT METASTASIS

(71) Applicants: Board of Trustees of Michigan State University, East Lansing, MI (US); University of North Dakota, Grand Forks, ND (US)

(72) Inventors: Marc D. Basson, Grand Forks, ND (US); Leslie A. Kuhn, East Lansing, MI (US); Sebastian Raschka, Madison, WI (US)

(73) Assignees: University of North Dakota, Grand Forks, ND (US); Board of Trustees of Michigan State University, East Lansing, MI (US)

( * ) Notice: Subject to any disclaimer, the term of this patent is extended or adjusted under 35 U.S.C. 154(b) by 88 days.

(21) Appl. No.: 16/632,748

(22) PCT Filed: Jul. 19, 2018

(86) PCT No.: PCT/US2018/042919
§ 371 (c)(1),
(2) Date: Jan. 21, 2020

(87) PCT Pub. No.: WO2019/018666
PCT Pub. Date: Jan. 24, 2019

(65) Prior Publication Data
US 2020/0164046 A1 May 28, 2020

Related U.S. Application Data

(60) Provisional application No. 62/678,561, filed on May 31, 2018, provisional application No. 62/535,490, filed on Jul. 21, 2017.

(51) Int. Cl.
*A61K 38/45* (2006.01)
*A61P 35/00* (2006.01)
*A61K 31/24* (2006.01)
*C07C 251/68* (2006.01)
*G01N 33/573* (2006.01)

(52) U.S. Cl.
CPC .............. *A61K 38/45* (2013.01); *A61K 31/24* (2013.01); *A61P 35/00* (2018.01); *C07C 251/68* (2013.01); *C12Y 207/10002* (2013.01); *G01N 33/573* (2013.01)

(58) Field of Classification Search
None
See application file for complete search history.

(56) References Cited

U.S. PATENT DOCUMENTS

2020/0121620 A1* 4/2020 Gil .................. A61K 31/03
2020/0330471 A1* 10/2020 Pachter ............ C07D 401/12

FOREIGN PATENT DOCUMENTS

WO WO-2013040142 A2 3/2013
WO WO-2019018666 A1 1/2019

OTHER PUBLICATIONS

"International Application Serial No. PCT/US2018/042919, International Search Report dated Nov. 19, 2018", 9 pgs.
"International Application Serial No. PCT/US2018/042919, Invitation to Pay Add'l Fees and Partial Search Report dated Sep. 26, 2018", 16 pgs.
"International Application Serial No. PCT/US2018/042919, Written Opinion dated Nov. 19, 2018", 12 pgs.
Basson, M. D., "The c-terminal region of the focal adhesion kinase f1 domain binds Akt1 and inhibits pressure-induced cell adhesion", J Physiol Pharmacol., 68(3), (Jun. 1, 2017), 375-383.
Zeng, Bixi, et al., "Inhibition of pressure-activated cancer cell adhesion by FAK-derived peptides", Oncotarget, 8(58), (2017), 98051-98067.
"International Application Serial No. PCT/US2018/042919, International Preliminary Report on Patentability dated Jan. 30, 2020", 14 pgs.

* cited by examiner

*Primary Examiner* — Ralph J Gitomer
(74) *Attorney, Agent, or Firm* — Schwegman Lundberg & Woessner, P.A.

(57) ABSTRACT

Methods and compositions are described herein that inhibit FAK/ATK interactions. Such methods and compositions are useful for inhibiting cell adhesion and cancer metastasis.

11 Claims, 49 Drawing Sheets

Specification includes a Sequence Listing.

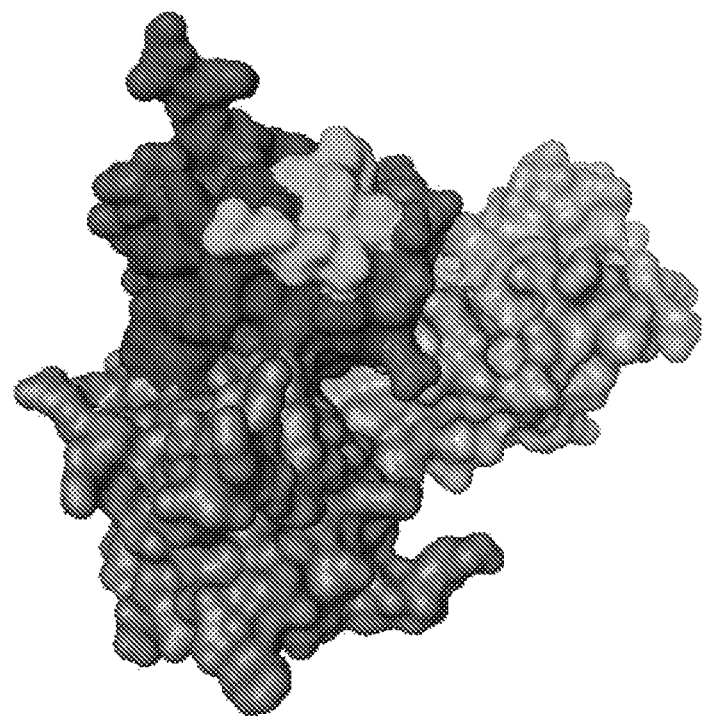
FIG. 5B
FIG. 5A

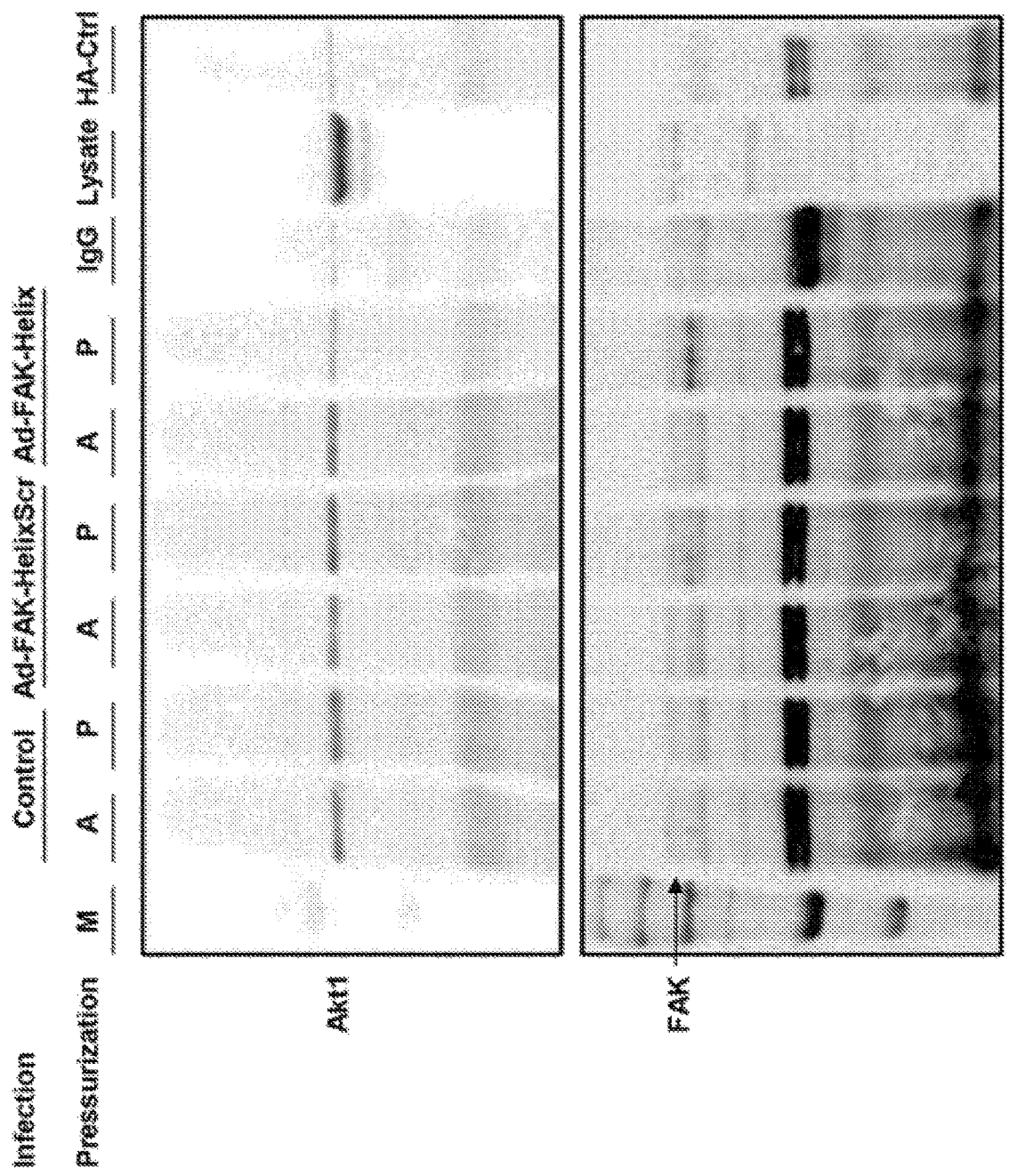

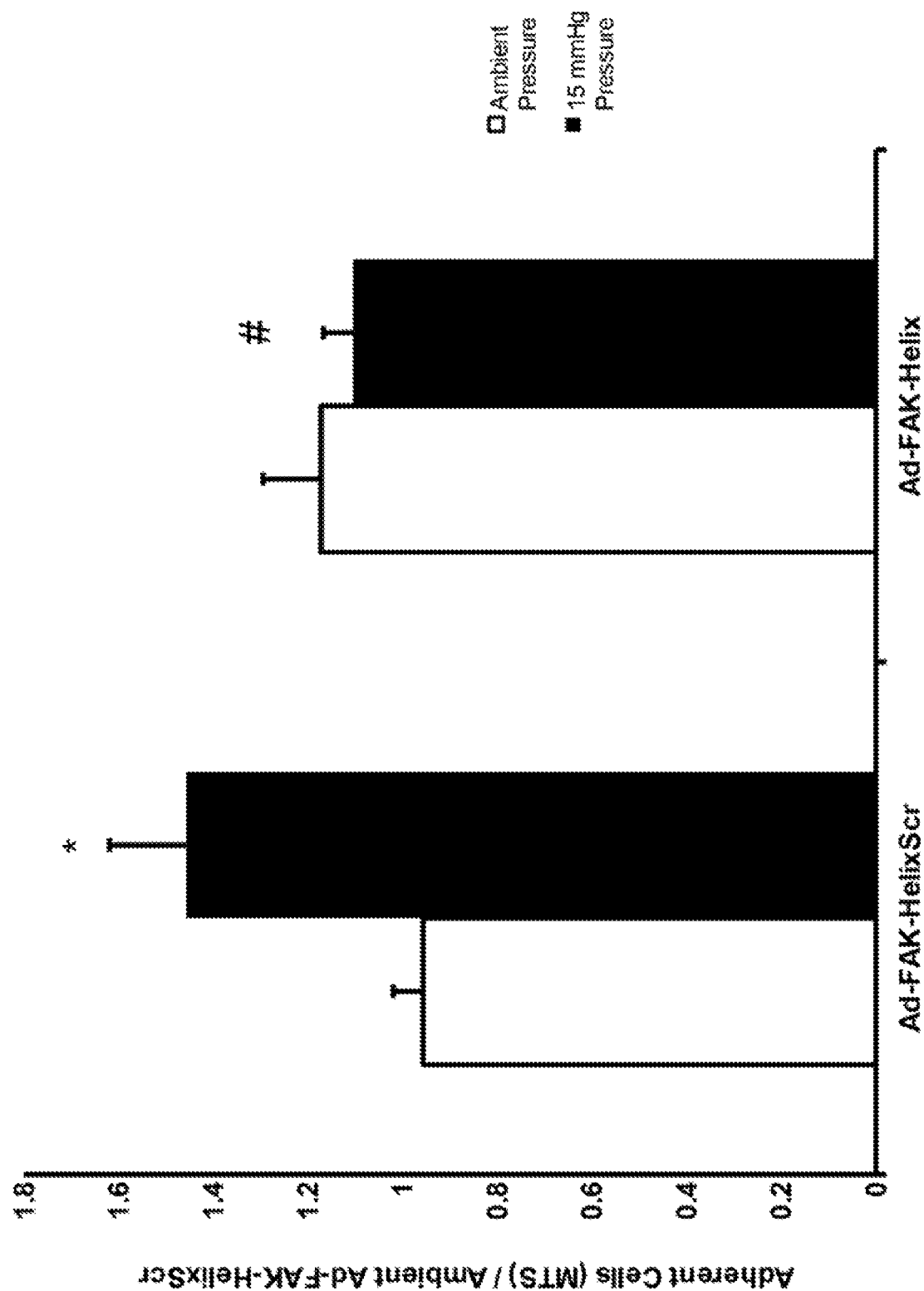

ZINC ID: 04085549
CAS ID: 383147-88-4
*1-(2-{[(2-methylbenzoyl)oxy]imino}-cyclohexyl)-2,4-dinitrobenzene*

ZINC04085549

1-(2-{[(2-methylbenzoyl)oxy]imino}-cyclohexyl)-2,4-dinitrobenzene

ZINC02457454

N-[1-(cyclopentylcarbamoyl)cyclohexyl]-N-(2-thienylmethyl)benzo[1,3]dioxole-5-carboxamide

ZINC04085550*

1-{2-[(benzoyloxy)imino]cyclohexyl}-2,4-dinitrobenzene

ZINC12960430*

N-[2-(2,4-dinitrophenyl)cyclohexyliden]-N-[(phenylsulfonyl)oxy]amine

ZINC4085554**

1-(2-{[(4-methoxybenzoyl)oxy]imino}cyclohexyl)-2,4-dinitrobenzene

ZINC6241139**

1-(3-{[(anilinocarbonyl)oxy]imino}cyclohexyl)-2,4-dinitrobenzene

ZINC5816335\*\*

1-(2-{[(cyclopentylcarbonyl)oxy]imino}
cyclohexyl)-2,4-dinitrobenzene

ZINC31501681

*N-[(1S)-3-oxo-1-phenyl-3-[(2S)-2-([1,2,4]triazolo[4,3-a]pyridin-3-yl)pyrrolidin-1-yl]propyl]benzamid*

ZINC58264388

*[(1S)-3-[(2S)-2-(o-tolyl)pyrrolidin-1-yl]-3-oxo-1-(2-thienyl)propyl]urea*

ZINC40099027

(2S)-2-(4-methoxyphenyl)-N-[2-morpholino-5-(trifluoromethyl)phenyl]pyrrolidine-1-carboxamide

ZINC25613745

[(1S)-1-(2-chlorophenyl)-3-[(2S)-2-(3,4-dimethoxyphenyl)pyrrolidin-1-yl]-3-oxo-propyl]urea

SEQUENCE LISTING

<160> NUMBER OF SEQ ID NOS: 47

<210> SEQ ID NO 1
<211> LENGTH: 7
<212> TYPE: PRT
<213> ORGANISM: Homo sapiens

<400> SEQUENCE: 1

Leu Ala His Pro Pro Glu Glu
1               5

```
<210> SEQ ID NO 2
<211> LENGTH: 33
<212> TYPE: PRT
<213> ORGANISM: Homo sapiens

<400> SEQUENCE: 2

Glu Val His Trp Val His Leu Asp Met Gly Val Ser Ser Val Arg Glu
1               5                   10                  15

Lys Tyr Glu Leu Ala His Pro Pro Glu Glu Trp Lys Tyr Glu Leu Arg
            20                  25                  30

Ile

<210> SEQ ID NO 3
<211> LENGTH: 126
<212> TYPE: PRT
<213> ORGANISM: Homo sapiens

<400> SEQUENCE: 3

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
50                  55                  60

Arg Gly Ile Ile Gln Lys Ile Val Asp Ser His Lys Val Lys Asn Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Pro Pro Glu Glu Trp Lys Tyr Glu Leu Arg Ile
        115                 120                 125

<210> SEQ ID NO 4
<211> LENGTH: 510
<212> TYPE: PRT
<213> ORGANISM: Homo sapiens

<400> SEQUENCE: 4

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Pro Pro Glu Glu Trp Lys Tyr Glu Leu Arg Ile Arg Tyr
        115                 120                 125
```

Leu Pro Lys Gly Phe Leu Asn Gln Phe Thr Glu Asp Lys Pro Thr Leu
130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
            165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
            195                 200                 205

Lys Ser Leu Leu Asp Ser Val Lys Ala Lys Thr Leu Arg Lys Leu Ile
210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
                260                 265                 270

Ala Ile Gly Pro Glu Glu Gly Ile Ser Tyr Leu Thr Asp Lys Gly Cys
                275                 280                 285

Asn Pro Thr His Leu Ala Asp Phe Thr Gln Val Gln Thr Ile Gln Tyr
290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
                340                 345                 350

Gly Thr Ser Gln Ser Phe Ile Ile Arg Pro Gln Lys Glu Gly Glu Arg
                355                 360                 365

Ala Leu Pro Ser Ile Pro Lys Leu Ala Asn Ser Glu Lys Gln Gly Met
370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415

Ser Lys Ser Tyr Gly Ile Asp Glu Ala Arg Asp Tyr Glu Ile Gln Arg
                420                 425                 430

Glu Arg Ile Glu Leu Gly Arg Cys Ile Gly Glu Gly Gln Phe Gly Asp
                435                 440                 445

Val His Gln Gly Ile Tyr Met Ser Pro Glu Asn Pro Ala Leu Ala Val
                450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
                485                 490                 495

Cys Phe Ala His His Ser Ile Leu Ser Val Leu His Ser Thr
                500                 505                 510

<210> SEQ ID NO 5
<211> LENGTH: 1884
<212> TYPE: DNA
<213> ORGANISM: Homo sapiens

<400> SEQUENCE: 5

```
gcgcacgcgc gcgggcccgc gccgacgcag cacggcctcg agggcgcgag cccgcgccgc      60
cgccgccgcc gccggtcccg gaccactgtg agcccgcggc gtgaggcgtg ggaggaagcg     120
cggctgctgt cgcccagcgc cgccccgtcg tcgtctgcct tcgcttcacg gcgccgagcc     180
gcggtccgaa atatgacaga tacctagcat ctagcaaaat aatggcagct gcttaccttg     240
accccaactt gaatcacaca ccaaattcga gtactaagac tcacctgggt actggtatgg     300
aacgttctcc tggtgcaatg gagcgagtat taaaggtctt tcattatttt gaaagcaata     360
gtgagccaac cacctgggcc agtattatca ggcatggaga tgctactgat gtcaggggca     420
tcattcagaa gatagtggac agtcacaaag taaagcatgt ggcctgctat ggattccgcc     480
tcagtcacct gcggtcagag gaggttcact ggcttcacgt ggatatgggc gtctccagtg     540
tgagggagaa gtatgagctt gctcacccac cagaggagtg gaaatatgaa ttgagaattc     600
gttatttgcc aaaaggattt ctaaaccagt ttactgaaga taagccaact ttgaatttct     660
tctatcaaca ggtgaagagc gattatatgt tagagatagc tgatcaagtg gaccaggaaa     720
ttgctttgaa gttgggttgt ctagaaatac ggcgatcata ctgggagatg cggggcaatg     780
cactagaaaa gaagtctaac tatgaagtat tagaaaaaga tgttggttta aagcgatttt     840
ttcctaagag tttactggat tctgtcaagg ccaaaacact aagaaaactg atccaacaaa     900
catttagaca atttgccaac cttaatagag aagaaagtat tctgaaattc tttgagatcc     960
tgtctccagt ctacagattt gataaggaat gcttcaagtg tgctcttggt tcaagctgga    1020
ttatttcagt ggaactggca atcggcccag aagaaggaat cagttaccta acggacaagg    1080
gctgcaatcc cacacatctt gctgacttca ctcaagtgca aaccattcag tattcaaaca    1140
gtgaagacaa ggacagaaaa ggaatgctac aactaaaaat agcaggtgca cccgagcctc    1200
tgacagtgac ggcaccatcc ctaaccattg cggagaatat ggctgaccta atagatgggt    1260
actgccggct ggtgaatgga acctcgcagt catttatcat cagacctcag aaagaaggtg    1320
aacgggcttt gccatcaata ccaaagttgg ccaacagcga aaagcaaggc atgcggacac    1380
acgccgtctc tgtgtcagat gaaattagtg gggacgaaac agatgattat gctgagatta    1440
tagatgaaga agatacttac accatgccct caaaaagcta tggaatagat gaagccaggg    1500
attatgagat tcaaagagaa agaatagaac ttggacgatg tattggagaa ggccaatttg    1560
gagatgtaca tcaaggcatt tatatgagtc cagagaatcc agctttggcg gttgcaatta    1620
aaacatgtaa aaactgtact tcggacagcg tgagagagaa atttcttcaa gaagcctgcc    1680
ttaagctccc tggggataag gaccatgttt gtttcgctca ccactccata ctcagtgtcc    1740
tgcacagtac ttgacaccta gaaacacct ggtagatgtt tgtcattctg gtgtccttca    1800
ttatatgtgc atcaaatgaa tgccttctgt tttccattgt aataaatacc acccaacagt    1860
ccaataaatt aataattcat agag                                           1884
```

<210> SEQ ID NO 6
<211> LENGTH: 1074
<212> TYPE: PRT
<213> ORGANISM: Homo sapiens

<400> SEQUENCE: 6

```
Met Ile Ser Ala Asp Cys Asn Leu Cys Leu Pro Glu Tyr Asp Arg Tyr
1               5                   10                  15

Leu Ala Ser Ser Lys Ile Met Ala Ala Ala Tyr Leu Asp Pro Asn Leu
            20                  25                  30
```

```
Asn His Thr Pro Asn Ser Ser Thr Lys Thr His Leu Gly Thr Gly Met
            35                  40                  45

Glu Arg Ser Pro Gly Ala Met Glu Arg Val Leu Lys Val Phe His Tyr
 50                  55                  60

Phe Glu Ser Asn Ser Glu Pro Thr Thr Trp Ala Ser Ile Ile Arg His
 65                  70                  75                  80

Gly Asp Ala Thr Asp Val Arg Gly Ile Ile Gln Lys Ile Val Asp Ser
                 85                  90                  95

His Lys Val Lys His Val Ala Cys Tyr Gly Phe Arg Leu Ser His Leu
            100                 105                 110

Arg Ser Glu Glu Val His Trp Leu His Val Asp Met Gly Val Ser Ser
            115                 120                 125

Val Arg Glu Lys Tyr Glu Leu Ala His Pro Pro Glu Glu Trp Lys Tyr
130                 135                 140

Glu Leu Arg Ile Arg Tyr Leu Pro Lys Gly Phe Leu Asn Gln Phe Thr
145                 150                 155                 160

Glu Asp Lys Pro Thr Leu Asn Phe Phe Tyr Gln Gln Val Lys Ser Asp
                165                 170                 175

Tyr Met Leu Glu Ile Ala Asp Gln Val Asp Gln Glu Ile Ala Leu Lys
            180                 185                 190

Leu Gly Cys Leu Glu Ile Arg Arg Ser Tyr Trp Glu Met Arg Gly Asn
            195                 200                 205

Ala Leu Glu Lys Lys Ser Asn Tyr Glu Val Leu Glu Lys Asp Val Gly
            210                 215                 220

Leu Lys Arg Phe Phe Pro Lys Ser Leu Leu Asp Ser Val Lys Ala Lys
225                 230                 235                 240

Thr Leu Arg Lys Leu Ile Gln Gln Thr Phe Arg Gln Phe Ala Asn Leu
                245                 250                 255

Asn Arg Glu Glu Ser Ile Leu Lys Phe Phe Glu Ile Leu Ser Pro Val
            260                 265                 270

Tyr Arg Phe Asp Lys Glu Cys Phe Lys Cys Ala Leu Gly Ser Ser Trp
            275                 280                 285

Ile Ile Ser Val Glu Leu Ala Ile Gly Pro Glu Glu Gly Ile Ser Tyr
            290                 295                 300

Leu Thr Asp Lys Gly Cys Asn Pro Thr His Leu Ala Asp Phe Thr Gln
305                 310                 315                 320

Val Gln Thr Ile Gln Tyr Ser Asn Ser Glu Asp Lys Asp Arg Lys Gly
                325                 330                 335

Met Leu Gln Leu Lys Ile Ala Gly Ala Pro Glu Pro Leu Thr Val Thr
            340                 345                 350

Ala Pro Ser Leu Thr Ile Ala Glu Asn Met Ala Asp Leu Ile Asp Gly
            355                 360                 365

Tyr Cys Arg Leu Val Asn Gly Thr Ser Gln Ser Phe Ile Ile Arg Pro
            370                 375                 380

Gln Lys Glu Gly Glu Arg Ala Leu Pro Ser Ile Pro Lys Leu Ala Asn
385                 390                 395                 400

Ser Glu Lys Gln Gly Met Arg Thr His Ala Val Ser Val Ser Glu Thr
                405                 410                 415

Asp Asp Tyr Ala Glu Ile Ile Asp Glu Glu Asp Thr Tyr Thr Met Pro
            420                 425                 430

Ser Thr Arg Asp Tyr Glu Ile Gln Arg Glu Arg Ile Glu Leu Gly Arg
            435                 440                 445
```

-continued

```
Cys Ile Gly Glu Gly Gln Phe Gly Asp Val His Gln Gly Ile Tyr Met
            450                 455                 460
Ser Pro Glu Asn Pro Ala Leu Ala Val Ala Ile Lys Thr Cys Lys Asn
465                 470                 475                 480
Cys Thr Ser Asp Ser Val Arg Glu Lys Phe Leu Gln Glu Ala Leu Thr
                485                 490                 495
Met Arg Gln Phe Asp His Pro His Ile Val Lys Leu Ile Gly Val Ile
            500                 505                 510
Thr Glu Asn Pro Val Trp Ile Ile Met Glu Leu Cys Thr Leu Gly Glu
            515                 520                 525
Leu Arg Ser Phe Leu Gln Val Arg Lys Tyr Ser Leu Asp Leu Ala Ser
530                 535                 540
Leu Ile Leu Tyr Ala Tyr Gln Leu Ser Thr Ala Leu Ala Tyr Leu Glu
545                 550                 555                 560
Ser Lys Arg Phe Val His Arg Asp Ile Ala Ala Arg Asn Val Leu Val
                565                 570                 575
Ser Ser Asn Asp Cys Val Lys Leu Gly Asp Phe Gly Leu Ser Arg Tyr
            580                 585                 590
Met Glu Asp Ser Thr Tyr Tyr Lys Ala Ser Lys Gly Lys Leu Pro Ile
            595                 600                 605
Lys Trp Met Ala Pro Glu Ser Ile Asn Phe Arg Arg Phe Thr Ser Ala
            610                 615                 620
Ser Asp Val Trp Met Phe Gly Val Cys Met Trp Glu Ile Leu Met His
625                 630                 635                 640
Gly Val Lys Pro Phe Gln Gly Val Lys Asn Asn Asp Val Ile Gly Arg
                645                 650                 655
Ile Glu Asn Gly Glu Arg Leu Pro Met Pro Pro Asn Cys Pro Pro Thr
            660                 665                 670
Leu Tyr Ser Leu Met Thr Lys Cys Trp Ala Tyr Asp Pro Ser Arg Arg
            675                 680                 685
Pro Arg Phe Thr Glu Leu Lys Ala Gln Leu Ser Thr Ile Leu Glu Glu
690                 695                 700
Glu Lys Ala Gln Gln Glu Glu Arg Met Arg Met Glu Ser Arg Arg Gln
705                 710                 715                 720
Ala Thr Val Ser Trp Asp Ser Gly Gly Ser Asp Glu Ala Pro Pro Lys
                725                 730                 735
Pro Ser Arg Pro Gly Tyr Pro Ser Pro Arg Ser Ser Glu Gly Phe Tyr
            740                 745                 750
Pro Ser Pro Gln His Met Val Gln Thr Asn His Tyr Gln Val Ser Gly
            755                 760                 765
Tyr Pro Gly Ser His Gly Ile Thr Ala Met Ala Gly Ser Ile Tyr Pro
            770                 775                 780
Gly Gln Ala Ser Leu Leu Asp Gln Thr Asp Ser Trp Asn His Arg Pro
785                 790                 795                 800
Gln Glu Ile Ala Met Trp Gln Pro Asn Val Glu Asp Ser Thr Val Leu
                805                 810                 815
Asp Leu Arg Gly Ile Gly Gln Val Leu Pro Thr His Leu Met Glu Glu
            820                 825                 830
Arg Leu Ile Arg Gln Gln Gln Glu Met Glu Glu Asp Gln Arg Trp Leu
            835                 840                 845
Glu Lys Glu Glu Arg Phe Leu Lys Pro Asp Val Arg Leu Ser Arg Gly
850                 855                 860
```

```
Ser Ile Asp Arg Glu Asp Gly Ser Leu Gln Gly Pro Ile Gly Asn Gln
865                 870                 875                 880

His Ile Tyr Gln Pro Val Gly Lys Pro Asp Pro Ala Ala Pro Pro Lys
                885                 890                 895

Lys Pro Pro Arg Pro Gly Ala Pro Gly His Leu Gly Ser Leu Ala Ser
            900                 905                 910

Leu Ser Ser Pro Ala Asp Ser Tyr Asn Glu Gly Val Lys Leu Gln Pro
        915                 920                 925

Gln Glu Ile Ser Pro Pro Thr Ala Asn Leu Asp Arg Ser Asn Asp
    930                 935                 940

Lys Val Tyr Glu Asn Val Thr Gly Leu Val Lys Ala Val Ile Glu Met
945                 950                 955                 960

Ser Ser Lys Ile Gln Pro Ala Pro Pro Glu Glu Tyr Val Pro Met Val
                965                 970                 975

Lys Glu Val Gly Leu Ala Leu Arg Thr Leu Leu Ala Thr Val Asp Glu
            980                 985                 990

Thr Ile Pro Leu Leu Pro Ala Ser Thr His Arg Glu Ile Glu Met Ala
        995                 1000                1005

Gln Lys Leu Leu Asn Ser Asp Leu Gly Glu Leu Ile Asn Lys Met Lys
    1010                1015                1020

Leu Ala Gln Gln Tyr Val Met Thr Ser Leu Gln Gln Glu Tyr Lys Lys
1025                1030                1035                1040

Gln Met Leu Thr Ala Ala His Ala Leu Ala Val Asp Ala Lys Asn Leu
                1045                1050                1055

Leu Asp Val Ile Asp Gln Ala Arg Leu Lys Met Leu Gly Gln Thr Arg
            1060                1065                1070

Pro His

<210> SEQ ID NO 7
<211> LENGTH: 28
<212> TYPE: PRT
<213> ORGANISM: Homo sapiens

<400> SEQUENCE: 7

His Val Asp Met Gly Val Ser Ser Val Arg Glu Lys Tyr Glu Leu Ala
1               5                   10                  15

His Pro Pro Glu Glu Trp Lys Tyr Glu Leu Arg Ile
            20                  25

<210> SEQ ID NO 8
<211> LENGTH: 4550
<212> TYPE: DNA
<213> ORGANISM: Homo sapiens

<400> SEQUENCE: 8
gcgcacgcgc gcgggcccgc gccgacgcag cacggcctcg agggcgcgag cccgcgccgc    60
cgccgccgcc gccggtcccg gaccactgtg agcccgcggc gtgaggcgtg ggaggaagcg   120
cggctgctgt cgcccagcgc cgccccgtcg tcgtctgcct tcgcttcacg gcgccgagcc   180
gcggtccgaa gtcttgctgt gtcacccagg ctgccaggct ggagtggagt ggcatgatct   240
cggctgactg caacctctgc ctcccagaat atgacagata cctagcatct agcaaaataa   300
tggcagctgc ttaccttgac cccaacttga atcacacacc aaattcgagt actaagactc   360
acctgggtac tggtatggaa cgttctcctg gtgcaatgga gcgagtatta aggtctcttc   420 attatttga aagcaatagt gagccaacca cctgggccag tattatcagg catggagatg   480
```

```
ctactgatgt cagggggcatc attcagaaga tagtggacag tcacaaagta aagcatgtgg    540
cctgctatgg attccgcctc agtcacctgc ggtcagagga ggttcactgg cttcacgtgg    600
atatgggcgt ctccagtgtg agggagaagt atgagcttgc tcacccacca gaggagtgga    660
aatatgaatt gagaattcgt tatttgccaa aaggatttct aaaccagttt actgaagata    720
agccaacttt gaatttcttc tatcaacagg tgaagagcga ttatatgtta gagatagctg    780
atcaagtgga ccaggaaatt gctttgaagt tgggttgtct agaaatacgg cgatcatact    840
gggagatgcg gggcaatgca ctagaaaaga agtctaacta tgaagtatta gaaaaagatg    900
ttggtttaaa gcgattttt cctaagagtt tactggattc tgtcaaggcc aaaacactaa    960
gaaaactgat ccaacaaaca tttagacaat tgccaaccct aatagagaa gaaagtattc    1020 tgaaattctt tgagatcctg tctccagtct acagatttga taaggaatgc ttcaagtgtg    1080
ctcttggttc aagctggatt atttcagtgg aactggcaat cggcccagaa gaaggaatca    1140
gttacctaac ggacaagggc tgcaatccca cacatcttgc tgacttcact caagtgcaaa    1200
ccattcagta ttcaaacagt gaagacaagg acagaaaagg aatgctacaa ctaaaaatag    1260
caggtgcacc cgagcctctg acagtgacgg caccatccct aaccattgcg gagaatatgg    1320
ctgacctaat agatgggtac tgccggctgg tgaatgaac ctcgcagtca tttatcatca    1380
gacctcagaa agaaggtgaa cgggcttttgc catcaatacc aaagttggcc aacagcgaaa    1440
agcaaggcat gcggacacac gccgtctctg tgtcagaaac agatgattat gctgagatta    1500
tagatgaaga agatacttac accatgccct caaccaggga ttatgagatt caaagagaaa    1560
gaatagaact tggacgatgt attggagaag gccaatttgg agatgtacat caaggcattt    1620
atatgagtcc agagaatcca gctttggcgg ttgcaattaa aacatgtaaa aactgtactt    1680
cggacagcgt gagagagaaa tttcttcaag aagccttaac aatgcgtcag tttgaccatc    1740
ctcatattgt gaagctgatt ggagtcatca cagagaatcc tgtctggata atcatggagc    1800
tgtgcacact tggagagctg aggtcatttt tgcaagtaag gaaatacagt ttggatctag    1860
catctttgat cctgtatgcc tatcagctta gtacagctct tgcatatcta gagagcaaaa    1920
gatttgtaca cagggacatt gctgctcgga atgttctggt gtcctcaaat gattgtgtaa    1980
aattaggaga ctttggatta tcccgatata tggaagatag tacttactac aaagcttcca    2040
aaggaaaatt gcctattaaa tggatggctc cagagtcaat caattttcga cgttttacct    2100
cagctagtga cgtatggatg tttggtgtgt gtatgtggga gatactgatg catggtgtga    2160 agcctttttca aggagtgaag aacaatgatg taatcggtcg aattgaaaat ggggaaagat    2220
taccaatgcc tccaaattgt cctcctaccc tctacagcct tatgacgaaa tgctgggcct    2280
atgaccccag caggcggccc aggtttactg aacttaaagc tcagctcagc acaatcctgg    2340
aggaagagaa ggctcagcaa gaagagcgca tgaggatgga gtccagaaga caggccacag    2400
tgtcctggga ctccggaggg tctgatgaag caccgcccaa gccagcagaa ccgggttatc    2460
ccagtccgag gtccagcgaa ggatttttatc ccagcccaca gcacatggta caaaccaatc    2520
attaccaggt ttctggctac cctggttcac atggaatcac agccatggct ggcagcatct    2580
atccaggtca ggcatctctt ttggaccaaa cagattcatg gaatcataga cctcaggaga    2640
tagcaatgtg gcagcccaat gtggaggact ctacagtatt ggacctgcga ggattgggc    2700 aagtgttgcc aacccatctg atggaagagc gtcaatccg acagcaacag gaaatggaag    2760
aagatcagcg ctggctggaa aaagaggaaa gatttctgaa acctgatgtg agactctctc    2820
```

```
gaggcagtat tgacagggag gatggaagtc ttcagggtcc gattggaaac caacatatat    2880
atcagcctgt gggtaaacca gatcctgcag ctccaccaaa gaaaccgcct cgccctggag    2940
ctcccggtca tctgggaagc cttgccagcc tcagcagccc tgctgacagc tacaacgagg    3000
gtgtcaagct tcagccccag gaaatcagcc ccctcctac tgccaacctg gaccggtcga     3060
atgataaggt gtacgagaat gtgacgggcc tggtgaaagc tgtcatcgag atgtccagta    3120
aaatccagcc agccccacca gaggagtatg tccctatggt gaaggaagtc ggcttggccc    3180
tgaggacatt attggccact gtggatgaga ccattcccct cctaccagcc agcacccacc    3240
gagagattga gatggcacag aagctattga actctgacct gggtgagctc atcaacaaga    3300
tgaaactggc ccagcagtat gtcatgacca gcctccagca agagtacaaa aagcaaatgc    3360
tgactgctgc tcacgccctg gctgtggatg ccaaaaactt actcgatgtc attgaccaag    3420
caagactgaa aatgcttggg cagacgagac cacactgagc ctcccctagg agcacgtctt    3480
gctaccctct tttgaagatg ttctctagcc ttccaccagc agcgaggaat taaccctgtg    3540
tcctcagtcg ccagcactta cagctccaac ttttttgaat gaccatctgg ttgaaaaatc    3600
tttctcatat aagtttaacc acactttgat ttgggttcat ttttgtttt gttttttttca    3660 atcatgatat tcagaaaaat ccaggatcca aaatgtggcg tttttctaag aatgaaaatt    3720
atatgtaagc ttttaagcat catgaagaac aatttatgtt cacattaaga tacgttctaa    3780
agggggatgg ccaaggggtg acatcttaat tcctaaacta ccttagctgc atagtggaag    3840
aggagagcat gaagcaaaga attccaggaa acccaagagg ctgagaattc ttttgtctac    3900
catagaatta ttatccagac tggaattttt gtttgttaga acaccttca gttgcaatat     3960 gctaatccca ctttacaaag aatataaaag ctatattttg aagacttgag ttatttcaga    4020
aaaaactaca gccctttttg tcttacctgc cttttacttt cgtgtggata tgtgaagcat    4080
tgggtcggga actagctgta gaacacaact aaaaactcat gtcttttttc acagaataat    4140
gtgccagttt tttgtagcaa tgttatttct cttggaagca gaaatgcttt gtaccagagc    4200
acctccaaac tgcattgagg agaagttcca gaaccatccc cttttccat ttttatataa     4260 tttataaaga aagattaaag ccatgttgac tattttacag ccactggagt taactaaccc    4320
ttccttgtat ctgtcttccc aggagagaat gaagcaaaac aggaatttgg ttttcttttg    4380
atgtccagtt acaccatcca ttctgttaat tttgaaaaaa tataccctcc ctttagtttg    4440
ttgggggata taaattattc tcaggaagaa tataatgaac tgtacagtta ctttgaccta    4500
ttaaaaaggt gttaccagta aagttcttgt tgtaatatcc ttaaaaaaaa              4550
```

<210> SEQ ID NO 9
<211> LENGTH: 91
<212> TYPE: DNA
<213> ORGANISM: Homo sapiens

<400> SEQUENCE: 9

```
gaggttcact ggcttcacgt ggatatgggc gtctccagtg tgagggagaa gtatgagctt    60
gctcacccac cagaggagtg gaaatatgaa t                                   91
```

<210> SEQ ID NO 10
<211> LENGTH: 1055
<212> TYPE: PRT
<213> ORGANISM: Homo sapiens -continued

<400> SEQUENCE: 10

```
Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Pro Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
        275                 280                 285

Asn Pro Thr His Leu Ala Asp Phe Thr Gln Val Gln Thr Ile Gln Tyr
    290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
        355                 360                 365

Ala Leu Pro Ser Ile Pro Lys Leu Ala Asn Ser Glu Lys Gln Gly Met
    370                 375                 380

Arg Thr His Ala Val Ser Val Ser Glu Thr Asp Asp Tyr Ala Glu Ile
385                 390                 395                 400

Ile Asp Glu Glu Asp Thr Tyr Thr Met Pro Ser Thr Arg Asp Tyr Glu
                405                 410                 415
```

```
Ile Gln Arg Glu Arg Ile Glu Leu Gly Arg Cys Ile Gly Glu Gly Gln
                420                 425                 430

Phe Gly Asp Val His Gln Gly Ile Tyr Met Ser Pro Glu Asn Pro Ala
            435                 440                 445

Leu Ala Val Ala Ile Lys Thr Cys Lys Asn Cys Thr Ser Asp Ser Val
        450                 455                 460

Arg Glu Lys Phe Leu Gln Glu Ala Leu Thr Met Arg Gln Phe Asp His
465                 470                 475                 480

Pro His Ile Val Lys Leu Ile Gly Val Ile Thr Glu Asn Pro Val Trp
                485                 490                 495

Ile Ile Met Glu Leu Cys Thr Leu Gly Glu Leu Arg Ser Phe Leu Gln
            500                 505                 510

Val Arg Lys Tyr Ser Leu Asp Leu Ala Ser Leu Ile Leu Tyr Ala Tyr
        515                 520                 525

Gln Leu Ser Thr Ala Leu Ala Tyr Leu Glu Ser Lys Arg Phe Val His
        530                 535                 540

Arg Asp Ile Ala Ala Arg Asn Val Leu Val Ser Ser Asn Asp Cys Val
545                 550                 555                 560

Lys Leu Gly Asp Phe Gly Leu Ser Arg Tyr Met Glu Asp Ser Thr Tyr
                565                 570                 575

Tyr Lys Ala Ser Lys Gly Lys Leu Pro Ile Lys Trp Met Ala Pro Glu
            580                 585                 590

Ser Ile Asn Phe Arg Arg Phe Thr Ser Ala Ser Asp Val Trp Met Phe
        595                 600                 605

Gly Val Cys Met Trp Glu Ile Leu Met His Gly Val Lys Pro Phe Gln
        610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
                645                 650                 655

Lys Cys Trp Ala Tyr Asp Pro Ser Arg Arg Pro Arg Phe Thr Glu Leu
            660                 665                 670

Lys Ala Gln Leu Ser Thr Ile Leu Glu Glu Lys Ala Gln Gln Glu
        675                 680                 685

Glu Arg Met Arg Met Glu Ser Arg Arg Gln Ala Thr Val Ser Trp Asp
        690                 695                 700

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
                725                 730                 735

Val Gln Thr Asn His Tyr Gln Val Ser Gly Tyr Pro Gly Ser His Gly
            740                 745                 750

Ile Thr Ala Met Ala Gly Ser Ile Tyr Pro Gly Gln Ala Ser Leu Leu
        755                 760                 765

Asp Gln Thr Asp Ser Trp Asn His Arg Pro Gln Glu Ile Ala Met Trp
        770                 775                 780

Gln Pro Asn Val Glu Asp Ser Thr Val Leu Asp Leu Arg Gly Ile Gly
785                 790                 795                 800

Gln Val Leu Pro Thr His Leu Met Glu Glu Arg Leu Ile Arg Gln Gln
                805                 810                 815

Gln Glu Met Glu Glu Asp Gln Arg Trp Leu Glu Lys Glu Glu Arg Phe
            820                 825                 830
```

```
Leu Lys Pro Asp Val Arg Leu Ser Arg Gly Ser Ile Asp Arg Glu Asp
            835                 840                 845

Gly Ser Leu Gln Gly Pro Ile Gly Asn Gln His Ile Tyr Gln Pro Val
850                 855                 860

Gly Lys Pro Asp Pro Ala Ala Pro Pro Lys Lys Pro Pro Arg Pro Gly
865                 870                 875                 880

Ala Pro Gly His Leu Gly Ser Leu Ala Ser Leu Ser Ser Pro Ala Asp
                885                 890                 895

Ser Tyr Asn Glu Gly Val Lys Pro Trp Arg Leu Gln Pro Gln Glu Ile
            900                 905                 910

Ser Pro Pro Pro Thr Ala Asn Leu Asp Arg Ser Asn Asp Lys Val Tyr
            915                 920                 925

Glu Asn Val Thr Gly Leu Val Lys Ala Val Ile Glu Met Ser Ser Lys
            930                 935                 940

Ile Gln Pro Ala Pro Pro Glu Glu Tyr Val Pro Met Val Lys Glu Val
945                 950                 955                 960

Gly Leu Ala Leu Arg Thr Leu Leu Ala Thr Val Asp Glu Thr Ile Pro
                965                 970                 975

Leu Leu Pro Ala Ser Thr His Arg Glu Ile Glu Met Ala Gln Lys Leu
            980                 985                 990

Leu Asn Ser Asp Leu Gly Glu Leu Ile Asn Lys Met Lys Leu Ala Gln
            995                 1000                1005

Gln Tyr Val Met Thr Ser Leu Gln Gln Glu Tyr Lys Lys Gln Met Leu
            1010                1015                1020

Thr Ala Ala His Ala Leu Ala Val Asp Ala Lys Asn Leu Leu Asp Val
1025                1030                1035                1040

Ile Asp Gln Ala Arg Leu Lys Met Leu Gly Gln Thr Arg Pro His
                1045                1050                1055

<210> SEQ ID NO 11
<211> LENGTH: 1026
<212> TYPE: PRT
<213> ORGANISM: Homo sapiens

<400> SEQUENCE: 11

Met Ala Ala Ala Tyr Leu Asp Pro Asn Leu Asn His Thr Pro Asn
1               5                   10                  15                  Asn

Ser Ser Thr Lys Thr His Leu Gly Thr Gly Met Glu Arg Ser Pro Gly
            20                  25                  30

Ala Met Glu Arg Val Leu Lys Val Phe His Tyr Phe Glu Ser Asn Ser
            35                  40                  45

Glu Pro Thr Thr Trp Ala Ser Ile Ile Arg His Gly Asp Ala Thr Asp
50                  55                  60

Val Arg Gly Ile Ile Gln Lys Ile Val Asp Ser His Lys Val Lys His
65                  70                  75                  80

Val Ala Cys Tyr Gly Phe Arg Leu Ser His Leu Arg Ser Glu Glu Val
                85                  90                  95

His Trp Leu His Val Asp Met Gly Val Ser Ser Val Arg Glu Lys Tyr
            100                 105                 110

Glu Leu Ala His Pro Pro Glu Glu Trp Lys Tyr Glu Leu Arg Ile Arg
            115                 120                 125

Tyr Leu Pro Lys Gly Phe Leu Asn Gln Phe Thr Glu Asp Lys Pro Thr
130                 135                 140

Leu Asn Phe Phe Tyr Gln Gln Val Lys Ser Asp Tyr Met Leu Glu Ile
145                 150                 155                 160
```

-continued

Ala Asp Gln Val Asp Gln Glu Ile Ala Leu Lys Leu Gly Cys Leu Glu
            165                 170                 175
Ile Arg Arg Ser Tyr Trp Glu Met Arg Gly Asn Ala Leu Glu Lys Lys
            180                 185                 190
Ser Asn Tyr Glu Val Leu Glu Lys Asp Val Gly Leu Lys Arg Phe Phe
            195                 200                 205
Pro Lys Ser Leu Leu Asp Ser Val Lys Ala Lys Thr Leu Arg Lys Leu
        210                 215                 220
Ile Gln Gln Thr Phe Arg Gln Phe Ala Asn Leu Asn Arg Glu Glu Ser
225                 230                 235                 240
Ile Leu Lys Phe Phe Glu Ile Leu Ser Pro Val Tyr Arg Phe Asp Lys
            245                 250                 255
Glu Cys Phe Lys Cys Ala Leu Gly Ser Ser Trp Ile Ile Ser Val Glu
            260                 265                 270
Leu Ala Ile Gly Pro Glu Glu Gly Ile Ser Tyr Leu Thr Asp Lys Gly
            275                 280                 285
Cys Asn Pro Thr His Leu Ala Asp Phe Thr Gln Val Gln Thr Ile Gln
            290                 295                 300
Tyr Ser Asn Ser Glu Asp Lys Asp Arg Lys Gly Met Leu Gln Leu Lys
305                 310                 315                 320
Ile Ala Gly Ala Pro Glu Pro Leu Thr Val Thr Ala Pro Ser Leu Thr
            325                 330                 335
Ile Ala Glu Asn Met Ala Asp Leu Ile Asp Gly Tyr Cys Arg Leu Val
            340                 345                 350
Asn Gly Thr Ser Gln Ser Phe Ile Ile Arg Pro Gln Lys Glu Gly Glu
            355                 360                 365
Arg Ala Leu Pro Ser Ile Pro Lys Leu Ala Asn Ser Glu Lys Gln Gly
            370                 375                 380
Met Arg Thr His Ala Val Ser Val Ser Glu Thr Asp Asp Tyr Ala Glu
385                 390                 395                 400
Ile Ile Asp Glu Glu Asp Thr Tyr Thr Met Pro Ser Thr Arg Asp Tyr
            405                 410                 415
Glu Ile Gln Arg Glu Arg Ile Glu Leu Gly Arg Cys Ile Gly Glu Gly
            420                 425                 430
Gln Phe Gly Asp Val His Gln Gly Ile Tyr Met Ser Pro Glu Asn Pro
            435                 440                 445
Ala Leu Ala Val Ala Ile Lys Thr Cys Lys Asn Cys Thr Ser Asp Ser
            450                 455                 460
Val Arg Glu Lys Phe Leu Gln Glu Ala Leu Thr Met Arg Gln Phe Asp
465                 470                 475                 480
His Pro His Ile Val Lys Leu Ile Gly Val Ile Thr Glu Asn Pro Val
            485                 490                 495
Trp Ile Ile Met Glu Leu Cys Thr Leu Gly Glu Leu Arg Ser Phe Leu
            500                 505                 510
Gln Val Arg Lys Tyr Ser Leu Asp Leu Ala Ser Leu Ile Leu Tyr Ala
            515                 520                 525
Tyr Gln Leu Ser Thr Ala Leu Ala Tyr Leu Glu Ser Lys Arg Phe Val
            530                 535                 540
His Arg Asp Ile Ala Ala Arg Asn Val Leu Val Ser Ser Asn Asp Cys
545                 550                 555                 560
Val Lys Leu Gly Asp Phe Gly Leu Ser Arg Tyr Met Glu Asp Ser Thr
            565                 570                 575

-continued

Tyr Tyr Lys Ala Ser Lys Gly Lys Leu Pro Ile Lys Trp Met Ala Pro
            580                 585                 590

Glu Ser Ile Asn Phe Arg Arg Phe Thr Ser Ala Ser Asp Val Trp Met
            595                 600                 605

Phe Gly Val Cys Met Trp Glu Ile Leu Met His Gly Val Lys Pro Phe
            610                 615                 620

Gln Gly Val Lys Asn Asn Asp Val Ile Gly Arg Ile Glu Asn Gly Glu
625                 630                 635                 640

Arg Leu Pro Met Pro Pro Asn Cys Pro Pro Thr Leu Tyr Ser Leu Met
            645                 650                 655

Thr Lys Cys Trp Ala Tyr Asp Pro Ser Arg Arg Pro Arg Phe Thr Glu
            660                 665                 670

Leu Lys Ala Gln Leu Ser Thr Ile Leu Glu Glu Lys Ala Gln Gln
            675                 680                 685

Glu Glu Arg Met Arg Met Glu Ser Arg Arg Gln Ala Thr Val Ser Trp
            690                 695                 700

Asp Ser Gly Gly Ser Asp Glu Ala Pro Pro Lys Pro Ser Arg Pro Gly
705                 710                 715                 720

Tyr Pro Ser Pro Arg Ser Ser Glu Gly Phe Tyr Pro Ser Pro Gln His
            725                 730                 735

Met Val Gln Thr Asn His Tyr Gln Val Ser Gly Tyr Pro Gly Ser His
            740                 745                 750

Gly Ile Thr Ala Met Ala Gly Ser Ile Tyr Pro Gly Gln Ala Ser Leu
            755                 760                 765

Leu Asp Gln Thr Asp Ser Trp Asn His Arg Pro Gln Glu Ile Ala Met
770                 775                 780

Trp Gln Pro Asn Val Glu Asp Ser Thr Val Leu Asp Leu Arg Gly Ile
785                 790                 795                 800

Gly Gln Val Leu Pro Thr His Leu Met Glu Glu Arg Leu Ile Arg Gln
            805                 810                 815

Gln Gln Glu Met Glu Glu Asp Gln Arg Trp Leu Glu Lys Glu Glu Arg
            820                 825                 830

Phe Leu Lys Pro Asp Val Arg Leu Ser Arg Gly Ser Ile Asp Arg Glu
            835                 840                 845

Asp Gly Ser Leu Gln Gly Pro Ile Gly Asn Gln His Ile Tyr Gln Pro
850                 855                 860

Val Gly Lys Pro Asp Pro Ala Ala Pro Pro Lys Lys Pro Pro Arg Pro
865                 870                 875                 880

Gly Ala Pro Gly His Leu Gly Ser Leu Ala Ser Leu Ser Ser Pro Ala
            885                 890                 895

Asp Ser Tyr Asn Glu Gly Val Lys Leu Gln Pro Gln Glu Ile Ser Pro
            900                 905                 910

Pro Pro Thr Ala Asn Leu Asp Arg Ser Asn Asp Lys Val Tyr Glu Asn
            915                 920                 925

Val Thr Gly Leu Val Lys Ala Val Ile Glu Met Ser Ser Lys Ile Gln
930                 935                 940

Pro Ala Pro Pro Glu Glu Tyr Val Pro Met Val Lys Ile Glu Met Ala
945                 950                 955                 960

Gln Lys Leu Leu Asn Ser Asp Leu Gly Glu Leu Ile Asn Lys Met Lys
            965                 970                 975

Leu Ala Gln Gln Tyr Val Met Thr Ser Leu Gln Gln Glu Tyr Lys Lys
            980                 985                 990

-continued

Gln Met Leu Thr Ala Ala His Ala Leu Ala Val Asp Ala Lys Asn Leu
            995                1000                1005

Leu Asp Val Ile Asp Gln Ala Arg Leu Lys Met Leu Gly Gln Thr Arg
        1010                1015                1020

Pro His
1025

<210> SEQ ID NO 12
<211> LENGTH: 7
<212> TYPE: PRT
<213> ORGANISM: Artificial Sequence
<220> FEATURE:
<223> OTHER INFORMATION: A synthetic peptide

<400> SEQUENCE: 12

Ala Ala His Pro Pro Glu Glu
1               5

<210> SEQ ID NO 13
<211> LENGTH: 7
<212> TYPE: PRT
<213> ORGANISM: Artificial Sequence
<220> FEATURE:
<223> OTHER INFORMATION: A synthetic peptide

<400> SEQUENCE: 13

Leu Ala His Asn Pro Glu Glu
1               5

<210> SEQ ID NO 14
<211> LENGTH: 7
<212> TYPE: PRT
<213> ORGANISM: Artificial Sequence
<220> FEATURE:
<223> OTHER INFORMATION: A synthetic peptide

<400> SEQUENCE: 14

Leu Ala His Cys Pro Glu Glu
1               5

<210> SEQ ID NO 15
<211> LENGTH: 7
<212> TYPE: PRT
<213> ORGANISM: Artificial Sequence
<220> FEATURE:
<223> OTHER INFORMATION: A synthetic peptide

<400> SEQUENCE: 15

Leu Ala His Gly Pro Glu Glu
1               5

<210> SEQ ID NO 16
<211> LENGTH: 7
<212> TYPE: PRT
<213> ORGANISM: Artificial Sequence
<220> FEATURE:
<223> OTHER INFORMATION: A synthetic peptide

<400> SEQUENCE: 16

Leu Ala His Pro Lys Glu Glu
1               5

<210> SEQ ID NO 17
<211> LENGTH: 7
<212> TYPE: PRT
<213> ORGANISM: Artificial Sequence

```
<220> FEATURE:
<223> OTHER INFORMATION: A synthetic peptide

<400> SEQUENCE: 17

Leu Ala His Pro Ser Glu Glu
1               5

<210> SEQ ID NO 18
<211> LENGTH: 7
<212> TYPE: PRT
<213> ORGANISM: Artificial Sequence
<220> FEATURE:
<223> OTHER INFORMATION: A synthetic peptide

<400> SEQUENCE: 18

Ala Ala His Asn Lys Glu Glu
1               5

<210> SEQ ID NO 19
<211> LENGTH: 7
<212> TYPE: PRT
<213> ORGANISM: Artificial Sequence
<220> FEATURE:
<223> OTHER INFORMATION: A synthetic peptide

<400> SEQUENCE: 19

Ala Ala His Cys Gly Glu Glu
1               5

<210> SEQ ID NO 20
<211> LENGTH: 7
<212> TYPE: PRT
<213> ORGANISM: Artificial Sequence
<220> FEATURE:
<223> OTHER INFORMATION: A synthetic peptide

<400> SEQUENCE: 20

Ala Ala His Ala Ala Glu Glu
1               5

<210> SEQ ID NO 21
<211> LENGTH: 126
<212> TYPE: PRT
<213> ORGANISM: Artificial Sequence
<220> FEATURE:
<223> OTHER INFORMATION: A synthetic peptide

<400> SEQUENCE: 21

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
                20                  25                  30

Met Glu Arg Val Leu Lys Val Phe His Tyr Phe Glu Ser Asn Ser Glu
            35                  40                  45

Pro Thr Thr Trp Ala Ser Ile Ile Arg His Gly Asp Ala Thr Asp Val
        50                  55                  60

Arg Gly Ile Ile Gln Lys Ile Val Asp Ser His Lys Val Lys Asn Val
65                  70                  75                  80

Ala Cys Tyr Gly Phe Arg Leu Ser His Leu Arg Ser Glu Glu Val His
                85                  90                  95
```

```
Trp Leu His Val Asp Met Gly Val Ser Ser Val Arg Glu Lys Tyr Glu
            100                 105                 110

Leu Ala His Pro Ser Glu Glu Trp Lys Tyr Glu Leu Arg Ile
        115                 120                 125
```

<210> SEQ ID NO 22
<211> LENGTH: 126
<212> TYPE: PRT
<213> ORGANISM: Artificial Sequence
<220> FEATURE:
<223> OTHER INFORMATION: A synthetic peptide

<400> SEQUENCE: 22

```
Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
            35                  40                  45

Pro Thr Thr Trp Ala Ser Ile Ile Arg His Gly Asp Ala Thr Asp Val
        50                  55                  60

Arg Gly Ile Ile Gln Lys Ile Val Asp Ser His Lys Val Lys Asn Val
65                  70                  75                  80

Ala Cys Tyr Gly Phe Arg Leu Ser His Leu Arg Ser Glu Val His
                85                  90                  95

Trp Leu His Val Asp Met Gly Val Ser Ser Val Arg Glu Lys Tyr Glu
            100                 105                 110

Ala Ala His Cys Gly Glu Glu Trp Lys Tyr Glu Leu Arg Ile
        115                 120                 125
```

<210> SEQ ID NO 23
<211> LENGTH: 7
<212> TYPE: PRT
<213> ORGANISM: Artificial Sequence
<220> FEATURE:
<223> OTHER INFORMATION: A synthetic peptide

<400> SEQUENCE: 23

```
His Pro Glu Leu Ala Pro Glu
1               5
```

<210> SEQ ID NO 24
<211> LENGTH: 7
<212> TYPE: PRT
<213> ORGANISM: Artificial Sequence
<220> FEATURE:
<223> OTHER INFORMATION: A synthetic peptide

<400> SEQUENCE: 24

```
Ala Ala His Pro Ser Glu Glu
1               5
```

<210> SEQ ID NO 25
<211> LENGTH: 5
<212> TYPE: PRT
<213> ORGANISM: Artificial Sequence
<220> FEATURE:
<223> OTHER INFORMATION: A synthetic peptide

<400> SEQUENCE: 25

```
Leu Ala His Pro Pro
1               5
```

```
<210> SEQ ID NO 26
<211> LENGTH: 7
<212> TYPE: PRT
<213> ORGANISM: Artificial Sequence
<220> FEATURE:
<223> OTHER INFORMATION: A synthetic peptide

<400> SEQUENCE: 26

Trp Lys Tyr Glu Leu Arg Ile
1               5

<210> SEQ ID NO 27
<211> LENGTH: 510
<212> TYPE: PRT
<213> ORGANISM: Artificial Sequence
<220> FEATURE:
<223> OTHER INFORMATION: A synthetic peptide

<400> SEQUENCE: 27

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Ala Ala His Pro Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
        275                 280                 285

Asn Pro Thr His Leu Ala Asp Phe Thr Gln Val Gln Thr Ile Gln Tyr
    290                 295                 300
```

```
Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
            325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
        355                 360                 365

Ala Leu Pro Ser Ile Pro Lys Leu Ala Asn Ser Lys Gln Gly Met
    370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415

Ser Lys Ser Tyr Gly Ile Asp Glu Ala Arg Asp Tyr Glu Ile Gln Arg
            420                 425                 430

Glu Arg Ile Glu Leu Gly Arg Cys Ile Gly Gly Gln Phe Gly Asp
                435                 440                 445

Val His Gln Gly Ile Tyr Met Ser Pro Glu Asn Pro Ala Leu Ala Val
450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
            485                 490                 495

Cys Phe Ala His His Ser Ile Leu Ser Val Leu His Ser Thr
            500                 505                 510

<210> SEQ ID NO 28
<211> LENGTH: 510
<212> TYPE: PRT
<213> ORGANISM: Artificial Sequence
<220> FEATURE:
<223> OTHER INFORMATION: A synthetic peptide

<400> SEQUENCE: 28

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Cys Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Leu Glu Ile Ala
145                 150                 155                 160
```

Asp Gln Val Asp Gln Glu Ile Ala Leu Lys Leu Gly Cys Leu Glu Ile
            165                 170                 175

Arg Arg Ser Tyr Trp Glu Met Arg Gly Asn Ala Leu Glu Lys Lys Ser
        180                 185                 190

Asn Tyr Glu Val Leu Glu Lys Asp Val Gly Leu Lys Arg Phe Phe Pro
    195                 200                 205

Lys Ser Leu Leu Asp Ser Val Lys Ala Lys Thr Leu Arg Lys Leu Ile
210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
            245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
            275                 280                 285

Asn Pro Thr His Leu Ala Asp Phe Thr Gln Val Gln Thr Ile Gln Tyr
            290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
            325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
            355                 360                 365

Ala Leu Pro Ser Ile Pro Lys Leu Ala Asn Ser Glu Lys Gln Gly Met
            370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415

Ser Lys Ser Tyr Gly Ile Asp Glu Ala Arg Asp Tyr Glu Ile Gln Arg
            420                 425                 430

Glu Arg Ile Glu Leu Gly Arg Cys Ile Gly Glu Gly Gln Phe Gly Asp
            435                 440                 445

Val His Gln Gly Ile Tyr Met Ser Pro Glu Asn Pro Ala Leu Ala Val
    450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
                485                 490                 495

Cys Phe Ala His His Ser Ile Leu Ser Val Leu His Ser Thr
            500                 505                 510

<210> SEQ ID NO 29
<211> LENGTH: 510
<212> TYPE: PRT
<213> ORGANISM: Artificial Sequence
<220> FEATURE:
<223> OTHER INFORMATION: A synthetic peptide

<400> SEQUENCE: 29

```
Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Gly Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
        275                 280                 285

Asn Pro Thr His Leu Ala Asp Phe Thr Gln Val Gln Thr Ile Gln Tyr
    290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
        355                 360                 365

Ala Leu Pro Ser Ile Pro Lys Leu Ala Asn Ser Glu Lys Gln Gly Met
    370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415
```

```
Ser Lys Ser Tyr Gly Ile Asp Glu Ala Arg Asp Tyr Glu Ile Gln Arg
            420                 425                 430

Glu Arg Ile Glu Leu Gly Arg Cys Ile Gly Gly Gln Phe Gly Asp
        435                 440                 445

Val His Gln Gly Ile Tyr Met Ser Pro Glu Asn Pro Ala Leu Ala Val
450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
                485                 490                 495

Cys Phe Ala His His Ser Ile Leu Ser Val Leu His Ser Thr
            500                 505                 510

<210> SEQ ID NO 30
<211> LENGTH: 510
<212> TYPE: PRT
<213> ORGANISM: Artificial Sequence
<220> FEATURE:
<223> OTHER INFORMATION: A synthetic peptide

<400> SEQUENCE: 30

Met Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Cys Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270
```

```
Ala Ile Gly Pro Glu Glu Gly Ile Ser Tyr Leu Thr Asp Lys Gly Cys
            275                 280                 285

Asn Pro Thr His Leu Ala Asp Phe Thr Gln Val Gln Thr Ile Gln Tyr
            290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
            325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
            355                 360                 365

Ala Leu Pro Ser Ile Pro Lys Leu Ala Asn Ser Glu Lys Gln Gly Met
            370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
            405                 410                 415

Ser Lys Ser Tyr Gly Ile Asp Glu Ala Arg Asp Tyr Glu Ile Gln Arg
            420                 425                 430

Glu Arg Ile Glu Leu Gly Arg Cys Ile Gly Glu Gly Gln Phe Gly Asp
            435                 440                 445

Val His Gln Gly Ile Tyr Met Ser Pro Glu Asn Pro Ala Leu Ala Val
            450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
            485                 490                 495

Cys Phe Ala His His Ser Ile Leu Ser Val Leu His Ser Thr
            500                 505                 510

<210> SEQ ID NO 31
<211> LENGTH: 510
<212> TYPE: PRT
<213> ORGANISM: Artificial Sequence
<220> FEATURE:
<223> OTHER INFORMATION: A synthetic peptide

<400> SEQUENCE: 31

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
            35                  40                  45

Pro Thr Thr Trp Ala Ser Ile Ile Arg His Gly Asp Ala Thr Asp Val
            50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
            85                  90                  95

Trp Leu His Val Asp Met Gly Val Ser Ser Val Arg Glu Lys Tyr Glu
            100                 105                 110

Leu Ala His Lys Pro Glu Glu Trp Lys Tyr Glu Leu Arg Ile Arg Tyr
            115                 120                 125
```

Leu Pro Lys Gly Phe Leu Asn Gln Phe Thr Glu Asp Lys Pro Thr Leu
130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
            165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
                260                 265                 270

Ala Ile Gly Pro Glu Glu Gly Ile Ser Tyr Leu Thr Asp Lys Gly Cys
        275                 280                 285

Asn Pro Thr His Leu Ala Asp Phe Thr Gln Val Gln Thr Ile Gln Tyr
290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
        355                 360                 365

Ala Leu Pro Ser Ile Pro Lys Leu Ala Asn Ser Glu Lys Gln Gly Met
370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415

Ser Lys Ser Tyr Gly Ile Asp Glu Ala Arg Asp Tyr Glu Ile Gln Arg
            420                 425                 430

Glu Arg Ile Glu Leu Gly Arg Cys Ile Gly Gly Gln Phe Gly Asp
        435                 440                 445

Val His Gln Gly Ile Tyr Met Ser Pro Glu Asn Pro Ala Leu Ala Val
450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
                485                 490                 495

Cys Phe Ala His His Ser Ile Leu Ser Val Leu His Ser Thr
                500                 505                 510

<210> SEQ ID NO 32
<211> LENGTH: 510
<212> TYPE: PRT
<213> ORGANISM: Artificial Sequence
<220> FEATURE:
<223> OTHER INFORMATION: A synthetic peptide

```
<400> SEQUENCE: 32

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Ser Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
        275                 280                 285

Asn Pro Thr His Leu Ala Asp Phe Thr Gln Val Gln Thr Ile Gln Tyr
    290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
        355                 360                 365

Ala Leu Pro Ser Ile Pro Lys Leu Ala Asn Ser Glu Lys Gln Gly Met
    370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415
```

```
Ser Lys Ser Tyr Gly Ile Asp Glu Ala Arg Asp Tyr Glu Ile Gln Arg
            420                 425                 430

Glu Arg Ile Glu Leu Gly Arg Cys Ile Gly Gly Gln Phe Gly Asp
            435                 440                 445

Val His Gln Gly Ile Tyr Met Ser Pro Glu Asn Pro Ala Leu Ala Val
450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
                485                 490                 495

Cys Phe Ala His His Ser Ile Leu Ser Val Leu His Ser Thr
                500                 505                 510
```

<210> SEQ ID NO 33
<211> LENGTH: 510
<212> TYPE: PRT
<213> ORGANISM: Artificial Sequence
<220> FEATURE:
<223> OTHER INFORMATION: A synthetic peptide

<400> SEQUENCE: 33

```
Met Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
                20                  25                  30

Met Glu Arg Val Leu Lys Val Phe His Tyr Phe Glu Ser Asn Ser Glu
            35                  40                  45

Pro Thr Thr Trp Ala Ser Ile Ile Arg His Gly Asp Ala Thr Asp Val
        50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
                100                 105                 110

Ala Ala His Asn Lys Glu Glu Trp Lys Tyr Glu Leu Arg Ile Arg Tyr
            115                 120                 125

Leu Pro Lys Gly Phe Leu Asn Gln Phe Thr Glu Asp Lys Pro Thr Leu
130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
                180                 185                 190

Asn Tyr Glu Val Leu Glu Lys Asp Val Gly Leu Lys Arg Phe Phe Pro
            195                 200                 205

Lys Ser Leu Leu Asp Ser Val Lys Ala Lys Thr Leu Arg Lys Leu Ile
210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
                260                 265                 270
```

```
Ala Ile Gly Pro Glu Gly Ile Ser Tyr Leu Thr Asp Lys Gly Cys
            275                 280                 285

Asn Pro Thr His Leu Ala Asp Phe Thr Gln Val Gln Thr Ile Gln Tyr
290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
        355                 360                 365

Ala Leu Pro Ser Ile Pro Lys Leu Ala Asn Ser Glu Lys Gln Gly Met
    370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415

Ser Lys Ser Tyr Gly Ile Asp Glu Ala Arg Asp Tyr Glu Ile Gln Arg
            420                 425                 430

Glu Arg Ile Glu Leu Gly Arg Cys Ile Gly Glu Gly Gln Phe Gly Asp
        435                 440                 445

Val His Gln Gly Ile Tyr Met Ser Pro Glu Asn Pro Ala Leu Ala Val
    450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
                485                 490                 495

Cys Phe Ala His His Ser Ile Leu Ser Val Leu His Ser Thr
            500                 505                 510

<210> SEQ ID NO 34
<211> LENGTH: 510
<212> TYPE: PRT
<213> ORGANISM: Artificial Sequence
<220> FEATURE:
<223> OTHER INFORMATION: A synthetic peptide

<400> SEQUENCE: 34

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Ala Ala His Cys Gly Glu Glu Trp Lys Tyr Glu Leu Arg Ile Arg Tyr
        115                 120                 125
```

Leu Pro Lys Gly Phe Leu Asn Gln Phe Thr Glu Asp Lys Pro Thr Leu
130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
                180                 185                 190

Asn Tyr Glu Val Leu Glu Lys Asp Val Gly Leu Lys Arg Phe Phe Pro
            195                 200                 205

Lys Ser Leu Leu Asp Ser Val Lys Ala Lys Thr Leu Arg Lys Leu Ile
210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
                260                 265                 270

Ala Ile Gly Pro Glu Glu Gly Ile Ser Tyr Leu Thr Asp Lys Gly Cys
            275                 280                 285

Asn Pro Thr His Leu Ala Asp Phe Thr Gln Val Gln Thr Ile Gln Tyr
290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
            355                 360                 365

Ala Leu Pro Ser Ile Pro Lys Leu Ala Asn Ser Glu Lys Gln Gly Met
370                 375                 380

Arg Thr His Ala Val Ser Val Ser Asp Glu Ile Ser Gly Asp Glu Thr
385                 390                 395                 400

Asp Asp Tyr Ala Glu Ile Ile Asp Glu Glu Asp Thr Tyr Thr Met Pro
                405                 410                 415

Ser Lys Ser Tyr Gly Ile Asp Glu Ala Arg Asp Tyr Glu Ile Gln Arg
                420                 425                 430

Glu Arg Ile Glu Leu Gly Arg Cys Ile Gly Gly Gln Phe Gly Asp
            435                 440                 445

Val His Gln Gly Ile Tyr Met Ser Pro Glu Asn Pro Ala Leu Ala Val
450                 455                 460

Ala Ile Lys Thr Cys Lys Asn Cys Thr Ser Asp Ser Val Arg Glu Lys
465                 470                 475                 480

Phe Leu Gln Glu Ala Cys Leu Lys Leu Pro Gly Asp Lys Asp His Val
                485                 490                 495

Cys Phe Ala His His Ser Ile Leu Ser Val Leu His Ser Thr
                500                 505                 510

<210> SEQ ID NO 35
<211> LENGTH: 470
<212> TYPE: PRT
<213> ORGANISM: Artificial Sequence
<220> FEATURE:
<223> OTHER INFORMATION: A synthetic peptide

<400> SEQUENCE: 35

```
His Tyr Phe Glu Ser Asn Ser Glu Pro Thr Thr Trp Ala Ser Ile Ile
1               5                   10                  15

Arg His Gly Asp Ala Thr Asp Val Arg Gly Ile Ile Gln Lys Ile Val
            20                  25                  30

Asp Ser His Lys Val Lys His Val Ala Cys Tyr Gly Phe Arg Leu Ser
        35                  40                  45

His Leu Arg Ser Glu Glu Val His Trp Leu His Val Asp Met Gly Val
    50                  55                  60

Ser Ser Val Arg Glu Lys Tyr Glu Ala Ala His Ala Ala Glu Glu Trp
65                  70                  75                  80

Lys Tyr Glu Leu Arg Ile Arg Tyr Leu Pro Lys Gly Phe Leu Asn Gln
                85                  90                  95

Phe Thr Glu Asp Lys Pro Thr Leu Asn Phe Phe Tyr Gln Gln Val Lys
            100                 105                 110

Ser Asp Tyr Met Leu Glu Ile Ala Asp Gln Val Asp Gln Glu Ile Ala
        115                 120                 125

Leu Lys Leu Gly Cys Leu Glu Ile Arg Arg Ser Tyr Trp Glu Met Arg
130                 135                 140

Gly Asn Ala Leu Glu Lys Lys Ser Asn Tyr Glu Val Leu Glu Lys Asp
145                 150                 155                 160

Val Gly Leu Lys Arg Phe Phe Pro Lys Ser Leu Leu Asp Ser Val Lys
                165                 170                 175

Ala Lys Thr Leu Arg Lys Leu Ile Gln Gln Thr Phe Arg Gln Phe Ala
            180                 185                 190

Asn Leu Asn Arg Glu Glu Ser Ile Leu Lys Phe Phe Glu Ile Leu Ser
        195                 200                 205

Pro Val Tyr Arg Phe Asp Lys Glu Cys Phe Lys Cys Ala Leu Gly Ser
    210                 215                 220

Ser Trp Ile Ile Ser Val Glu Leu Ala Ile Gly Pro Glu Glu Gly Ile
225                 230                 235                 240

Ser Tyr Leu Thr Asp Lys Gly Cys Asn Pro Thr His Leu Ala Asp Phe
                245                 250                 255

Thr Gln Val Gln Thr Ile Gln Tyr Ser Asn Ser Glu Asp Lys Asp Arg
            260                 265                 270

Lys Gly Met Leu Gln Leu Lys Ile Ala Gly Ala Pro Glu Pro Leu Thr
        275                 280                 285

Val Thr Ala Pro Ser Leu Thr Ile Ala Glu Asn Met Ala Asp Leu Ile
290                 295                 300

Asp Gly Tyr Cys Arg Leu Val Asn Gly Thr Ser Gln Ser Phe Ile Ile
305                 310                 315                 320

Arg Pro Gln Lys Glu Gly Glu Arg Ala Leu Pro Ser Ile Pro Lys Leu
                325                 330                 335

Ala Asn Ser Glu Lys Gln Gly Met Arg Thr His Ala Val Ser Val Ser
            340                 345                 350

Asp Glu Ile Ser Gly Asp Glu Thr Asp Tyr Ala Glu Ile Ile Asp
        355                 360                 365

Glu Glu Asp Thr Tyr Thr Met Pro Ser Lys Ser Tyr Gly Ile Asp Glu
    370                 375                 380

Ala Arg Asp Tyr Glu Ile Gln Arg Glu Arg Ile Glu Leu Gly Arg Cys
385                 390                 395                 400

Ile Gly Glu Gly Gln Phe Gly Asp Val His Gln Gly Ile Tyr Met Ser
                405                 410                 415
```

Pro Glu Asn Pro Ala Leu Ala Val Ala Ile Lys Thr Cys Lys Asn Cys
            420                 425                 430

Thr Ser Asp Ser Val Arg Glu Lys Phe Leu Gln Glu Ala Cys Leu Lys
        435                 440                 445

Leu Pro Gly Asp Lys Asp His Val Cys Phe Ala His His Ser Ile Leu
    450                 455                 460

Ser Val Leu His Ser Thr
465             470

<210> SEQ ID NO 36
<211> LENGTH: 51
<212> TYPE: DNA
<213> ORGANISM: Artificial Sequence
<220> FEATURE:
<223> OTHER INFORMATION: A synthetic oligonucleotide

<400> SEQUENCE: 36
ccggaattcg tctccagtgt gagggagaag tatgagcttg ctcacccacc a         51

<210> SEQ ID NO 37
<211> LENGTH: 51
<212> TYPE: DNA
<213> ORGANISM: Artificial Sequence
<220> FEATURE:
<223> OTHER INFORMATION: A synthetic oligonucleotide

<400> SEQUENCE: 37
ccgctcgaga attctcaatt catatttcca ctcctctggt gggtgagcaa g         51

<210> SEQ ID NO 38
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 38
ccggaattcg tctccagtgt gagggagaag tatgagcttg ct              42

<210> SEQ ID NO 39
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 39
ccgctcgagc tcctctggtg ggtgagcaag ctcatacttc tc              42

<210> SEQ ID NO 40
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 40
ccggaattcc ttgctcaccc accagaggag tggaaatat                 39

<210> SEQ ID NO 41
<211> LENGTH: 39
<212> TYPE: DNA
<213> ORGANISM: Artificial Sequence
<220> FEATURE:
<223> OTHER INFORMATION: A synthetic oligonucleotide

```
<400> SEQUENCE: 41
ccgctcgaga attctcaatt catatttcca ctcctcggt                  39

<210> SEQ ID NO 42
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 42
ccggaattcc ttgctcaccc accagaggag                            30

<210> SEQ ID NO 43
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 43
ccgctcgagc tcctctggtg ggtgagcaag                            30

<210> SEQ ID NO 44
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 44
ccgtcgacgc ggccgcatgc ttgctcaccc accagaggag taa             43

<210> SEQ ID NO 45
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 45
tcttatctag aagcttttac tcctctggtg ggtgagcaag cat             43

<210> SEQ ID NO 46
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 46
ccgtcgacgc ggccgcatgc acccagagct tgctccagag taa             43

<210> SEQ ID NO 47
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 47
tcttatctag aagcttttac tctggagcaa gctctgggtg cat             43
```

INHIBITING FAK-AKT INTERACTION TO INHIBIT METASTASIS

CLAIM FOR PRIORITY

This application is a U.S. National Stage Filing under 35 U.S.C. 371 from International Application No. PCT/US2018/042919, filed on Jul. 19, 2018, and published as WO 2019/018666 on Jan. 24, 2019 which claims benefit of priority to the filing date of U.S. Provisional Application Ser. No. 62/678,561, filed May 31, 2018, and U.S. Provisional Application Ser. No. 62/535,490, filed Jul. 21, 2017, the contents of which applications are specifically incorporated herein by reference in their entireties.

GOVERNMENT FUNDING

This invention was made with government support under grant number DK060771 by the National Institutes of Health. The government has certain rights in the invention.

BACKGROUND

Although chemotherapy has been useful to prolong survival, to reduce the amount of tissue surgically removed, and to increase remission rates for some cancer types, cancers such as breast, lung and colorectal carcinomas still have high mortality rates and account for the majority of cancer deaths. This is true despite major changes in surgical and radiation protocols including combinatorial drug and drug-radiation regimens and new approaches to the staging of treatments. Another problem with many currently available chemotherapeutic agents is their toxicity. For example, some kinase inhibitors are being developed for cancer treatment but administration of those inhibitors typically causes negative side effects. In another example, chemotherapy has been combined with immune-based therapies that are designed to induce anti-cancer T-cell activity, but such an approach is often compromised by the immunosuppressive effect of the chemotherapy, which can suppress formation of cancer-specific T-cells. Other anti-cancer agents may provide treatment of certain types of cancers or certain types of patients but exhibit little or no widespread efficacy for other cancer types and patient populations.

Thus, there is a need for less toxic anti-cancer agents that can effectively treat a variety of cancer types and patient populations.

SUMMARY

The invention relates compositions and methods that can inhibit cancer cell adhesion and/or metastasis by inhibiting interactions between AKT (or protein kinase B) and focal adhesion kinase (FAK). The compositions and methods can involve use of peptide inhibitors, small molecules, and combinations thereof. Such inhibition specifically inhibits a metastasis-promoting pathway without interfering with other functions of AKT and FAK. Administration of the inhibitors and compositions disclosed herein can have less negative side effects and less toxicity than currently available chemotherapeutic agents.

DESCRIPTION OF THE FIGURES

FIG. 4A illustrates recombinant GST-FAK truncated peptides NT1 (residues 1-126; SEQ ID NO:3), NT1-1 (residues 1-60), NT1-2 (residues 61-126), NT1-1-2-1 (residues 61-93), and NT1-2-2 (residues 94-126; SEQ ID NO:2) that were generated and tested for their ability to pull down Akt1. FIG. 4B-4C show that all truncated peptides containing the NT1-2-2 region (NT1, NT1-2, and NT1-2-2) pulled down Akt1 in a pull-down assay. The constructs that did not contain the NT1-2-2 region (GST, NT1-1, and NT1-2-1) pulled down a significantly smaller amount of Akt1 (N=4; *$p<0.05$ vs GST control; #$p<0.05$ vs GST-NT1-1; ^$p<0.05$ vs GST-NT1-2-1).

FIG. 5A-5B schematically illustrate the structure of the FAK molecule. FIG. 5 schematically illustrates the crystal structure of the FAK FERM domain containing the F1 (purple/blue/cyan in the original), F2 (orange in the original), and F3 (green in the original) lobes (PDB code: 2AL6). FIG. 5B shows the surface of the crystal structure of the FAK FERM domain containing the F1 (purple/blue/cyan in the original), F2 (orange in the original), and F3 (green in the original) lobes (PDB code: 2AL6). The NT1-2-2 (SEQ ID NO:2) segment is shown in blue in the original with its surface accessible region highlighted in cyan in the original.

FIG. 6A illustrates that GST-FAK-NT1 conjugated beads pulled down purified Akt1 (N=3). The western blot shows the amount of Akt1 (prey, 60 kDa) signal relative to the amount of GST-FAK-NT1 (bait, estimated 35 kDa) signal. FIG. 6B shows an image of a western blot illustrating the amount of Akt1 (prey) signal relative to the amount of GST-FAK-NT1 or FAK mutant (bait) signal. Western blots were probed for Akt1 (top) and GST (bottom). A marker (M) and the amount of Akt1 signal produced by 40 µg of SW620 whole cell lysate control were used as a reference. FIG. 6C graphically illustrates densitometric data analyzed as the percentage of Akt1 signal over GST fusion protein signal, which was then normalized to the wild-type NT1 (n=8-19, * $p<0.05$ vs. the GST-FAK NT1 wild-type). FIG. 6D shows the amino acid sequence of the NT1-2-2 peptide (SEQ ID NO:2) with corresponding secondary structures; the β-helices are shown in green in the original, the α-helix in gray in the original, and the short helix in cyan in the original. The schematic diagram of the secondary structures present in each truncation correspond to the constructs found in the table to the left. FIG. 6E shows an image of a western blot illustrating the amount of Akt1 (prey) signal relative to the amount of GST/GST-FAK truncation (bait) signal. The low molecular weight of the truncations impedes the differentiation between GST-FAK truncations and unbound GST tags. Western blots were probed for Akt1 (top) and GST (bottom). A marker (M) and the amount of Akt1 signal produced by 40 μg of SW620 whole cell lysate control were used as a reference. FIG. 6F graphically illustrates densitometric data provided as the percentage of Akt1 signal over GST fusion protein signal and then normalized to the Akt1 pulldown from the NT1-2-2 (SEQ ID NO:2) construct. All truncations pulled down significantly more Akt1 than did the GST control (n=6, * p<0.05 vs. GST).

FIG. 7A shows an image of a western blot illustrating the amount of Akt1 (60 kDa) signal relative to the amount of GST (25 kDa)/GST-FAK-NT1 (estimated 35 kDa) signal, along with a marker (M) and the amount of Akt1 signal produced by 40 μg of SW620 whole cell lysate control as a references. Treatments indicated refer to the interfering peptide or vehicle (water) used. Western blots from the Akt1 pulldown assays were probed for Akt1 (top) and GST (bottom). FIG. 7B graphically illustrates that treatment with the wild-type 33 amino acid peptide (Pep-FAK-NT1-2-2; SEQ ID NO:2) reduced the amount of Akt1 pulled down by GST-FAK-NT1 vs. vehicle control treatment, while the scrambled peptide (Pep-FAK-NT1-2-2Scr) did not reduce Akt1 pull-down (n=4, * p<0.05 vs. vehicle-treated GST-FAK-NT1). FIG. 7C illustrates that use of GST-FAK as bait with interfering peptides 7 amino acids in length decreased Akt1 pulldown coinciding with the addition of wild type or mutant FAK peptides. The GST-probed western (bottom) shows more bands indicating that the full-length GST-FAK (150 kDa) yields more break down products. FIG. 7D graphically illustrates that incubation with the wild-type (LAHPPEE, SEQ ID NO:1) or mutant (LAHPSEE, SEQ ID NO:17 and AAHCGEE, SEQ ID NO:19) peptides reduced Akt1 pulldown when compared to the vehicle control. No such effect was seen after incubation with the scrambled short helix control (HPELAPE, SEQ ID NO:23) or the β-strand control (WKYELRI; SEQ ID NO:26) (n=12-14, * p<0.05 vs. vehicle treated GST-FAK). All peptides were used at a concentration of 160 μM.

FIG. 7E illustrates a ribbon diagram of the structure of the FAK FERM domain containing the F1 (magenta, green and blue in the original), F2 (orange in the original), and F3 (yellow in the original) lobes (from PDB entry 2AL6 (31)), rendered by PyMOL (v. 1.8.2.2; Schrodinger LLC, NY). FIG. 7F illustrates a surface diagram of the structure of the FAK FERM domain containing the F1 (magenta, green and blue in the original), F2 (orange in the original), and F3 (yellow in the original) lobes (from PDB entry 2AL6 (31)), rendered by PyMOL (v. 1.8.2.2; Schrodinger LLC, NY). The NT1-2-2 segment (SEQ ID NO:2) is colored as shown in FIG. 6D, with β4 and β5 in green in the original, α2 in pale blue in the original, and the short PPE helix in dark blue in the original. FIG. 7G shows a close-up of the FAK NT1-2-2 (SEQ ID NO:2) peptide region based on the crystal structure of chicken FAK, which is highly similar in sequence. β4 and β5 appear in green in the original, α2 is in gray (left) in the original, and the epitope formed by the short PPE helix is in dark blue in the original (upper left). Relative to FIG. 7E and FIG. 7F, the view in FIG. 7G is rotated by 180° about the z-axis (perpendicular to the plane of the page), to better view the LAHPPEE epitope (SEQ ID NO:1, residues 113-117).

FIG. 8A-8F illustrate the effects of a FAK-derived peptide on pressure-stimulated signaling in intact cells. FIG. 8A shows images of two western blots. The top set of western blots shows phospho-FAK (pFAK, Tyr397), phospho-Akt1 (pAkt1, Ser473), and phospho-GSK-3β (pGSK3B, Ser9) signals while the bottom set shows signals for total FAK, Akt1, and GSK3B. In each set, the blots were cut at the level of 75 kD as determined by a protein standard marker (M), and the higher weight bands were incubated with pFAK/FAK (125 kDa) antibodies while the lower weight bands received pAkt1/Akt1 (60 kDa) and pGSK3B/GSK3B (46 kDa) probes. Samples were grouped by Ad-FAK-HelixScr (expressing HPELAPE, SEQ ID NO:23) or the Ad-FAK-Helix (expressing LAHPPEE, SEQ ID NO:1) infection and then subdivided by exposure to ambient pressure (A), 15 mmHg pressure (P), or cell adhesion (Adh) conditions. FIG. 8B graphically illustrates that suspended Ad-FAK-HelixScr cells exposed to pressure exhibited increased FAK Tyr397 vs. those exposed to ambient atmosphere. However, pressure did not affect FAK Tyr397 phosphorylation in suspended Ad-FAK-Helix cells. In contrast, adhesion increased FAK Tyr397 phosphorylation compared to suspended cells at ambient pressure in both Ad-FAK-HelixScr and Ad-FAK-Helix infected cells. FIG. 8C graphically illustrates that both Ad-FAK-HelixScr and Ad-FAK-Helix virus infected cells exhibited increased Akt1 Ser473 phosphorylation after exposure to 15 mmHg pressure as well as after adhesion. FIG. 8D shows that GSK-3β Ser9 phosphorylation also increased in both the Ad-FAK-HelixScr and the Ad-FAK-Helix virus treated cells in response to adhesion (n=4-8, * p<0.05 vs. ambient Ad-FAK-HelixScr, #p<0.05 vs. 15 mmHg Ad-FAK-HelixScr). FIG. 8E shows that the initial probe for HA/HA-FAK coimmunoprecipitated Akt1 to produce a western signal which was normalized to the respective amount of FAK signal. The top western blot was probed for Akt1 while the bottom blot was probed for FAK. The samples are first grouped by viral infection, uninfected (Control), Ad-FAK-HelixScr, or Ad-FAK-Helix, and then subdivided by exposure to ambient pressure (A) or 15 mmHg pressure (P). All cells were transfected with HA-FAK except the HA-Ctrl cells which were transfected with a plasmid expressing the HA tag alone. All samples were first incubated with anti-HA antibody to precipitate HA-fusion proteins except for the IgG sample which used a general anti-IgG antibody. A marker (M) and 40 μg of SW620 whole cell lysate were used as a references for Akt1 (60 kDa) and FAK (125 kDa). FIG. 8F graphically illustrates that exposure to pressure increased Akt1 coimmunoprecipitation in control SW620 cells or cells infected with Ad-FAK-HelixScr. Pressure did not increase Akt1 coimmunoprecipitation in SW620 cells infected with Ad-FAK-Helix (n=6, * p<0.05 vs. ambient pressure, #p<0.05 vs. 15 mmHg Ad-FAK-HelixScr).

FIG. 9A-9B graphically illustrate that FAK-derived peptides block pressure stimulation of adhesion but not pressure stimulation of proliferation. FIG. 9A shows that exposure to elevated pressure increased adhesion by SW620 cells infected with the Ad-FAK-HelixScr (expressing HPELAPE, SEQ ID NO:23) virus vs. ambient pressure. Adhesion by cells infected with the Ad-FAK-Helix virus (expressing LAHPPEE, SEQ ID NO:1) did not change in response to increased pressure and was not different at ambient pressure from the adhesion of cells infected with Ad-FAK-HelixScr at ambient pressure. (n=8, * p<0.05 vs. the paired ambient pressure group, #p<0.05 vs. 15 mmHg Ad-FAK-HelixScr). FIG. 9B shows that in adherent cells, exposure to increased pressure stimulated cell proliferation in control (uninfected), Ad-FAK-HelixScr infected, and Ad-FAK-Helix infected SW620 cells (n=4, * p<0.05 vs. the paired ambient pressure group).

FIG. 11A shows the tumor-free survival percentage of animals with palpable tumors. FIG. 11B shows the tumor-free survival percentage of animals with tumors that were greater than 500 mg in weight. The Kaplan-Meier graphs document palpable tumor development and population survival (as represented by the absence of tumors 500 mg in mass) over time. The data were analyzed by Mantel-Haenszel testing. The symbol * indicates p<0.05 vs Ad-FAK-HelixScr infected ambient pressure control.

FIG. 12A graphically illustrates inhibition of cellular adhesion by compound 5. FIG. 12B shows images of western blots of cellular proteins after incubation of cells with compound 5 (D5) or DMSO (control) either at ambient pressure (A) or at 15 mmHg pressure (P). The top western blot shows phospho-FAK (pFAK, Y397), phospho-Akt1 (pAkt1, Ser473). The second western blot from the top shows total FAK. The third western blot from the top shows the amounts of pAkt1 S473. The bottom western blot shows amounts of Akt1. In each set, the blots were cut at the level of 75 kD as determined by a protein standard marker (M), and the higher weight bands were incubated with pFAK/FAK (125 kDa) antibodies while the lower weight bands received pAkt1/Akt1 (60 kDa) robes. Samples containing compound 5 or DMSO (control) were treated by exposure to ambient pressure (A), or 15 mmHg pressure (P). FIG. 12C graphically illustrates inhibition of pressure-induced FAK phosphorylation by compound 5 as evaluated by densitometric data and plotted as the percentage of phosphorylated FAK over non-phosphorylated FAK. FIG. 12D graphically illustrates that compound 5 does not inhibit pressure-induced phosphorylation of Akt1 at serine 473.

FIG. 14A shows a molecular structure of the AAHPSEE peptidyl epitope (SEQ ID NO:24) used for screening (sticks), shown in place of the wild-type residues 113-119, LAHPPEE (SEQ ID NO:1), of the FAK FERM domain (blue surface; PDB entry 2a16). FIG. 14B shows a structure of AHHPSEE (SEQ ID NO:24; carbons in green in the original) overlaid with ZINC04085549 (carbons in aqua in the original), rotated by ~90° around the z-axis relative to the view in FIG. 14A. FIG. 14C shows a 2D structure of ZINC04085549 with some identifiers.

FIG. 15A shows western blots probed for FAK-Tyr-397 phosphorylation or total FAK (which served as a loading control) after SW620 cells were treated with 0.1% DMSO as a vehicle control or 1-100 pM ZINC31501681 and subjected to ambient pressure (P) or for 15 mmHg increased pressure (P) for 30 minutes. FIG. 15B graphically illustrates densitometric quantitation of pFAKY397/FAK from five independent experiments. (* denotes p≤0.05 for comparison between 0.1% DMSO ambient and pressure while #denotes p≤0.05 for comparisons between 0.1% DMSO and 1-100 pM ZINC31501681 at ambient pressure.)

FIG. 16A shows the ZINC04085549 compound selected from ROCS overlays with AAHPSEE (SEQ ID NO:24). FIG. 16B the ZINC02457454 compound selected from ROCS overlays with AAHPSEE (SEQ ID NO:24). FIG. 16C shows the ZINC04085550 compound identified via ZINC 2D-Tanimoto similarity search (*) using ZINC04085549 from FIG. 16A as the query. FIG. 16D shows the ZINC12960430 compound identified via ZINC 2D-Tanimoto similarity search (*) using ZINC04085549 from FIG. 16A as the query. FIG. 16E shows the ZINC4085554 compound identified via a SwissSimilarity electroshape search () using ZINC04085549 from FIG. 16A as the query. FIG. 16F shows the ZINC6241139 compound identified via a SwissSimilarity electroshape search () using ZINC04085549 from FIG. 16A as the query. FIG. 16G shows the ZINC5816335 compound identified via a SwissSimilarity electroshape search (**) using ZINC04085549 from FIG. 16A as the query.

FIG. 17A shows the ZINC31501681 compound. FIG. 17B shows the ZINC58264388 compound. FIG. 17C shows the ZINC40099027 compound. FIG. 17D shows the ZINC25613745 compound.

FIG. 19A shows representative blots probed for FAK-Tyr-397 phosphorylation and total FAK. FIG. 19B summarizes densitometric quantitation of pFAKY397/FAK from five independent experiments. (*p<0.05)

DETAILED DESCRIPTION

Figure 1:
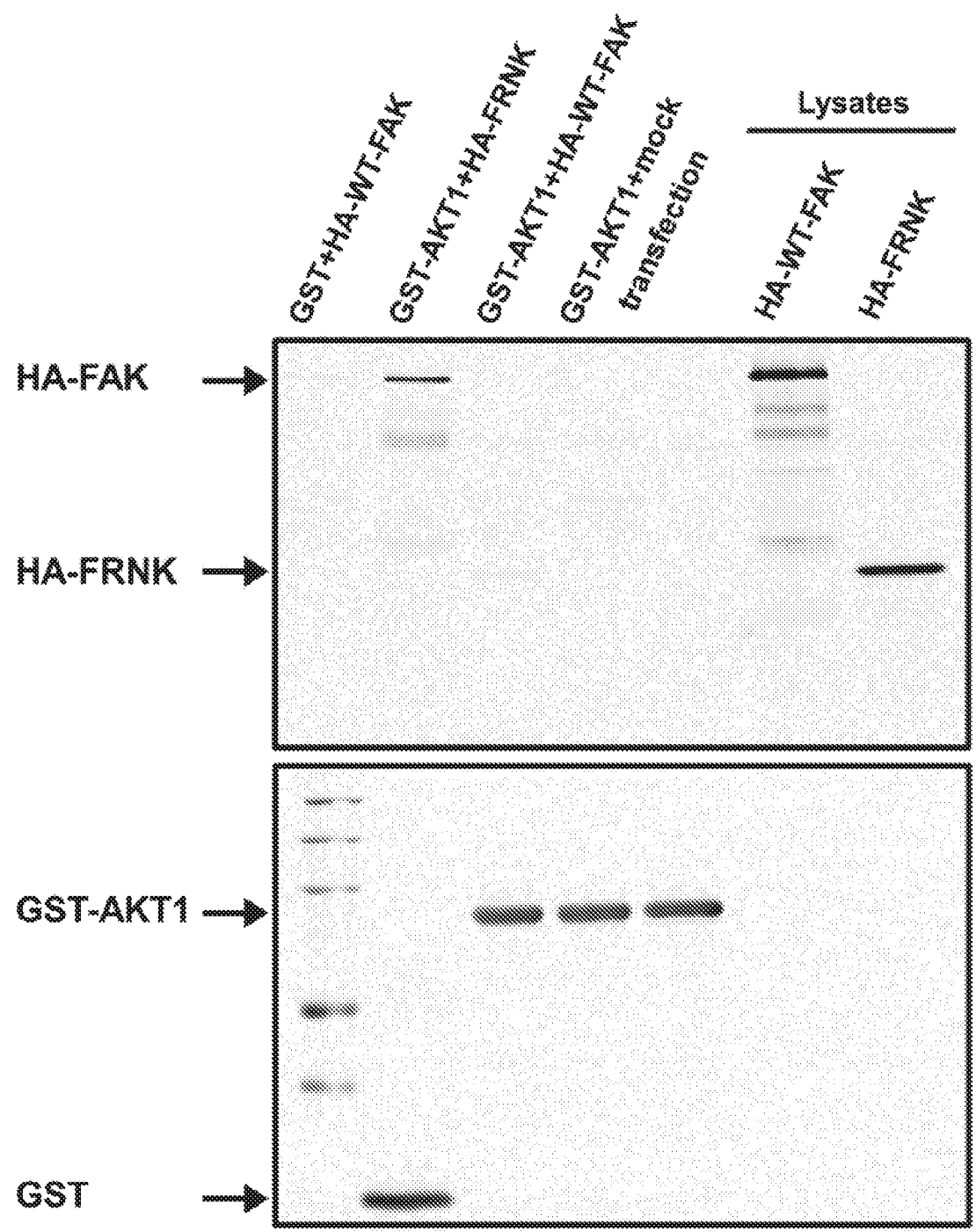
FIG. 1 illustrates that the FRNK polypeptide alone is not sufficient to bind Akt1. FRNK (FAK-related non-kinase, 67 kDa) is a segment from the COOH-terminal region of the FAK molecule, the C-terminal Focal Adhesion Targeting domain, which functions as an endogenous FAK inhibitor by competitively binding to focal contacts while lacking catalytic capability. Pull-down assays used GST or GST-Akt1 (prey, bottom blot) to bind human influenza hemagglutinin (HA) tagged FRNK (HA-FRNK) or HA-tagged wild type FAK (HA-WT-FAK; bait, top blot) found in the cell lysate of transiently transfected Caco-2 cells. Caco-2 cells expressing HA-FRNK control showed low levels of GST-Akt1 pull-down relative to those expressing HA-WT-FAK (one of two similar blots is shown). Lysate from cells transfected with HA-WT-FAK or HA-FRNK were used as references.

Methods and compositions are described herein that include use of inhibitors of Akt1/FAK binding. As described herein, cancer cell adhesion or metastasis can be inhibited by inhibiting interactions between AKT (or protein kinase B) and focal adhesion kinase (FAK).

Peptide Inhibitors

Peptide fragments of the FAK protein are effective inhibitors of Akt1/FAK interaction. For example, peptides that include an amino acid sequence as short as seven amino acids (LAHPPEE, SEQ ID NO:1) In some cases, longer peptides can be used such as the NT1-2-2 and NT1 peptides, with SEQ ID NO:2 and 3 respectively, to inhibit cancer cell adhesion or metastasis by inhibiting interactions between AKT and FAK. Rather than mediating cell adhesion and cancer cell metastasis, as does the full length FAK protein, peptide fragments from specific regions of FAK have the opposite effect. The peptide fragments of FAK are surprisingly effective inhibitors of cancer cell adhesion and cancer cell metastasis.

NT1-2-2:
(SEQ ID NO: 2)
EVHWVHLDMG VSSVREKYEL AHPPEEWKYE LRI

NT1:
(SEQ ID NO: 3)
  1 MAAAYLDPNL NHTPNSSTKT HLGTGMERSP GAMERVLKVF

41 HYFESNSEPT TWASIIRHGD ATDVRGIIQK IVDSHKVKNV

81 ACYGFRLSHL RSEEVHWLHV DMGVSSVREK YELAHPPEEW

121 KYELRI

A series of truncation and molecular biology techniques were used to identify the SEQ ID NO:1-3 peptides derived from FAK. The NT1-2-2 peptide (SEQ ID NO:2) binds to AKT. The bigger 126 amino acid peptide that includes the SEQ ID NO:2 peptide is referred to as NT1 peptide (SEQ ID NO:3), which also binds to AKT. Both can be used to inhibit interaction of AKT and FAK. Other peptides that include the seven-amino acid sequence LAHPPEE (SEQ ID NO:1) also inhibit FAK/Akt1 interactions and are useful FAK/Akt1 interaction inhibitors.

AKT (or protein kinase B) and focal adhesion kinase (FAK) are kinases. The inventors have shown that AKT and FAK regulate various cellular functions (Wang & Basson, *Anticancer Agents Med Chem* 11: 993-1002 (2011)). FAK is an upstream regulator of AKT signaling pathway in various cancer cell lines and in xenograft tumor models. However, the inventors have shown that AKT can also directly regulate FAK by serine phosphorylation, and if AKT does not phosphorylate FAK, then FAK is not activated in the AKT signaling pathway and cancer cell adhesiveness is thus inhibited (Wang & Basson, *Am J Physiol Cell Physiol* 300: C657-670 (2011)).

The inventors have demonstrated that increases in extracellular pressure or shear stress activate an intracellular signal pathway that governs cancer cell adhesiveness in vitro for both cell lines and primary tumor cells from human patients. For example, AKT phosphorylation at serine 473 is stimulated by modest 15 mmHg extracellular pressure increase in colon cancer cells that only express Akt1 and Akt2. These studies indicate that AKT1 but generally not AKT2 is involved in the pathway (Thamilselvan et al. FASEB J. 21 (8):1730-41 (2007); Wang & Basson, Exp. Cell Res. 314:286-296 (2008); Wang & Basson, Cellular Oncology. 31(4):273-289 (2009); Perry et al. Am J Surg. 200(5): 610-14 (2010).

AKT is a serine/threonine (Ser/Thr) kinase with three isoforms (AKT1, AKT2, and AKT3) (Cheng et al. Oncogene 24: 7482-7492, 2005). FAK is a large protein with 1052 amino acids and 125 kDa molecular weight. The domain structure of FAK contains two major parts, i.e., N-terminus and C-terminus (e.g., FIG. 4A).

Sequences for various FAK proteins and genes can be a source of peptide inhibitors of interactions between AKT and FAK. Sequences for FAK are available from the National Center for Biotechnology Information (NCBI) database (see, e.g., the website at ncbi.nlm.nih.gov).

For example, an amino acid sequence for FAK1 isoform oo (*Homo sapiens*) is available as accession number NP 001339677.1, and is reproduced below as SEQ ID NO:4.

1 MAAAYLDPNL NHTPNSSTKT HLGTGMERSP GAMERVLKVF

41 HYFESNSEPT TWASIIRHGD ATDVRGIIQK IVDSHKVKHV

81 ACYGFRLSHL RSEEVHWLHV DMGVSSVREK YELAHPPEEW

121 KYELRIRYLP KGFLNQFTED KPTLNFFYQQ VKSDYMLEIA

161 DQVDQEIALK LGCLEIRRSY WEMRGNALEK KSNYEVLEKD

201 VGLKRFFPKS LLDSVKAKTL RKLIQQTFRQ FANLNREESI

241 LKFFEILSPV YRFDKECFKC ALGSSWIISV ELAIGPEEGI

281 SYLTDKGCNP THLADFTQVQ TIQYSNSEDK DRKGMLQLKI

321 AGAPEPLTVT APSLTIAENM ADLIDGYCRL VNGTSQSFII

361 RPQKEGERAL PSIPKLANSE KQGMRTHAVS VSDEISGDET

401 DDYAEIIDEE DTYTMPSKSY GIDEARDYEI QRERIELGRC

441 IGEGQFGDVH QGIYMSPENP ALAVAIKTCK NCTSDSVREK

481 FLQEACLKLP GDKDHVCFAH HSILSVLHST

The SEQ ID NO:2 region within the SEQ ID NO:4 FAK1 isoform is highlighted in bold and with underlining.

A cDNA that encodes the SEQ ID NO:4 FAK protein is available as accession number NM_001352748.1 and provided below a SEQ ID NO:5.

1 GCGCACGCGC GCGGGCCCGC GCCGACGCAG CACGGCCTCG

41 AGGGCGCGAG CCCGCGCCGC CGCCGCCGCC GCCGGTCCCG

81 GACCACTGTG AGCCCGCGGC GTGAGGCGTG GGAGGAAGCG

121 CGGCTGCTGT CGCCCAGCGC CGCCCCGTCG TCGTCTGCCT

161 TCGCTTCACG GCGCCGAGCC GCGGTCCGAA ATATGACAGA

201 TACCTAGCAT CTAGCAAAAT AATGGCAGCT GCTTACCTTG

241 ACCCCAACTT GAATCACACA CCAAATTCGA GTACTAAGAC

281 TCACCTGGGT ACTGGTATGG AACGTTCTCC TGGTGCAATG

321 GAGCGAGTAT TAAAGGTCTT TCATTATTTT GAAAGCAATA

361 GTGAGCCAAC CACCTGGGCC AGTATTATCA GGCATGGAGA

```
-continued
 401  TGCTACTGAT GTCAGGGGCA TCATTCAGAA GATAGTGGAC
 441  AGTCACAAAG TAAAGCATGT GGCCTGCTAT GGATTCCGCC
 481  TCAGTCACCT GCGGTCAGAG GAGGTTCACT GGCTTCACGT
 521  GGATATGGGC GTCTCCAGTG TGAGGGAGAA GTATGAGCTT
 561  GCTCACCCAC CAGAGGAGTG GAAATATGAA TTGAGAATTC
 601  GTTATTTGCC AAAAGGATTT CTAAACCAGT TTACTGAAGA
 641  TAAGCCAACT TTGAATTTCT TCTATCAACA GGTGAAGAGC
 681  GATTATATGT TAGAGATAGC TGATCAAGTG GACCAGGAAA
 721  TTGCTTTGAA GTTGGGTTGT CTAGAAATAC GGCGATCATA
 761  CTGGGAGATG CGGGGCAATG CACTAGAAAA GAAGTCTAAC
 801  TATGAAGTAT TAGAAAAGGA TGTTGGTTTA AAGCGATTTT
 841  TTCCTAAGAG TTTACTGGAT TCTGTCAAGG CCAAAACACT
 881  AAGAAAACTG ATCCAACAAA CATTTAGACA ATTTGCCAAC
 921  CTTAATAGAG AAGAAAGTAT TCTGAAATTC TTTGAGATCC
 961  TGTCTCCAGT CTACAGATTT GATAAGGAAT GCTTCAAGTG
1001  TGCTCTTGGT TCAAGCTGGA TTATTTCAGT GGAACTGGCA
1041  ATCGGCCCAG AAGAAGGAAT CAGTTACCTA ACGGACAAGG
1081  GCTGCAATCC CACACATCTT GCTGACTTCA CTCAAGTGCA
1121  AACCATTCAG TATTCAAACA GTGAAGACAA GGACAGAAAA
1161  GGAATGCTAC AACTAAAAAT AGCAGGTGCA CCCGAGCCTC
1201  TGACAGTGAC GGCACCATCC CTAACCATTG CGGAGAATAT
1241  GGCTGACCTA ATAGATGGGT ACTGCCGGCT GGTGAATGGA
1281  ACCTCGCAGT CATTTATCAT CAGACCTCAG AAAGAAGGTG
1321  AACGGGCTTT GCCATCAATA CCAAAGTTGG CCAACAGCGA
1361  AAAGCAAGGC ATGCGGACAC ACGCCGTCTC TGTGTCAGAT
1401  GAAATTAGTG GGGACGAAAC AGATGATTAT GCTGAGATTA
1441  TAGATGAAGA AGATACTTAC ACCATGCCCT CAAAAAGCTA
1481  TGGAATAGAT GAAGCCAGGG ATTATGAGAT TCAAAGAGAA
1521  AGAATAGAAC TTGGACGATG TATTGGAGAA GGCCAATTTG
1561  GAGATGTACA TCAAGGCATT TATATGAGTC CAGAGAATCC
1601  AGCTTTGGCG GTTGCAATTA AAACATGTAA AAACTGTACT
1641  TCGGACAGCG TGAGAGAGAA ATTTCTTCAA GAAGCCTGCC
1681  TTAAGCTCCC TGGGGATAAG GACCATGTTT GTTTCGCTCA
1721  CCACTCCATA CTCAGTGTCC TGCACAGTAC TTGACACCTA
1761  GAGAACACCT GGTAGATGTT TGTCATTCTG GTGTCCTTCA
1801  TTATATGTGC ATCAAATGAA TGCCTTCTGT TTTCCATTGT
1841  AATAAATACC ACCCAACAGT CCAATAAATT AATAATTCAT
1881  AGAG
```

The amino acid sequence for FAK1 isoform b (*Homo sapiens*) is another example of a FAK1 protein (available as accession number NP 005598.3 and is reproduced below as SEQ ID NO:6.

```
   1  MISADCNLCL PEYDRYLASS KIMAAAYLDP NLNHTPNSST
  41  KTHLGTGMER SPGAMERVLK VFHYFESNSE PTTWASIIRH
  61  GDATDVRGII QKIVDSHKVK HVACYGFRLS HLRSEEVHWL
 121  HVDMGVSSVR EKYELAHPPE EWKYELRIRY LPKGFLNQFT
 161  EDKPTLNFFY QQVKSDYMLE IADQVDQEIA LKLGCLEIRR
 201  SYWEMRGNAL EKKSNYEVLE KDVGLKRFFP KSLLDSVKAK
 241  TLRKLIQQTF RQFANLNREE SILKFFEILS PVYRFDKECF
 281  KCALGSSWII SVELAIGPEE GISYLTDKGC NPTHLADFTQ
 321  VQTIQYSNSE DKDRKGMLQL KIAGAPEPLT VTAPSLTIAE
 361  NMADLIDGYC RLVNGTSQSF IIRPQKEGER ALPSIPKLAN
 401  SEKQGMRTHA VSVSETDDYA EIIDEEDTYT MPSTRDYEIQ
 441  RERIELGRCI GEGQFGDVHQ GIYMSPENPA LAVAIKTCKN
 481  CTSDSVREKF LQEALTMRQF DHPHIVKLIG VITENPVWII
 521  MELCTLGELR SFLQVRKYSL DLASLILYAY QLSTALAYLE
 561  SKRFVHRDIA ARNVLVSSND CVKLGDFGLS RYMEDSTYYK
 601  ASKGKLPIKW MAPESINFRR FTSASDVWMF GVCMWEILMH
 641  GVKPFQGVKN NDVIGRIENG ERLPMPPNCP PTLYSLMTKC
 681  WAYDPSRRPR FTELKAQLST ILEEEKAQQE ERMRMESRRQ
 721  ATVSWDSGGS DEAPPKPSRP GYPSPRSSEG FYPSPQHMVQ
 761  TNHYQVSGYP GSHGITAMAG SIYPGQASLL DQTDSWNHRP
 801  QEIAMWQPNV EDSTVLDLRG IGQVLPTHLM EERLIRQQQE
 841  MEEDQRWLEK EERFLKPDVR LSRGSIDRED GSLQGPIGNQ
 881  HIYQPVGKPD PAAPPKKPPR PGAPGHLGSL ASLSSPADSY
 921  NEGVKLQPQE ISPPPTANLD RSNDKVYENV TGLVKAVIEM
 961  SSKIQPAPPE EYVPMVKEVG LALRTLLATV DETIPLLPAS
1001  THREIEMAQK LLNSDLGELI NKMKLAQQYV MTSLQQEYKK
1041  QMLTAAHALA VDAKNLLDVI DQARLKMLGQ TRPH
```

The SEQ ID NO:2 region within the SEQ ID NO:6 FAK1 isoform is highlighted in bold and with underlining. Hence, the FAK peptide from the SEQ ID NO:6 protein that is analogous to the SEQ ID NO:2 FAK peptide inhibitor, has the following amino acid sequence (SEQ ID NO:7).

```
 96                                         EVHWL
121  HVDMGVSSVR EKYELAHPPE EWKYELRI
```

As is illustrated below, the FAK peptide inhibitors with SEQ ID NO:2 and SEQ ID NO:7 have similar but non-identical sequences (the differences are highlighted below in bold with underlining). Both peptides can be used as inhibitors of AKT and FAK interactions.

```
                                         (SEQ ID NO: 2)
EVHWVHLDMGVSSVREKYELAHPPEEWKYELRI.

(SEQ ID NO: 7)
EVHWLHVDMGVSSVREKYELAHPPEEWKYELRI.
```

A nucleic acid encoding the SEQ ID NO:6 FAK polypeptide is available in the NCBI database as accession number NM_005607.4, which is provided below as SEQ ID NO:8. The nucleic acid segment encoding the SEQ ID NO:7 FAK peptide is identified with highlighting in bold and underlining.

```
   1 GCGCACGCGC GCGGGCCCGC GCCGACGCAG CACGGCCTCG
  41 AGGGCGCGAG CCCGCGCCGC CGCCGCCGCC GCCGGTCCCG
  81 GACCACTGTG AGCCCGCGGC GTGAGGCGTG GGAGGAAGCG
 121 CGGCTGCTGT CGCCCAGCGC CGCCCCGTCG TCGTCTGCCT
 161 TCGCTTCACG GCGCCGAGCC GCGGTCCGAA GTCTTGCTGT
 201 GTCACCCAGG CTGCCAGGCT GGAGTGGAGT GGCATGATCT
 241 CGGCTGACTG CAACCTCTGC CTCCCAGAAT ATGACAGATA
 281 CCTAGCATCT AGCAAAATAA TGGCAGCTGC TTACCTTGAC
 321 CCCAACTTGA ATCACACACC AAATTCGAGT ACTAAGACTC
 361 ACCTGGGTAC TGGTATGGAA CGTTCTCCTG GTGCAATGGA
 401 GCGAGTATTA AAGGTCTTTC ATTATTTTGA AAGCAATAGT
 441 GAGCCAACCA CCTGGGCCAG TATTATCAGG CATGGAGATG
 481 CTACTGATGT CAGGGGCATC ATTCAGAAGA TAGTGGACAG
 521 TCACAAAGTA AAGCATGTGG CCTGCTATGG ATTCCGCCTC
 561 AGTCACCTGC GGTCAGAGGA GGTTCACTGG CTTCACGTGG
 601 ATATGGGCGT CTCCAGTGTG AGGGAGAAGT ATGAGCTTGC
 641 TCACCCACCA GAGGAGTGGA AATATGAATT GAGAATTCGT
 681 TATTTGCCAA AAGGATTTCT AAACCAGTTT ACTGAAGATA
 721 AGCCAACTTT GAATTTCTTC TATCAACAGG TGAAGAGCGA
 761 TTATATGTTA GAGATAGCTG ATCAAGTGGA CCAGGAAATT
 801 GCTTTGAAGT TGGGTTGTCT AGAAATACGG CGATCATACT
 841 GGGAGATGCG GGGCAATGCA CTAGAAAAGA AGTCTAACTA
 881 TGAAGTATTA GAAAAAGATG TTGGTTTAAA GCGATTTTTT
 921 CCTAAGAGTT TACTGGATTC TGTCAAGGCC AAAACACTAA
 961 GAAAACTGAT CCAACAAACA TTTAGACAAT TGCCAACCT
1001 TAATAGAGAA GAAAGTATTC TGAAATTCTT TGAGATCCTG
1041 TCTCCAGTCT ACAGATTTGA TAAGGAATGC TTCAAGTGTG
1081 CTCTTGGTTC AAGCTGGATT ATTTCAGTGG AACTGGCAAT
1121 CGGCCCAGAA GAAGGAATCA GTTACCTAAC GGACAAGGGC
1161 TGCAATCCCA CACATCTTGC TGACTTCACT CAAGTGCAAA
1201 CCATTCAGTA TTCAAACAGT GAAGACAAGG ACAGAAAAGG
1241 AATGCTACAA CTAAAAATAG CAGGTGCACC CGAGCCTCTG
1281 ACAGTGACGG CACCATCCCT AACCATTGCG GAGAATATGG
1321 CTGACCTAAT AGATGGGTAC TGCCGGCTGG TGAATGGAAC
1361 CTCGCAGTCA TTTATCATCA GACCTCAGAA AGAAGGTGAA
1401 CGGGCTTTGC CATCAATACC AAAGTTGGCC AACAGCGAAA
1441 AGCAAGGCAT GCGGACACAC GCCGTCTCTG TGTCAGAAAC
1481 AGATGATTAT GCTGAGATTA TAGATGAAGA AGATACTTAC
1521 ACCATGCCCT CAACCAGGGA TTATGAGATT CAAAGAGAAA
1561 GAATAGAACT TGGACGATGT ATTGGAGAAG GCCAATTTGG
1601 AGATGTACAT CAAGGCATTT ATATGAGTCC AGAGAATCCA
1641 GCTTTGGCGG TTGCAATTAA AACATGTAAA AACTGTACTT
1681 CGGACAGCGT GAGAGAGAAA TTTCTTCAAG AAGCCTTAAC
1721 AATGCGTCAG TTTGACCATC CTCATATTGT GAAGCTGATT
1761 GGAGTCATCA CAGAGAATCC TGTCTGGATA ATCATGGAGC
1801 TGTGCACACT TGGAGAGCTG AGGTCATTTT TGCAAGTAAG
1841 GAAATACAGT TTGGATCTAG CATCTTTGAT CCTGTATGCC
1881 TATCAGCTTA GTACAGCTCT TGCATATCTA GAGAGCAAAA
1921 GATTTGTACA CAGGGACATT GCTGCTCGGA ATGTTCTGGT
1961 GTCCTCAAAT GATTGTGTAA AATTAGGAGA CTTTGGATTA
2001 TCCCGATATA TGGAAGATAG TACTTACTAC AAAGCTTCCA
2041 AAGGAAAATT GCCTATTAAA TGGATGGCTC CAGAGTCAAT
2081 CAATTTTCGA CGTTTTACCT CAGCTAGTGA CGTATGGATG
2121 TTTGGTGTGT GTATGTGGGA GATACTGATG CATGGTGTGA
2161 AGCCTTTTCA AGGAGTGAAG AACAATGATG TAATCGGTCG
2201 AATTGAAAAT GGGGAAAGAT TACCAATGCC TCCAAATTGT
2241 CCTCCTACCC TCTACAGCCT TATGACGAAA TGCTGGGCCT
2281 ATGACCCCAG CAGGCGGCCC AGGTTTACTG AACTTAAAGC
2321 TCAGCTCAGC ACAATCCTGG AGGAAGAGAA GGCTCAGCAA
2361 GAAGAGCGCA TGAGGATGGA GTCCAGAAGA CAGGCCACAG
2401 TGTCCTGGGA CTCCGGAGGG TCTGATGAAG CACCGCCCAA
2441 GCCCAGCAGA CCGGGTTATC CCAGTCCGAG GTCCAGCGAA
2481 GGATTTTATC CCAGCCCACA GCACATGGTA CAAACCAATC
2521 ATTACCAGGT TTCTGGCTAC CCTGGTTCAC ATGGAATCAC
2561 AGCCATGGCT GGCAGCATCT ATCCAGGTCA GGCATCTCTT
2601 TTGGACCAAA CAGATTCATG GAATCATAGA CCTCAGGAGA
2641 TAGCAATGTG GCAGCCCAAT GTGGAGGACT CTACAGTATT
2681 GGACCTGCGA GGGATTGGGC AAGTGTTGCC AACCCATCTG
2721 ATGGAAGAGC GTCTAATCCG ACAGCAACAG GAAATGGAAG
2761 AAGATCAGCG CTGGCTGGAA AAAGAGGAAA GATTTCTGAA
2801 ACCTGATGTG AGACTCTCTC GAGGCAGTAT TGACAGGGAG
2841 GATGGAAGTC TTCAGGGTCC GATTGGAAAC CAACATATAT
2881 ATCAGCCTGT GGGTAAACCA GATCCTGCAG CTCCACCAAA
2921 GAAACCGCCT CGCCCTGGAG CTCCCGGTCA TCTGGGAAGC
2961 CTTGCCAGCC TCAGCAGCCC TGCTGACAGC TACAACGAGG
3001 GTGTCAAGCT TCAGCCCCAG GAAATCAGCC CCCCTCCTAC
3041 TGCCAACCTG GACCGGTCGA ATGATAAGGT GTACGAGAAT
```

-continued

```
3081 GTGACGGGCC TGGTGAAAGC TGTCATCGAG ATGTCCAGTA
3121 AAATCCAGCC AGCCCCACCA GAGGAGTATG TCCCTATGGT
3161 GAAGGAAGTC GGCTTGGCCC TGAGGACATT ATTGGCCACT
3201 GTGGATGAGA CCATTCCCCT CCTACCAGCC AGCACCCACC
3241 GAGAGATTGA GATGGCACAG AAGCTATTGA ACTCTGACCT
3281 GGGTGAGCTC ATCAACAAGA TGAAACTGGC CCAGCAGTAT
3321 GTCATGACCA GCCTCCAGCA AGAGTACAAA AAGCAAATGC
3361 TGACTGCTGC TCACGCCCTG GCTGTGGATG CCAAAAACTT
3401 ACTCGATGTC ATTGACCAAG CAAGACTGAA AATGCTTGGG
3441 CAGACGAGAC CACACTGAGC CTCCCCTAGG AGCACGTCTT
3481 GCTACCCTCT TTTGAAGATG TTCTCTAGCC TTCCACCAGC
3521 AGCGAGGAAT TAACCCTGTG TCCTCAGTCG CCAGCACTTA
3561 CAGCTCCAAC TTTTTTGAAT GACCATCTGG TTGAAAAATC
3601 TTTCTCATAT AAGTTTAACC ACACTTTGAT TTGGGTTCAT
3641 TTTTTGTTTT GTTTTTTTCA ATCATGATAT TCAGAAAAAT
3681 CCAGGATCCA AAATGTGGCG TTTTTCTAAG AATGAAAATT
3721 ATATGTAAGC TTTTAAGCAT CATGAAGAAC AATTTATGTT
3761 CACATTAAGA TACGTTCTAA AGGGGGATGG CCAAGGGGTG
3801 ACATCTTAAT TCCTAAACTA CCTTAGCTGC ATAGTGGAAG
3841 AGGAGAGCAT GAAGCAAAGA ATTCCAGGAA ACCCAAGAGG
3881 CTGAGAATTC TTTTGTCTAC CATAGAATTA TTATCCAGAC
3921 TGGAATTTTT GTTTGTTAGA ACACCCTTCA GTTGCAATAT
3961 GCTAATCCCA CTTTACAAAG AATATAAAAG CTATATTTTG
4001 AAGACTTGAG TTATTTCAGA AAAAACTACA GCCCTTTTTG
4041 TCTTACCTGC CTTTTACTTT CGTGTGGATA TGTGAAGCAT
4081 TGGGTCGGGA ACTAGCTGTA GAACACAACT AAAAACTCAT
4121 GTCTTTTTTC ACAGAATAAT GTGCCAGTTT TTTGTAGCAA
4161 TGTTATTTCT CTTGGAAGCA GAAATGCTTT GTACCAGAGC
4201 ACCTCCAAAC TGCATTGAGG AGAAGTTCCA GAACCATCCC
4241 CTTTTTCCAT TTTTATATAA TTTATAAAGA AAGATTAAAG
4281 CCATGTTGAC TATTTTACAG CCACTGGAGT TAACTAACCC
4321 TTCCTTGTAT CTGTCTTCCC AGGAGAGAAT GAAGCAAAC
4361 AGGAATTTGG TTTTCTTTTG ATGTCCAGTT ACACCATCCA
4441 TTCTGTTAAT TTTGAAAAAA TATACCCTCC CTTTAGTTTG
4441 TTGGGGGATA TAAATTATTC TCAGGAAGAA TATAATGAAC
4481 TGTACAGTTA CTTTGACCTA TTAAAAAGGT GTTACCAGTA
4521 AAGTTCTTGT TGTAATATCC TTAAAA
```

Thus, a nucleotide sequence for the SEQ ID NO:7 FAK peptide (from within the SEQ ID NO:6 sequence) is provided below as SEQ ID NO:9.

```
561                GA GGTTCACTGG CTTCACGTGG
601 ATATGGGCGT CTCCAGTGTG AGGGAGAAGT ATGAGCTTGC
641 TCACCCACCA GAGGAGTGGA AATATGAAT
```

Another amino acid sequences for FAK1 (*Homo sapiens*) is available as accession number NP 001339648.1, which is provided below as SEQ ID NO:10.

```
  1 MAAAYLDPNL NHTPNSSTKT HLGTGMERSP GAMERVLKVF
 41 HYFESNSEPT TWASIIRHGD ATDVRGIIQK IVDSHKVKHV
 81 ACYGFRLSHL RSEEVHWLHV DMGVSSVREK YELAHPPEEW
121 KYELRIRYLP KGFLNQFTED KPTLNFFYQQ VKSDYMLEIA
161 DQVDQEIALK LGCLEIRRSY WEMRGNALEK KSNYEVLEKD
201 VGLKRFFPKS LLDSVKAKTL RKLIQQTFRQ FANLNREESI
241 LKFFEILSPV YRFDKECFKC ALGSSWIISV ELAIGPEEGI
281 SYLTDKGCNP THLADFTQVQ TIQYSNSEDK DRKGMLQLKI
321 AGAPEPLTVT APSLTIAENM ADLIDGYCRL VNGTSQSFII
361 RPQKEGERAL PSIPKLANSE KQGMRTHAVS VSETDDYAEI
401 IDEEDTYTMP STRDYEIQRE RIELGRCIGE GQFGDVHQGI
441 YMSPENPALA VAIKTCKNCT SDSVREKFLQ EALTMRQFDH
481 PHIVKLIGVI TENPVWIIME LCTLGELRSF LQVRKYSLDL
521 ASLILYAYQL STALAYLESK RFVHRDIAAR NVLVSSNDCV
561 KLGDFGLSRY MEDSTYYKAS KGKLPIKWMA PESINFRRFT
601 SASDVWMFGV CMWEILMHGV KPFQGVKNND VIGRIENGER
641 LPMPPNCPPT LYSLMTKCWA YDPSRRPRFT ELKAQLSTIL
681 EEEKAQQEER MRMESRRQAT VSWDSGGSDE APPKPSRPGY
721 PSPRSSEGFY PSPQHMVQTN HYQVSGYPGS HGITAMAGSI
761 YPGQASLLDQ TDSWNHRPQE IAMWQPNVED STVLDLRGIG
801 QVLPTHLMEE RLIRQQQEME EDQRWLEKEE RFLKPDVRLS
841 RGSIDREDGS LQGPIGNQHI YQPVGKPDPA APPKKPPRPG
881 APGHLGSLAS LSSPADSYNE GVKPWRLQPQ EISPPPTANL
921 DRSNDKVYEN VTGLVKAVIE MSSKIQPAPP EEYVPMVKEV
961 GLALRTLLAT VDETIPLLPA STHREIEMAQ KLLNSDLGEL
1001 INKMKLAQQY VMTSLQQEYK KQMLTAAHAL AVDAKNLLDV
1041 IDQARLKMLG QTRPH
```

As illustrated by the highlighting in bold and underlined the SEQ ID NO:10 protein includes the SEQ ID NO:7 peptide sequence, which is homologous to the SEQ ID NO:2 sequence.

Another amino acid sequence for a protein related to FAK1 is the isoform FAK-De133 (*Homo sapiens*), which is available as accession number AHZ89389.1, which is provided below as SEQ ID NO:11.

```
  1 MAAAAYLDPN LNHTPNSSTK THLGTGMERS PGAMERVLKV
 41 FHYFESNSEP TTWASIIRHG DATDVRGIIQ KIVDSHKVKH
```

```
 81 VACYGFRLSH LRSEEVHWLH VDMGVSSVRE KYELAHPPEE

121 WKYELRIRYL PKGFLNQFTE DKPTLNFFYQ QVKSDYMLEI

161 ADQVDQEIAL KLGCLEIRRS YWEMRGNALE KKSNYEVLEK

201 DVGLKRFFPK SLLDSVKAKT LRKLIQQTFR QFANLNREES

241 ILKFFEILSP VYRFDKECFK CALGSSWIIS VELAIGPEEG

281 ISYLTDKGCN PTHLADFTQV QTIQYSNSED KDRKGMLQLK

321 IAGAPEPLTV TAPSLTIAEN MADLIDGYCR LVNGTSQSFI

361 IRPQKEGERA LPSIPKLANS EKQGMRTHAV SVSETDDYAE

401 IIDEEDTYTM PSTRDYEIQR ERIELGRCIG EGQFGDVHQG

441 IYMSPENPAL AVAIKTCKNC TSDSVREKFL QEALTMRQFD

481 HPHIVKLIGV ITENPVWIIM ELCTLGELRS FLQVRKYSLD

521 LASLILYAYQ LSTALAYLES KRFVHRDIAA RNVLVSSNDC

561 VKLGDFGLSR YMEDSTYYKA SKGKLPIKWM APESINFRRF

601 TSASDVWMFG VCMWEILMHG VKPFQGVKNN DVIGRIENGE

641 RLPMPPNCPP TLYSLMTKCW AYDPSRRPRF TELKAQLSTI

681 LEEEKAQQEE RMRMESRRQA TVSWDSGGSD EAPPKPSRPG

721 YPSPRSSEGF YPSPQHMVQT NHYQVSGYPG SHGITAMAGS

761 IYPGQASLLD QTDSWNHRPQ EIAMWQPNVE DSTVLDLRGI

801 GQVLPTHLME ERLIRQQQEM EEDQRWLEKE ERFLKPDVRL

841 SRGSIDREDG SLQGPIGNQH IYQPVGKPDP AAPPKKPPRP

881 GAPGHLGSLA SLSSPADSYN EGVKLQPQEI SPPPTANLDR

921 SNDKVYENVT GLVKAVIEMS SKIQPAPPEE YVPMVKIEMA

961 QKLLNSDLGE LINKMKLAQQ YVMTSLQQEY KKQMLTAAHA

1001 LAVDAKNLLD VIDQARLKML GQTRPH
```

As illustrated by the highlighting in bold and underlined the SEQ ID NO:11 protein includes the SEQ ID NO:7 peptide sequence.

Mutant and Related Sequences

The Examples describe peptides with various mutations. For example, the following types of mutations within the SEQ ID NO:1 peptide have been evaluated.

L113A: AAHPPEE (SEQ ID NO:12)—Enhanced a helical preference

P116N: LAHNPEE (SEQ ID NO:13)—Similar a helical, 0 turn preference in the PPE region, increased polarity P116C: LAHCPEE (SEQ ID NO:14)—Structurally labile, greater hydrophobicity P116G: LAHGPEE (SEQ ID NO:15)—Stronger turn preference, greater flexibility, less hydrophobicity P117K: LAHPKEE (SEQ ID NO:16)—Structurally labile, enhanced polarity P117S: LAHPSEE (SEQ ID NO:17)—More structurally labile and polar Triple mutant L113A, P116N, P117K: AAHNKEE (SEQ ID NO:18)—Enhanced helicity and polarity Triple mutant L113A, P116C, P117G: AAHCGEE (SEQ ID NO:19)—More structurally labile and hydrophobic Triple mutant: L113A, P116A, P117A: AAHAAEE (SEQ ID NO:20)—More helical and hydrophobic The Examples illustrate that peptides that include portions of the wild type FAK sequence (LAHPPEE, SEQ ID NO:1), as well as peptides that have mutant LAHPSEE (SEQ ID NO:17) and AAHCGEE (SEQ ID NO:19) sequences inhibit FAK/Akt1 interactions. Accordingly, FAK peptide sequences such as those described herein can be modified and can still act as inhibitors of FAK/Akt1 interactions.

For example, a mutant NT1 peptide that includes a LAHPSEE (SEQ ID NO:17) peptide sequence would have the following sequence (SEQ ID NO:21).

```
  1 MAAAYLDPNL NHTPNSSTKT HLGTGMERSP GAMERVLKVF

41 HYFESNSEPT TWASIIRHGD ATDVRGIIQK IVDSHKVKNV

81 ACYGFRLSHL RSEEVHWLHV DMGVSSVREK YELAHPSEEW

121 KYELRI
```

In another example, a mutant NT1 peptide that includes sequence AAHCGEE (SEQ ID NO:19) peptide sequence would have the following sequence (SEQ ID NO:22).

```
  1 MAAAYLDPNL NHTPNSSTKT HLGTGMERSP GAMERVLKVF

41 HYFESNSEPT TWASIIRHGD ATDVRGIIQK IVDSHKVKNV

81 ACYGFRLSHL RSEEVHWLHV DMGVSSVREK YEAAHCGEEW

121 KYELRI
```

Peptides and nucleic acids with at least 50% sequence identity to those described herein can readily be identified, isolated and used as inhibitors of interactions between AKT and FAK. In some cases, peptides and nucleic acids with at least 60%, or at least 70%, or at least 80%, or at least 90%, or at least 95%, or at least 97%, or at least 98%, or at least 99% sequence identity to those described herein can readily be identified, isolated and used as inhibitors of interactions between AKT and FAK. For example, related nucleic acids that encode or hybridize to FAK nucleic acids, or fragments thereof can be used to generate peptide inhibitors that reduce interactions between AKT and FAK. Similarly, the FAK peptide inhibitors described herein can be modified to include amino acid substitutions, deletions and additions.

FAK nucleic acids related to those described herein can be employed to identify or make FAK-related nucleic acids that encode peptide inhibitors useful for reducing interaction between FAK and AKT. For example, related nucleic acids can be isolated and identified by mutation of the SEQ ID NO:5, SEQ ID NO:8 and/or SEQ ID NO:9 nucleic acid sequences and/or by hybridization to DNA and/or RNA isolated from other species using the SEQ ID NO:5, SEQ ID NO:8 and/or SEQ ID NO:9 nucleic acids as probes. FAK amino acid sequences (e.g., SEQ ID NO:1, 2, 3, 4, 6, 7, 10, 11, 12-20, 21, and/or 22) can also be examined and used a basis for designing alternative FAK peptide inhibitors and FAK nucleic acids useful for making such inhibitors.

In some embodiments, FAK inhibitor peptides are provided or manufactured by recombinant expression from related FAK nucleic acids that selectively hybridize to any of the FAK nucleic acids described herein (e.g., SEQ ID NO:5, 8, and/or 9). The term "selectively hybridize" includes hybridization, under stringent hybridization conditions, of a nucleic acid sequence to a specified nucleic acid target sequence (e.g., SEQ ID NO:5, 8, and/or 9) to a detectably greater degree (e.g., at least 2-fold over background) than its hybridization to non-target nucleic acid sequences. Such selective hybridization substantially excludes non-target nucleic acids.

Related FAK nucleic acids sequences typically have about at least 40% sequence identity, or at least 50% sequence identity, or at least 60% sequence identity, or at least 70% sequence identity, or at least 75% sequence identity, or at least 80% sequence identity, or at least 85% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NO:5, SEQ ID NO:6, and/or SEQ ID NO:8. In some embodiments, a selectively hybridizing sequence has about at least about 80% sequence identity or complementarity with any of SEQ ID NO:5, SEQ ID NO:8, and/or SEQ ID NO:9.

In some embodiments, the nucleic acids used in the methods and that encode the peptides described herein can include fragments of FAK nucleic acids. For example, the nucleic acids of the invention include those with about 125 of the same nucleotides as any of the SEQ ID NO:5 and 8 sequences, or about 150 of the same nucleotides as any of the SEQ ID NO:5 and 8 sequences, or about 200 of the same nucleotides as any of the SEQ ID NO:5 and 8 sequences, or about 225 of the same nucleotides as any of the SEQ ID NO:5, and 9 sequences, or about 250 of the same nucleotides as any of the SEQ ID NO:5 and 8 sequences, or about 275 of the same nucleotides as any of the SEQ ID NO:5 and 8 sequences, or about 285 of the same nucleotides as any of the SEQ ID NO:5 and 8 sequences, or about 290 of the same nucleotides as any of the SEQ ID NO:5 and 8 sequences, or about 125-1100 of the same nucleotides as any of the SEQ NO:5 and 8 sequences. A shorter nucleic acid such as one with SEQ ID NO:9 can include about 90 of the same nucleotides as the SEQ ID NO:9 sequence, or about 85 of the same nucleotides as the SEQ ID NO:9 sequence, or about 80 of the same nucleotides as the SEQ ID NO:9 sequence, or about 75 of the same nucleotides as the SEQ ID NO:9 sequence, or about 70 of the same nucleotides as the SEQ ID NO:9 sequence, or about 65 of the same nucleotides as the SEQ ID NO:9 sequence, or about 60 of the same nucleotides as the SEQ ID NO:9 sequence, or about 60 of the same nucleotides as the SEQ ID NO:9 sequence, or about 55 of the same nucleotides as the SEQ NO:9 sequence. The identical nucleotides can be distributed throughout the nucleic acid, and need not be contiguous. For example, the nucleic acid sequence of a FAK nucleic acid can be optimized for expression in a host cell species by altering selected codons to encode the same amino acid but use nucleotide codons that are more easily 'read' by the transcription/translation machinery of a selected host cell species.

The FAK related peptides and nucleic acids encoding those peptides can have about 60% to about 99% sequence identity with any of the nucleic acid or peptide sequences described herein. Note that if a value of a variable that is necessarily an integer (e.g., the number of nucleotides or amino acids in a nucleic acid or protein), is described as a range, e.g., 80-99% sequence identity what is meant is that the value can be any integer between 80 and 99 inclusive, i.e., 80, 81, 82, 83, 84, 85, 86, 87, 88, 89, 90, 91, 92, 93, 94, 95, 96, 97, 98 or 99, or any range between 80 and 99 inclusive, e.g., 81-99%, 81-98%, 82-99%, etc. For example, the FAK related peptides and nucleic acids encoding those peptides can have about 95%, about 96%, about 97%, about 98%, or about 99% sequence identity with any of the nucleic acid or peptide sequences described herein.

In some embodiments, related nucleic acid hybridize to the nucleic acids described herein under "stringent conditions" or "stringent hybridization conditions." In other embodiments, an inhibitory nucleic acid can hybridize to the nucleic acids described herein under "stringent conditions" or "stringent hybridization conditions."

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be hybridized that have up to 100% complementarity to the probe or inhibitory nucleic acid (homologous probing). Alternatively, stringency conditions can be adjusted to allow some mismatching in sequences so that lower degrees of sequence similarity are detected (heterologous probing).

A probe for identifying and/or isolating a related nucleic acid can be approximately 15-90 nucleotides in length, but can vary greatly in length from about 17 nucleotides to equal to the entire length of the target sequence. In some embodiments, the probe is about 10-50 nucleotides in length, or about 15-50 nucleotides in length, or about 16-45 nucleotides in length, or about 18-25 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$$T_m = 81.5° C. + 16.6(\log M) + 0.41(\% GC) - 0.61(\% \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of the SEQ ID NO:5, 8, and 9 sequences.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application, high stringency is defined as a wash in 0.1×SSC, 0.1% SDS at 65° C. High stringency hybridization can include hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., followed by a wash in 0.1×SSC, 0.1% SDS at 65° C.

The following terms are used to describe the sequence relationships between two or more nucleic acids or nucleic acids or peptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., any of the SEQ ID NO:5, 8, and 9 nucleic acid sequences) or an amino acid sequence (e.g., any of the SEQ ID NO:1, 2, 3, 4, 6, 7, 10, 11, 12-20, 21, or 22 amino acid sequences). A reference sequence may be a subset or the entirety of a specified sequence. For example, a reference sequence may be a segment of a full-length cDNA or of a genomic DNA sequence, or the complete cDNA or complete genomic DNA sequence, or a domain of a peptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and peptide sequences. Generally, for nucleic acids, the comparison window is at least 16 contiguous nucleotides in length, and optionally can be 18, 20, 30, 40, 50, 70, 90 or more nucleotides. For amino acid sequences, the comparison window is at least about 10 amino acids, and can optionally be 14, 16, 18, 20, 25, 30 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 11, 12, 13, 15, or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

In some cases, the FAK peptides have at least one, or at least two, or at least three, or at least four amino acid difference(s) relative to any of the SEQ ID NO:1, 2, 3, 4, 6, 7, 10, 11, 12-20, 21, or 22 peptide sequences.

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

The terms "substantial identity" indicates that a nucleic acid, peptide or related nucleic acid comprises a sequence with between 55-100% sequence identity to a reference sequence, with at least 55% sequence identity, or at least 60%, or at least 70%, or at least 80%, or at least 90%, or at least 95%, or at least 96%, or at least 97%, or at least 98%, or at least 99% sequence identity or any percentage of range between 55-100% sequence identity relative to the reference sequence over a specified comparison window. Optimal alignment may be ascertained or conducted using the homology alignment algorithm of Needleman and Wunsch, supra.

An indication that two peptide sequences are substantially identical is that both peptides have similar activities. For example, when a peptide is related to the FAK peptide inhibitors described herein, that peptide can inhibit interactions between FAK and AKT.

In some embodiments, the peptide that is substantially identical to an FAK peptide with a SEQ ID NO:1, 2, 3, 4, 6, 7, 10, 11, 12-20, 21, or 22 sequence may not have exactly the same level of inhibitory activity as the FAK peptide with a SEQ ID NO:1, 2, 3, 4, 6, 7, 10, 11, 12-20, 21, or 22. Instead, the substantially identical peptide may exhibit greater or lesser levels of inhibitory activity than the FAK peptide with SEQ ID NO:1, 2, 3, 4, 6, 7, 10, 11, 12-20, 21, or 22, as measured by assays described herein or those available in the art. For example, the substantially identical peptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the inhibitory activity of a FAK peptide with SEQ ID NO:1, 2, 3, 4, 6, 7, 10, 11, 12-20, 21, or 22 sequence when measured by similar assay procedures.

Alternatively, substantial identity is present when second peptide is immunologically reactive with antibodies raised against the first peptide (e.g., a peptide with SEQ ID NO:1, 2, 3, 4, 6, 7, 10, 11, 12-20, 21, or 22 sequence). Thus, a peptide is substantially identical to a first peptide, for example, where the two peptides differ only by a conservative substitution. In addition, a peptide can be substantially identical to a first peptide when they differ by a non-conservative change if the epitope that the antibody recognizes is substantially identical. Peptides that are "substantially similar" share sequences as noted above except that some residue positions, which are not identical, may differ by conservative amino acid changes.

The FAK-related peptides of the present invention may include the first 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69-81, 82, 83, 84, 85, 86, 87, 88, 89, 90, 91, 92, 93, 94, 95, 96, 97, 98 and 99 N-terminal amino acid residues of a the SEQ ID NO:1, 2, 3, 4, 6, 7, 10, 11, 12-20, 21, or 22 sequences. The FAK-related peptides of the present invention may include the first 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69-81, 82, 83, 84, 85, 86, 87, 88, 89, 90, 91, 92, 93, 94, 95, 96, 97, 98 and 99 C-terminal amino acid residues of a the SEQ ID NO:1, 2, 3, 4, 6, 7, 10, 11, 12-20, 21, or 22 sequences.

Small Molecule Inhibitors of FAK/AKT Interactions

The interactions between FAK and AKT can be inhibited by small molecules. For example, a compound of formula I can be used as an inhibitor of interactions between FAK and AKT:

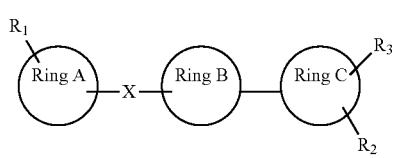

wherein:

Ring A and Ring C independently are each an aryl ring;

Ring B is a cycloalkyl ring;

$R_1$ is a hydrogen, lower alkyl or lower alkoxy;

X is a $C_1$ to $C_4$ alkyl linker comprising a carbonyl, a carboxylate, an amide, a carboxylate(amino), or an aminocarboxylate group or a =N—O—SO$_2$— linker; and $R_2$ and $R_3$ are independently each a carboxylate, an amide, or a nitro group.

Aryl groups are cyclic aromatic hydrocarbons that do not contain heteroatoms. An aryl group can have about five to about fourteen ring atoms in which at least one ring is aromatic. Examples include a phenyl ring, a bicyclic ring (e.g., biphenyl), or tricyclic ring. Bicyclic and tricyclic rings can be ortho-fused but, as used herein, the bicyclic and tricyclic rings need not be fused and can be separate rings linked together by a covalent bond or a short alkyl (e.g.

$C_1$-$C_3$ alkyl). Examples of aromatic groups include groups such as benzene, phenyl, biphenyl, naphthalene, anthracene, or a combination thereof.

Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Alkyl groups include straight chain and branched alkyl groups and cycloalkyl groups having from 1 to about 20 carbon atoms, or from 1 to 12 carbons, or from 1 to 8 carbons, or, in some embodiments, from 1 to 6 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Lower alkyl groups have about 1 to 4 carbon atoms, or about 1 to about 3 carbon atoms.

In some cases, the Ring A and Ring C groups are phenyl or naphthyl groups.

In some cases, the Ring B group is a $C_1$ to $C_8$ cycloalkyl, or a $C_1$ to $C_6$ cycloalkyl.

In some cases, the X group is a three to four atom linker, where atoms can include one or more carbon, oxygen, and nitrogen atoms, and where the carbon and/or nitrogen atoms can be substituted with an alkyl or an oxy group. In some cases, the X group is a three atom linker, where atoms are one carbon, one oxygen, and one nitrogen atom. In some cases, the X group includes a carbonyl.

In some cases, the $R_2$ and $R_3$ groups are independently a carboxylate, or a nitro group. For example, the $R_2$ and $R_3$ groups can both be nitro groups.

All chiral, diastereomeric, racemic forms of a structure are intended to be embraced by the claims, unless the specific stereochemistry or isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

Examples of compounds or small molecules that inhibits interactions between FAK and AKT are shown below.

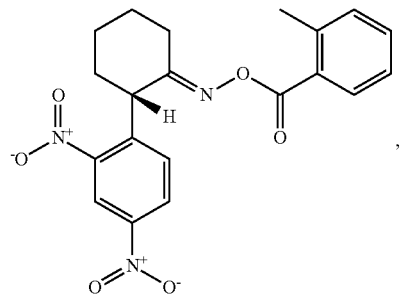

,

-continued

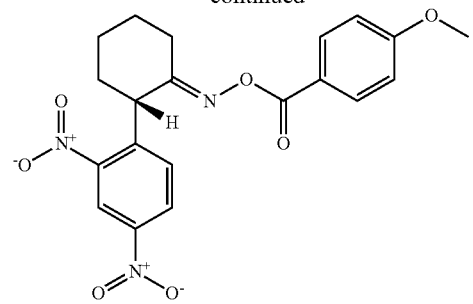

Methods

As illustrated herein, inhibitors of FAK/Akt1 interactions can significantly reduce cancer cell adhesion, which is a critical step for cancer metastasis. At least two different experimental approaches demonstrate that such inhibitors prevent extracellular pressure-stimulated cancer cell adhesion. The inventors have also shown that this increased cancer cell adhesiveness translates to substantial differences in survival in animal models.

One aspect of the invention is a method that includes administering to the mammal an inhibitor of FAK/Akt1 interactions. The mammal so treated can be in need of such administration. Inhibitors of Akt1 and FAK interaction can decrease such FAK/Akt1 interactions by at least 2%, or 5%, or 10%, or 15%, or 20%, or 25%, or 30%, or 35%, or 40%, or 45%, or 50%, or 55%, or 60%, or 65%, or %70, or 80%, or 90%, 095%, or 9'7%, or 99%, or any numerical percentage between 5% and 100%.

Such methods can thereby inhibit cancer cell adhesion in the mammal. Inhibiting cancer cell adhesion can also inhibit metastasis of cancer cells. As illustrated herein, inhibitors of Akt1 and FAK interaction can inhibit cancer cell adhesion by 10% to 50%. In some embodiments, peptide inhibitors of Akt1 and FAK interaction can decrease cancer cell adhesion and/or metastasis by at least 2%, or 5%, or 10%, or 15%, or 20%, or 25%, or 30%, or 35%, or 40%, or 45%, or 50%, or 55%, or 60%, or 65%, or %'70, or 80%, or 90%, 095%, or 97%, or 99%, or any numerical percentage between 5% and 100%.

The peptide inhibitors of AKT and FAK interactions can have about 80%, or 85%, or 90%, or 91%, or 92%, or 93%, or 94%, or 95%, or 96%, or 97%, or 98%, or 99% sequence identity to any of SEQ ID NO:1, 2, 3, 4, 6, 7, 10, 11, 12-20, 21, 22, or any combination thereof.

The methods and compositions described herein can be used to treat a variety of cancers and tumors, for example, colon cancer, intestinal cancer, leukemia, sarcoma, osteosarcoma, lymphomas, melanoma, glioma, pheochromocytoma, hepatoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or liver cancer, and cancer at an unknown primary site.

Extracellular forces like pressure and shear stress increase the binding affinity of surface integrins effectively decreasing the ligand threshold required for cell adhesion. Pressure stimulation provides dislodged tumor cells with such a metastatic advantage through a mechanism that involves elements such as FAK, Akt1, and Src. Common signaling components, these kinases are well-defined pharmacologic targets but also essential to normal cell physiology. However, the relationship between FAK and Akt1 presents an opportunity to interfere with this protein-protein interaction without compromising other catalytic potentials of these kinases. A previous preliminary study indicated that the FAK F1 lobe can by itself associate with Akt1. Here we demonstrate that overexpression of this FAK domain can itself inhibit pressure-induced adhesion. While the FAK F1 lobe itself is still quite large, and serial truncations demonstrated that the interaction between FAK and Akt1 depends upon a 33-amino acid region in the C-terminal of the FAK F1 lobe. These findings indicate that therapeutic agents with structural attributes of this much smaller region of FAK to disrupt the pressure signaling pathway.

Pressure-stimulated adhesion can be blocked. Survival has been improved in murine tumor models using either colchicine (Craig et al. J Clin Invest 118(9):3170-80 (2008)) or siRNA to alpha-actinin-1 (Craig et al., Neoplasia 10(3): 217-22 (2008)) to interrupt cytoskeletal mechanotransduction, but the concentration of colchicine required to achieve these effects is substantially higher than that acceptable in humans, while molecular modification by siRNA techniques would be challenging in the clinical setting. Inhibitors that target FAK and Akt1 directly can also prevent pressure-stimulated adhesion in vitro. However, these important kinases have diverse cell functions and blocking either can produce substantial side effects. For instance, FAK inhibitors such as Y15 may cause peritonitis with fatal complications, and Akt1 blockade reduces cell proliferation in a way that diminishes the effect of chemotherapeutic agents reliant on DNA replication (Golubovskaya et al. Arch Toxicol 89(7):1095-101 (2015); (Galvez-Peralta et al. Mol Pharmacol 85(5):723-34 (2014)).

Mechanical forces recruit FAK and Akt1 to one another to stimulate cancer cell adhesion, an interaction not common among previously described signal pathways. As described herein, force-activated FAK-Akt1 interaction was selected as a target because it can have less side effects. Preventing this specific interaction seems would have less off-target effects than the global consequences of blocking all catalytic functions of either kinase. As illustrated herein such an interaction can be blocked by the expression of FAK fragments modeled after key components involved in the binding of these two kinases.

Figure 4A:
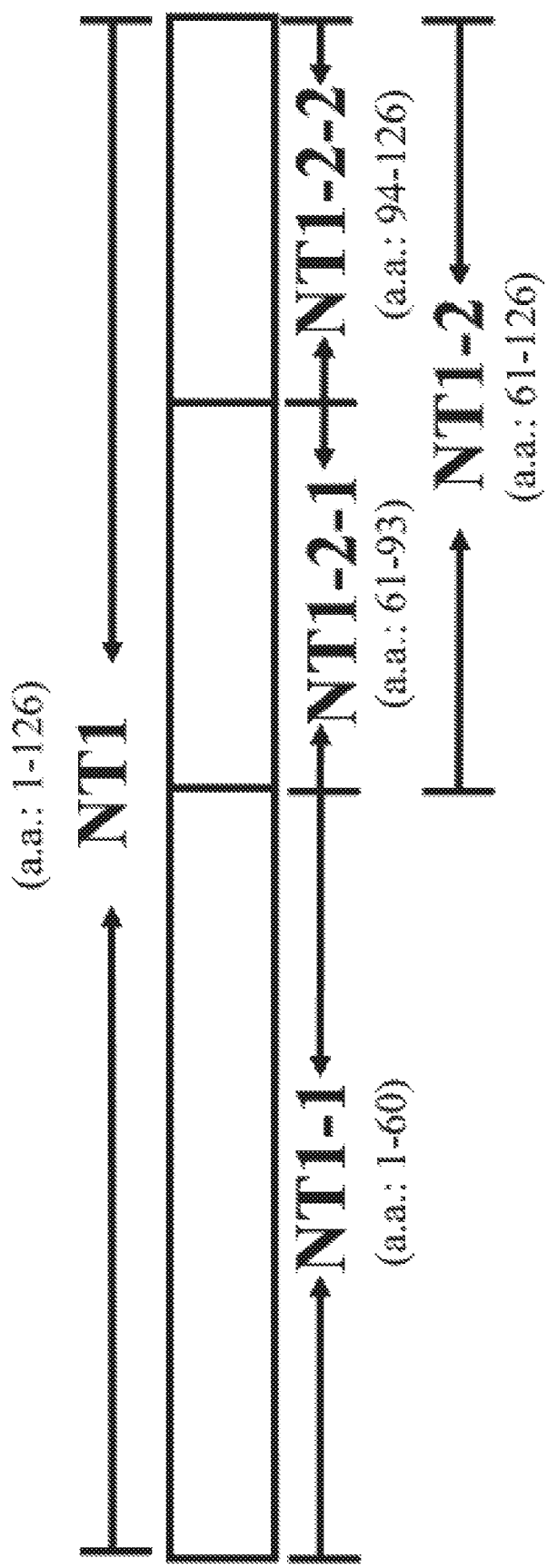
FIG. 4A-4C illustrate that Akt1/FAK binding requires the Akt1 kinase domain.

The FAK molecule is functionally divided into the N-terminal erythrocyte band four.1-ezrin-radixin-moesin (FERM) domain (residues 35-362), the central kinase domain (residues 416-676), and the C-terminal focal adhesion targeting (FAT) domain (residues 677-1025). The FERM domain both connects components of the cell membrane to the cytoskeleton and regulates FAK activity. The FERM domain is further divided into three lobes: F1 (residues 35-130), F2 (residues 131-255), and F3 (residues 256-362). The F2 lobe regulates FAK catalytic activity by binding the kinase domain and folding the FERM over it to physically occlude the active site. The F3 lobe exhibits homology with regions of other FERM domains that bind the cytoplasmic tails of β integrins and ICAM-2 when activated. Compared to the rest of the FERM domain, less is known about the function of the F1 lobe. However, the F1 lobe in its entirety and with the FAK NT1-2-2 region (residues 94-126; FIG. 4), is involved in Akt1 binding.

While the activation site of FAK (tyrosine 397) is outside the F1 region, changes to the residues within the F1 lobe, which do not physically contact tyrosine 397, are yet capable of triggering FAK activation (Ceccarelli et al. J Biol Chem. 281(1):252-9 (2006)). Such an allosteric activation may reconcile the importance of the F1 lobe with the Akt1-dependent FAK activation seen with pressure stimulation. Additionally, the specificity of this relationship is demonstrated by the inability of HA-FRNK (FAK-related non-kinase) to binds Akt1. This is noteworthy as FRNK is an established FAK truncation consisting of only the FAK C-terminal FAT domain and is often used for its ability to bind, but not phosphorylate, FAK targets (Sieg et al. J Cell Sci. 112 (Pt 16):2677-91 (1999)). Specifically, FRNK binds to focal adhesion complexes. This further coincides with our findings that pressure induces FAK-Akt1 association in suspended cells which have yet to form focal adhesion complexes (Thamilselvan, Gastroenterology 126(1):8-18 (2004)). Hence, the F1 lobe is important for the FAK-Akt1 interaction.

The expression of the FAK-NT1 region (SEQ ID NO:3) successfully inhibited the stimulatory effect of pressure on cell adhesion in two different cell lines, using transient or stable inducible overexpression. This is consistent with previous observations showing binding between the NT1 region of FAK and Akt1 (Basson et al. J Physiol Pharmacol. 66(5):701-9 (2015)). The results in two different model systems strongly support the conclusion that FAK interacts with Akt1 in response to pressure stimulation via the FAK-NT1 (SEQ ID NO:3) region. Transient or induced overexpression of the GFP-FAK-NT1 plasmid in Caco-2 cells also decreased basal cell adhesion indicating some tonic activity of this force-activated pathway even in the absence of increased pressure stimulation. However, FAK-NT1 (SEQ ID NO:3) is 126 amino acids in length. Such a large protein would be challenging either to dose pharmacologically or to mimic with small molecule analogs. A parallel set of studies examining Akt1 truncations was not able to narrow the Akt1 binding site for FAK down to a single small domain. The FAK binding site on Akt1 seems to span across the entirety of the Akt1 kinase domain as both N- and C-terminal based truncations of the region were equally capable of pulling down FAK (Basson et al. J Physiol Pharmacol. 66(5):701-9 (2015)). By contrast, serial truncation studies of FAK were able to narrow down the region on FAK required for Akt1 binding to the 33-amino acid sequence in the FAK-NT1-2-2 truncation. Indeed, the FAK-NT1-2-2 region contains a segment that is surface accessible and may be responsible for orchestrating the Akt1 binding we observe through these pull-down assays (FIG. 5A-5B). About one quarter the size of the larger FAK-NT1, this smaller subdomain may prove much easier to model or manipulate and may be an important target for future study.

Ninety percent of cancer deaths are attributed not to the original tumor but to metastatic growths. Such metastasis requires many steps but one key step is the adhesion of disseminated or circulating tumor cells to a remote substrate. It is noteworthy in this regard that physical forces activate a very different pathway in cancer cells that are already adherent, so that the same stimuli that promote the adhesiveness of circulating cells would not be expected to prevent the motility and invasion of tumor cells within a primary tumor. The force-activated pro-adhesive pathway targeted here can be present in malignant cell types including colon cancers, squamous head and neck cancers, breast cancers, and even sarcomas. Thus, inhibiting this pro-metastatic signal cascade might have substantial benefits for reducing perioperative tumor dissemination and even longer term metastasis from unresectable tumors. These results demonstrate that this pathway can be inhibited by interfering with FAK-Akt1 binding, in a fashion that may bypass the off-target effects common to currently available therapeutics.

Physical forces evoke signaling responses across diverse cells by different mechanisms. The potentiation of adhesion in suspended cancer cells by a force-activated pathway represents a target for inhibiting metastasis, and the uncommon FAK-Akt1 interaction essential for this pathway seems an attractive target because blocking it may not affect other FAK signaling. The results described herein demonstrate that Akt1 interacts with FAK directly without an intermediary protein, likely via a short helix on the surface of the FAK F1 lobe, and that this FAK-Akt1 interaction can be blocked by peptides derived from said F1 lobe. Indeed, adenoviral delivery of this peptide into intact cancer cells blocks both pressure-activated signaling and consequent increases in cell adhesion without interfering with other aspects of FAK or Akt1 signaling. The results described herein show that interventions using or mimicking the FAK-derived peptide may translate to in vivo models and increase tumor-free survival by mitigating pressure-stimulated tumor adhesion.

Figure 7A:
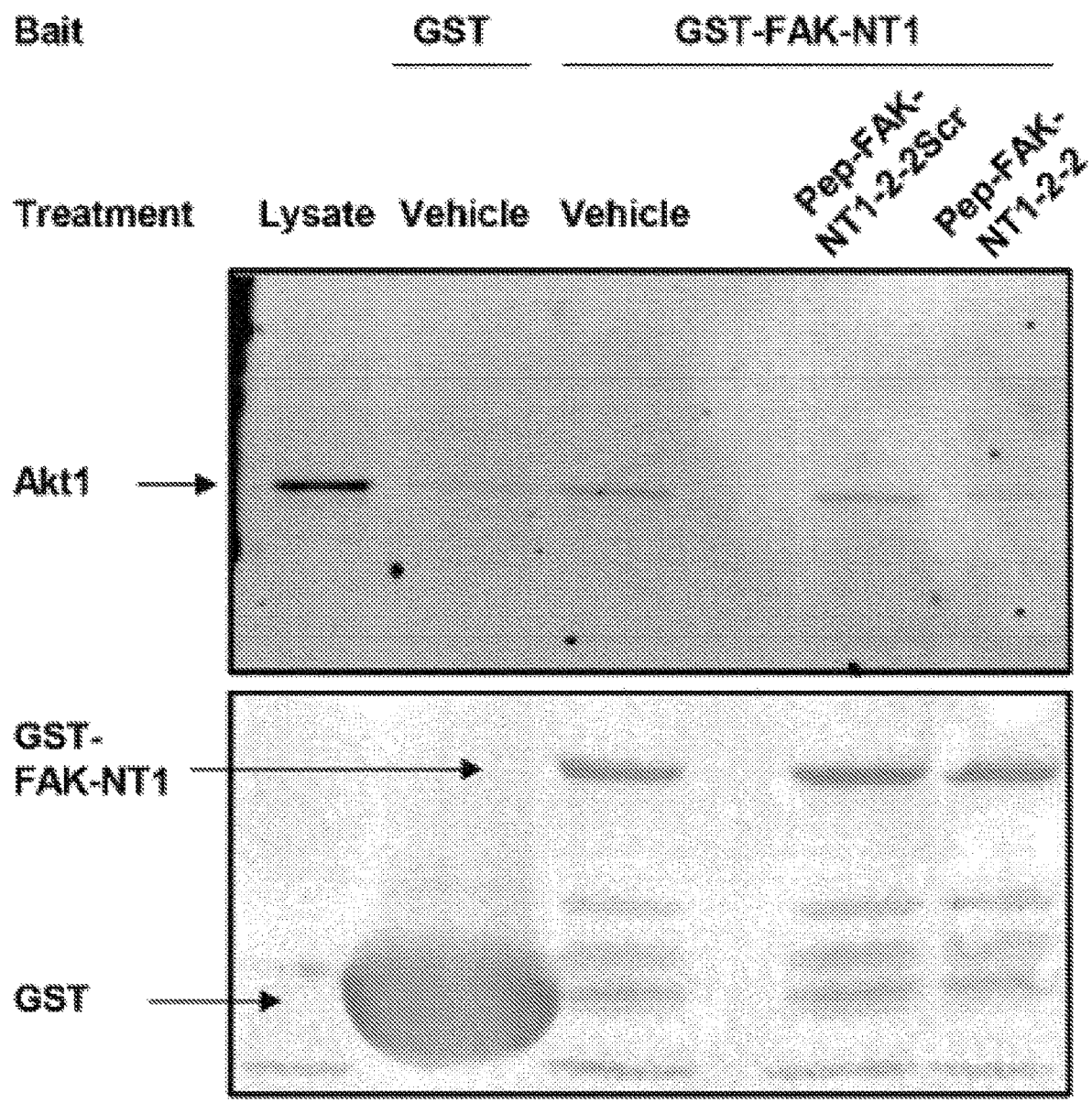
FIG. 7A-7G illustrate that FAK-derived peptides interfere with FAK-Akt1 interaction.
Figure 7B:
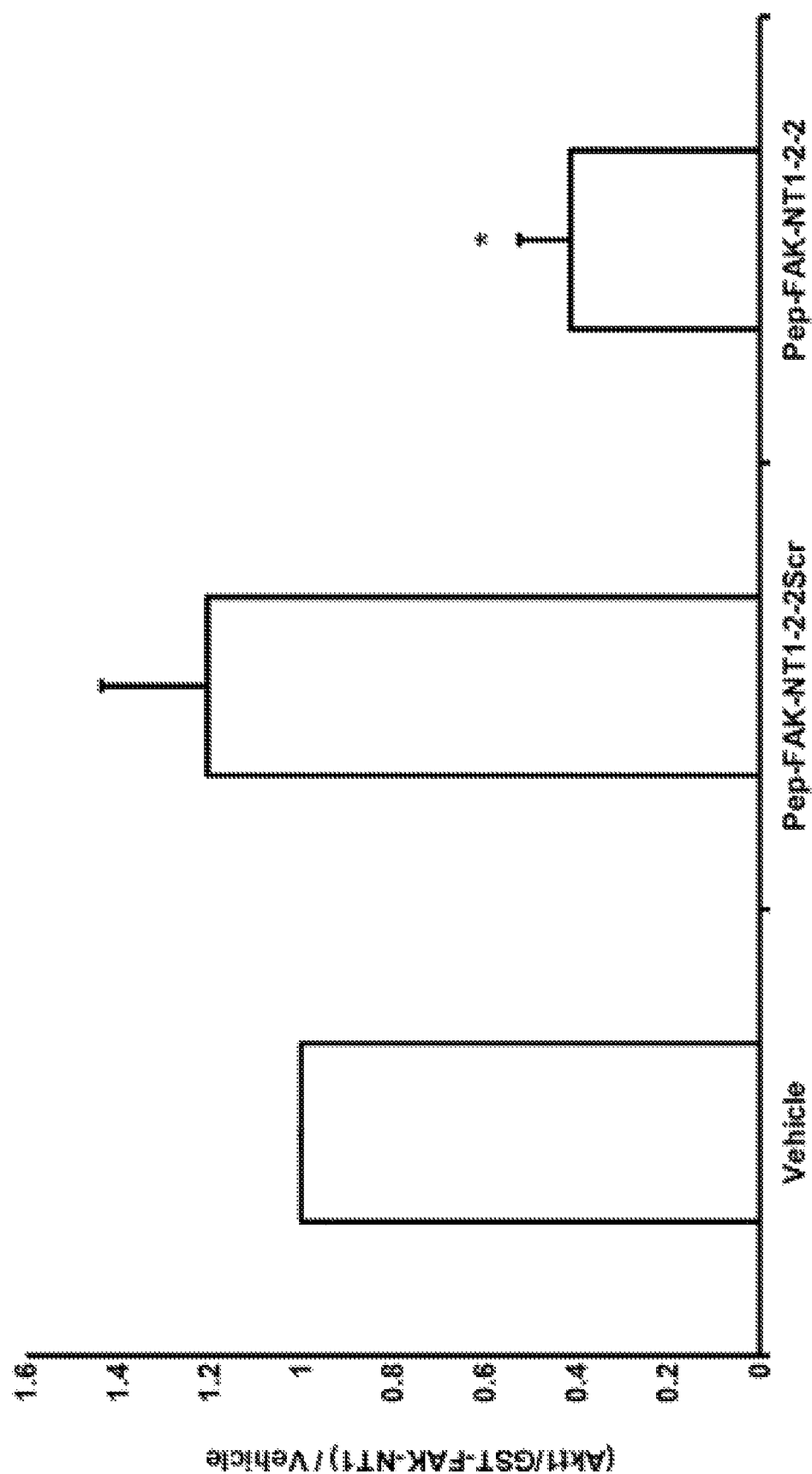
Figure 7C:
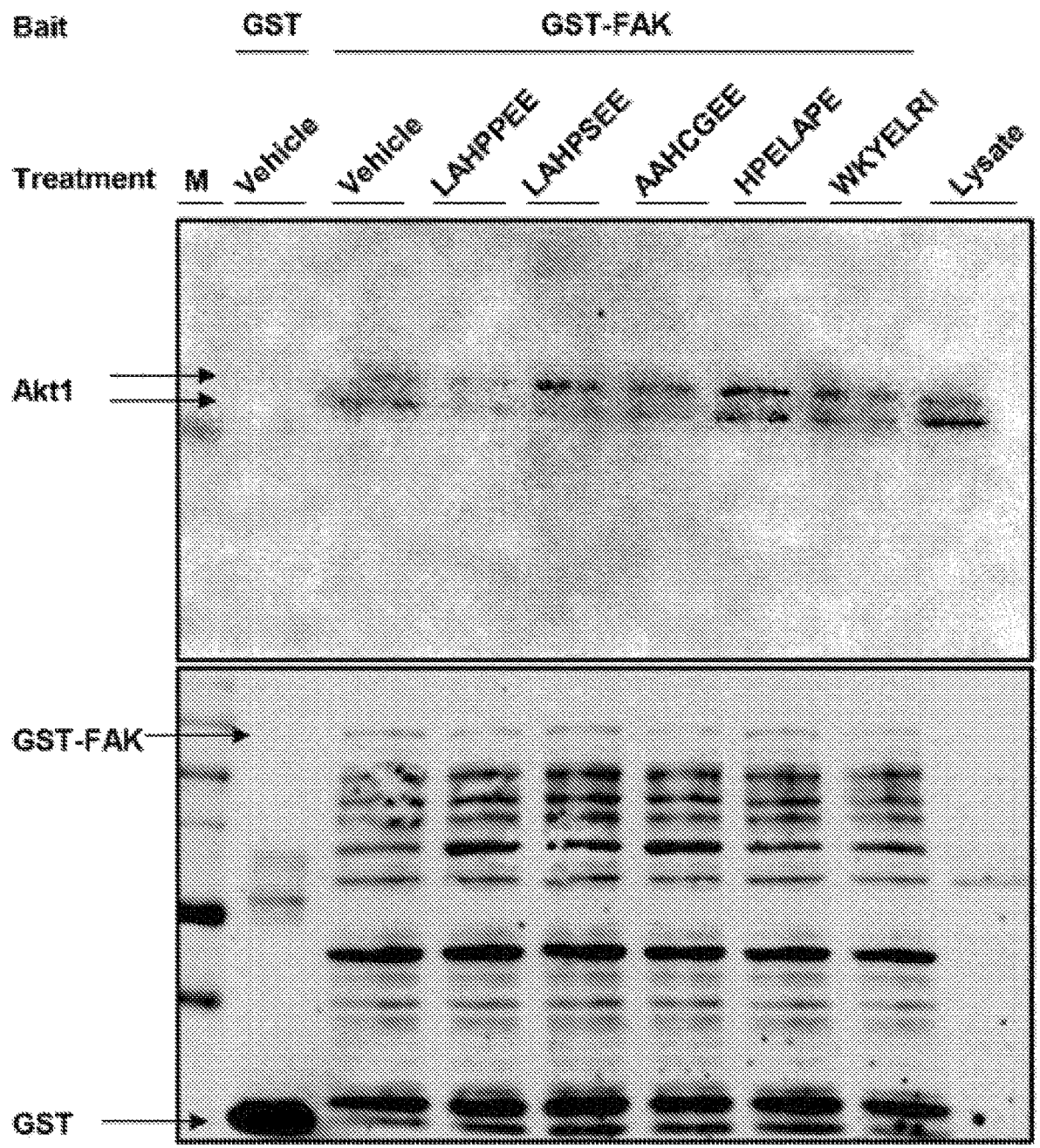
Figure 7D:
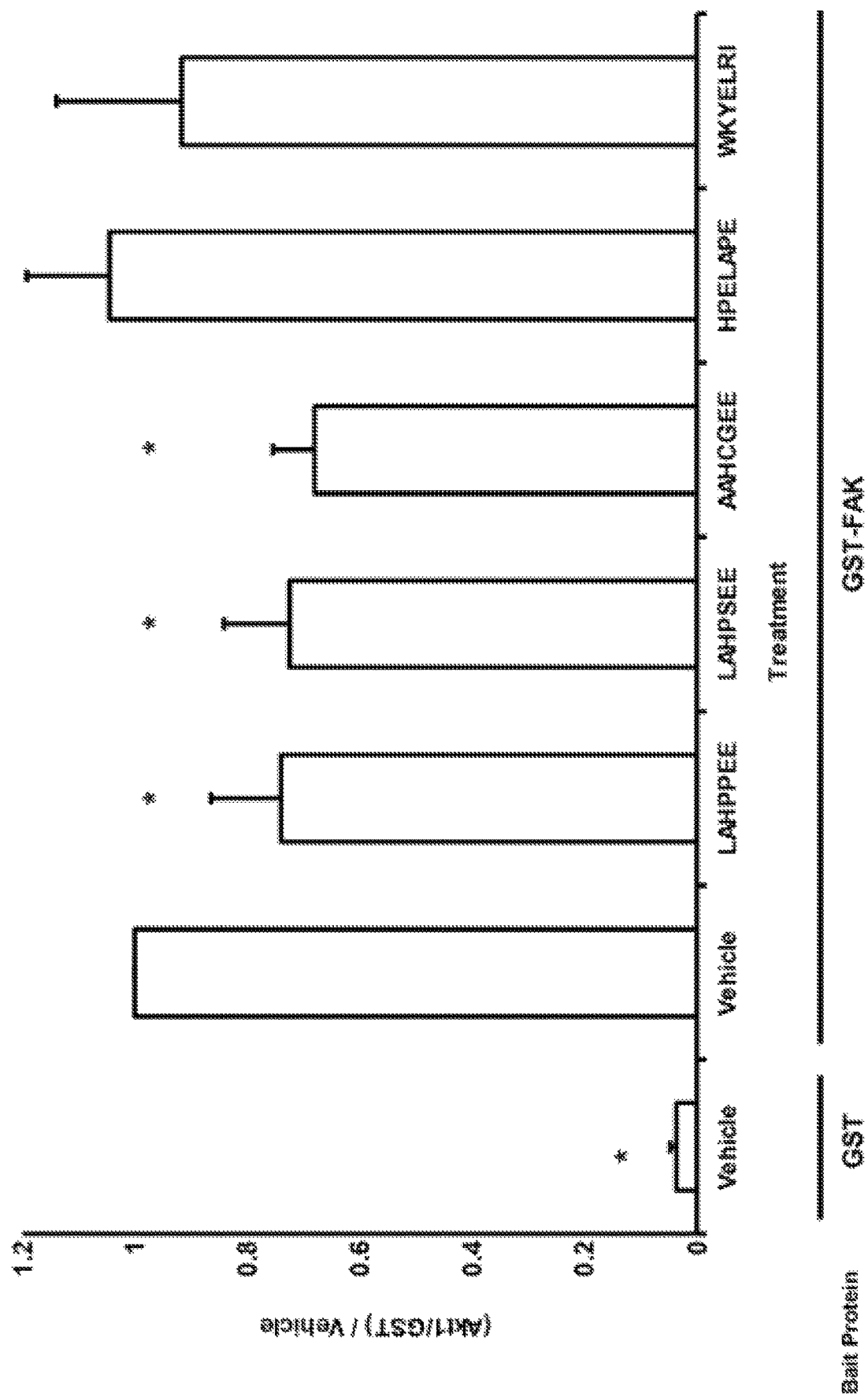
Figure 7F:
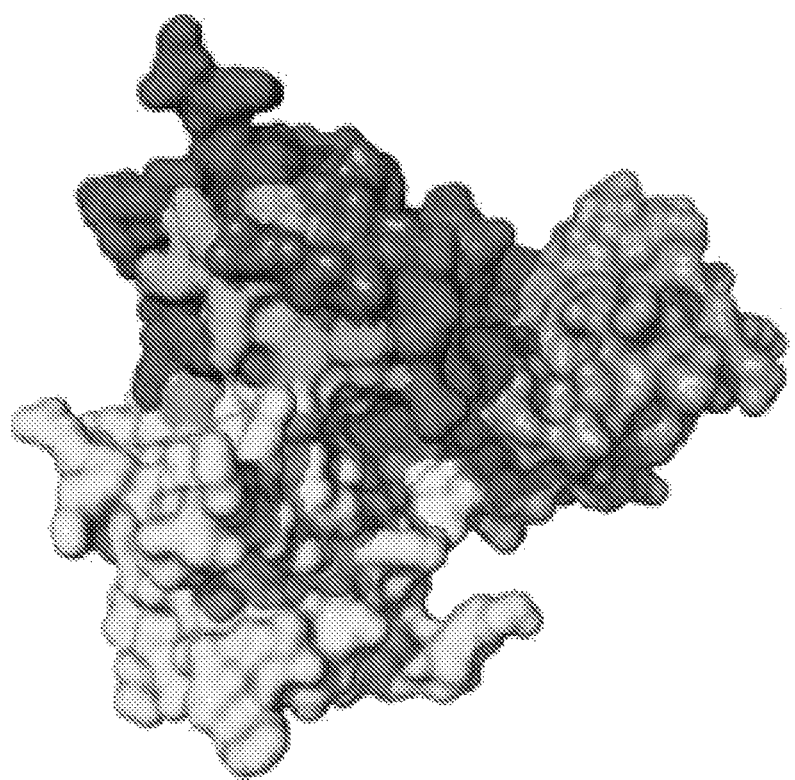
Figure 7E:
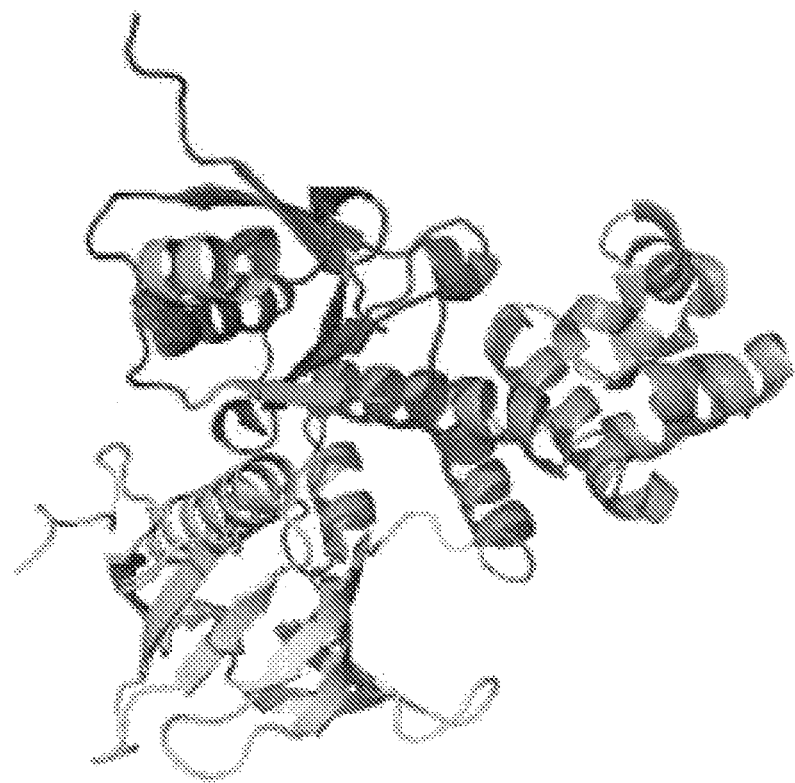
Figure 7G:
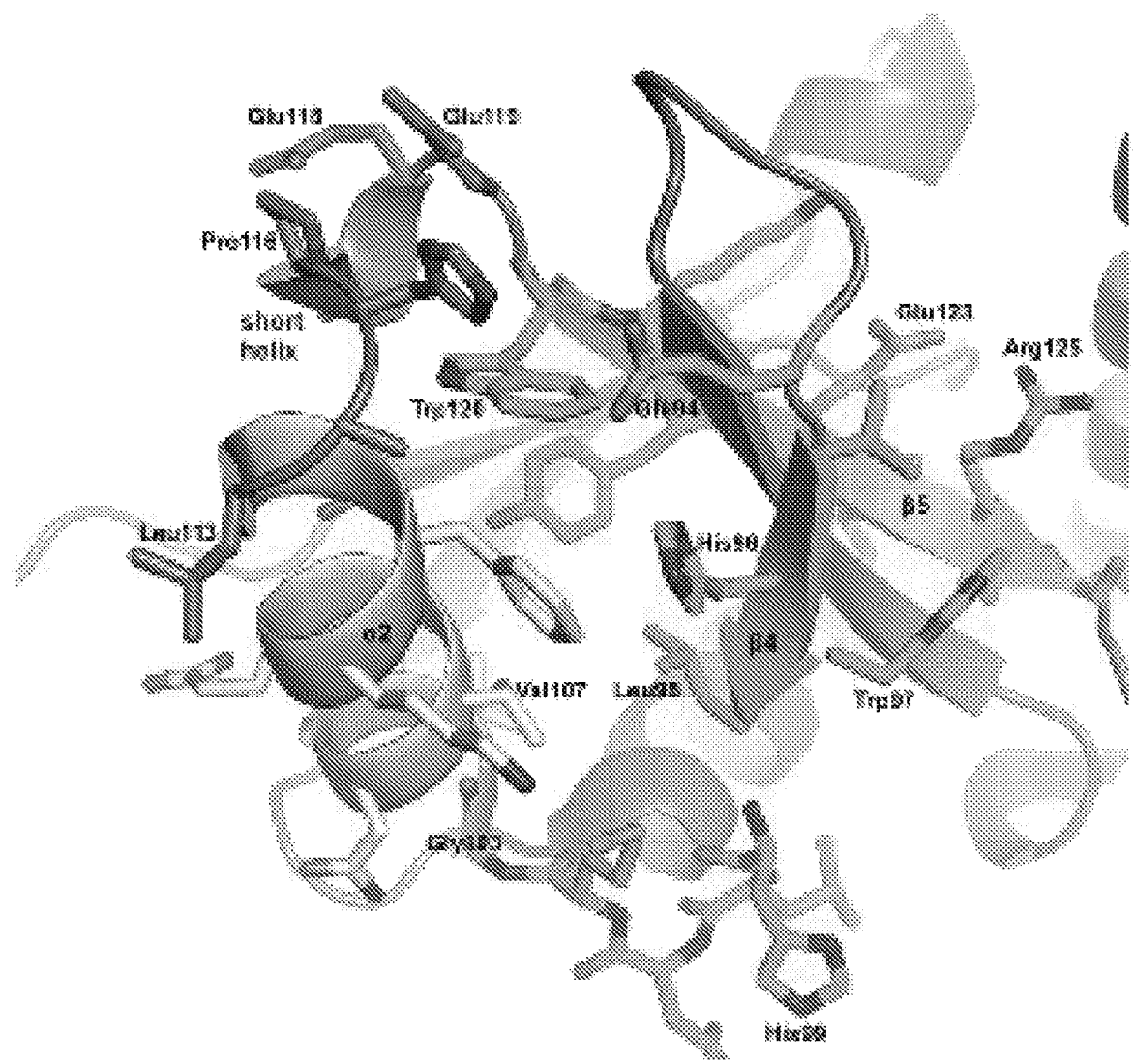

The pull-down methods described herein has successfully been used for identifying the region of FAK responsible for binding Akt1, and can be used to identify variant peptides and small molecules that inhibit FAK binding to Akt1. As shown herein by successive truncations of the FAK protein, a seven-residue sequence (residues 113-119, LAHPPEE, SEQ ID NO:1) containing a short helix on the surface of the F1 lobe of the FAK FERM domain that can pull down Akt1. Furthermore, mutations in this region can increase or decrease alter Akt1 affinity for FAK. Pressure requires FAK-Akt1 interaction to stimulate FAK tyrosine-397 autophosphorylation and activation (Wang et al., Am J Physiol Cell Physiol 300:C657-70 (2011)). The FAK F1 lobe appears sufficient to bind Akt1. The FERM domain includes three lobes: F1 (residues 35-130), F2 (residues 131-255), and F3 (residues 256-362) (FIG. 7E-7F). The F2 lobe binds the kinase domain to fold the entire FERM domain over the kinase, inhibiting FAK catalytic activity by active site denial.

The F3 lobe of FAK contains a site homologous to other FERM domains that, upon activation, binds cytoplasmic tails of β-integrins and ICAM-2 (Ceccarelli et al., J Biol Chem 281:252-9 (2006)). It is interesting that the F1 lobe mediates FAK-Akt1 interaction, not the better characterized F2 and F3 lobes, because the F2 lobe regulates FAK activation following cell adhesion (31), while pressure activates FAK in suspended cells before adhesion (Ceccarelli 2006). Similarly, the potential protein interaction site of the F3 lobe is occluded in inactivated FAK, precluding it from participating in pressure-induced FAK-Akt1 interactions that cause FAK autophosphorylation (Thamilselvan et al., FASEB J 21:1730-41 (2007)).

Changes to F1 lobe residues that do not physically contact tyrosine-397 can activate FAK (Ceccarelli 2006). Mutation of lysine-38, which is topographically distant from tyrosine-397 in crystal structures, may promote tyrosine-397 phosphorylation by destabilizing the FERM-linker interaction (Cohen et al., J Biol Chem 280:8197-207 (2205)). These data support a conclusion that FAK-Akt1 interactions alter the F1 lobe of FAK to autophosphorylate tyrosine-397.

Adenoviral delivery of a short helical FAK peptide blocked pressure-induced FAK tyrosine-397 phosphorylation and FAK-Akt1 coimmunoprecipitation. This short helical peptide also interrupted FAK-Akt1 interaction while preserving Akt1 kinase activity and downstream GSK phosphorylation. Together with the decrease in pressure-induced FAK-Akt1 association and FAK activation, these observations show that the short helical FAK peptide interferes with Akt1 binding to FAK, but not with Akt1's catalytic competence.

The molecular data provided herein shows that the short helical peptide inhibits pressure-induced cell adhesion stimulation of adhesion by pressure in wounds and by tumor cells. Indeed, in the tumor progression model, treatment with the virally delivered peptide not only prevented the reduction of tumor-free survival by pressure but increased tumor-free survival in the mice implanted with Ad-FAK-Helix-infected SW620 cells activated with increased pressure compared to those preincubated only at ambient pressure.

These results described herein indicate that perturbing FAK-Akt1 interaction, by mimicking the structure of a small segment of the F1 FAK lobe, can abate the sensitivity of suspended malignant cells to mechanical signals, mitigating both the biochemical and the clinical consequences of this force-activated pathway. Such s decrease in FAK and Akt1 activation and such inhibition of cell adhesion can attenuate the metastatic potential of shed tumor cells during surgery and increase tumor-free survival.

Potential toxicity and off-target effects limit the clinical utility of other methods to inhibit this force-activated adhesion pathway, such as high dose colchicine, disruption of the cytoarchitecture, or non-specific FAK and Akt inhibitors. Preventing FAK-Akt1 interaction without interfering with other aspects of FAK or Akt1 signaling can inhibit metastasis with fewer and less adverse effects on other cell function as well as less toxicity.

Recombinant Expression

The peptide inhibitors can be recombinantly expressed to provide useful amounts of peptide to be administered in a pharmaceutical composition, or recombinant expression cassettes or vectors can be generated and such vectors can be administered to allow expression of the peptide inhibitor(s) in vivo. An expression cassette or expression vector can include a nucleic acid that encodes any of the peptide inhibitors described herein. For example, the expression cassette or expression vector can include a nucleic acid that encodes a peptide with one or more of SEQ ID NO:1, 2, 3, 4, 6, 7, 10, 11, 12-20, 21, or 22, or a peptide with a sequence related to one or more of SEQ ID NO:1, 2, 3, 4, 6, 7, 10, 11, 12-20, 21, or 22.

Such an expression cassette or expression vector can be introduced and the encoded peptide(s) can be expressed in *Escherichia coli*, yeast, insect cell, animal cell, or human cell. Such expression can be used to manufacture any of the peptide inhibitors described herein. Alternatively, the expression cassette or expression vector can be administered to a mammal or human patient for expression of the peptide inhibitor in vivo within the mammal or human patient.

The nucleic acids encoding any of the peptides disclosed herein can be inserted into or employed with any suitable expression system. Recombinant expression is usefully accomplished using a vector, such as a plasmid. The vector can include a promoter operably linked to nucleic acid encoding a peptide inhibitor. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying peptide-encoded constructs can be produced. Such expression vectors include, for example, pET, pET3d, pCR2.1, pBAD, pUC, and yeast vectors. The vectors can be used, for example, in a variety of in vivo and in vitro situations.

Viral vectors include adenovirus, adeno-associated virus, herpes virus, vaccinia virus, polio virus, A IDS virus, neuronal trophic virus, Sindbis and other RNA viruses, including these viruses with the HIV backbone. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp 229-232, Washington, (1985). For example, such retroviral vectors can include Murine Maloney Leukemia virus, MMLV, and other retroviruses that express desirable properties Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. A "promoter" contains core elements required for basic interaction of RNA polymerase and transcription factors and can contain upstream elements and response elements "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The expression cassette or vector can include nucleic acid sequence encoding a marker product. This marker product is used to determine if the gene has been delivered to the cell and once delivered is being expressed. Preferred marker genes are the *E. coli* lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B et al., Mol Cell. Biol. 5: 410-413 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J A., et al., Science, 247, 1465-1468, (1990), and Wolff, J. A. Nature, 352, 815-818, (1991).

Viral Vectors

Examples of vectors that can be employed include Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. For example, the retroviral vector can be derived from a Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not useful in non-proliferating cells. Adenovirus vectors are relatively stable and easy to work with, have high titers, and can be delivered in aerosol formulation, and can transfect non-dividing cells. Pox viral vectors are large and have several sites for inserting genes; they are thermostable and can be stored at room temperature.

Viral vectors can introduce larger nucleic acids into cells than some chemical or physical methods. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

The construction of replication-defective adenoviruses has been described (Berkner et al., J. Virology 61:1213-1220 (1987); Massie et al., Mol. Cell Biol 6:2872-2883 (1986): Haj-Ahmad et al., J. Virology 57:267-274 (1986); Davidson et al., J. Virology 61:1226-1239 (1987): Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4.154-159 (1993); La Salle, Science 259.988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73.1201-1207 (1993): Bout, Human Gene Therapy 5:3-10 (1994); Zabner. Cell 75:207-216 (1993); Caillaud, Eur. J Neuroscience 5.1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J Virology 55:442-449 (1985): Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A preferred viral vector is one based on an adenovirus which has had the E1 gene removed and these virions are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

The inserted genes in viral and retroviral usually contain promoters, and/or enhancers to help control the expression of the desired gene product. A promoter is generally a sequence or sequences of DNA that function when in a relatively fixed location in regard to the transcription start site A promoter contains core elements required for basic interaction of RNA polymerase and transcription factors, and can contain upstream elements and response elements.

Viral Promoters and Enhancers

Examples of promoters for controlling transcription from vectors in mammalian host cells include those from: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)) The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

An enhancer generally refers to a sequence of DNA that functions at no fixed distance from the transcription start site and can be either 5' (Laimins, L et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, a-fetoprotein and insulin), typically one will use an enhancer from a eukaryotic cell virus Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

The promoter and/or enhancer region can be active in all eukaryotic cell types. For example, the promoter can be a CMV promoter (650 bases), a SV40 promoter, a cytomegalovirus (full length) promoter, or a retroviral vector LTF.

Any desired regulatory element can be cloned and used to construct expression vectors that are selectively expressed in specific cell types such as cancer or tumor cells. For example, the glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In a preferred embodiment of the transcription unit, the polyadenylation region is derived from the SV40 early polyadenylation signal and consists of about 400 bases. It is also preferred that the transcribed units contain other standard sequences alone or in combination with the above sequences improve expression from, or stability of, the construct.

Markers

The vectors can include nucleic acid sequence encoding a marker product. This marker product is used to determine if the gene has been delivered to the cell and once delivered is being expressed. An example of a marker product is the green fluorescent protein; an example of a marker gene is the E. coli lacZ gene which encodes β-galactosidase.

In some embodiments the marker can be a selectable marker Examples of suitable selectable markers for mammalian cells are dihydrofolate reductase (DHFR), thymidine kinase, neomycin, neomycin analog G418, hydromycin, and puromycin.

When such selectable markers are successfully transferred into a mammalian host cell, the transformed mammalian host cell can survive if placed under selective pressure.

There are two widely used distinct categories of selective regimes. The first category is based on a cell's metabolism and the use of a mutant cell line which lacks the ability to grow independent of a supplemented media Two examples are: CHO DHFR cells and mouse LTK cells. These cells lack the ability to grow without the addition of such nutrients as thymidine or hypoxanthine Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

A second category is a marker that dominantly selective and can be used in any cell type. Thus, it is not necessary to use a mutant cell line. Use of dominantly selective markers typically involves use of a drug to arrest growth of a host cell. Those cells expressing the dominantly selective marker express a protein conveying drug resistance and survive the selection. Examples of such dominant selection use the drugs neomycin, (Southern P. and Berg, P., J. Molec. Appl Genet 1: 327 (1982)), mycophenolic acid, (Mulligan, R. C. and Berg, P. Science 209: 1422 (1980)) or hygromycin, (Sugden, B. et al., Mol. Cell Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Any of the elements described above or used by those of skill in the art can be used in expression cassettes or vectors for recombinant expression of inhibitory peptides or for in vivo expression of the inhibitory peptides.

Compositions

The invention also relates to compositions containing an inhibitor of Akt1 and FAK interaction. Such an inhibitor can be a peptide, a small molecule, or a nucleic acid encoding a peptide inhibitor (e.g., within an expression cassette or expression vector). The compositions of the invention can be pharmaceutical compositions. In some embodiments, the compositions can include a pharmaceutically acceptable carrier. By "pharmaceutically acceptable" it is meant that a carrier, diluent, excipient, and/or salt is compatible with the other ingredients of the formulation, and not deleterious to the recipient thereof.

The peptide inhibitor composition can be formulated in any convenient form. In some embodiments, the peptide inhibitor can have an amino acid sequence such as any of SEQ ID NO:1, 2, 3, 4, 6, 7, 10, 11, 12-20, 21, 22, or a combination thereof. In other embodiments, the peptide inhibitor can have an amino acid sequence that is related to any of SEQ ID NO:1, 2, 3, 4, 6, 7, 10, 11, 12-20, 21, 22, or a combination thereof. For example, the peptide inhibitors of Akt1 and FAK interactions can have at least 80%, or 85%, or 90%, or 91%, or 92%, or 93%, or 94%, or 95%, or 96%, or 97%, or 98%, or 99% sequence identity to any of SEQ ID NO: 1, 2, 3, 4, 6, 7, 10, 11, 12-20, 21, or 22.

In some embodiments, the therapeutic agents of the invention (e.g., small molecules, peptide inhibitors of Akt1 and FAK interactions, and/or nucleic acids encoding such peptide inhibitors), are administered in a "therapeutically effective amount." Such a therapeutically effective amount is an amount sufficient to obtain the desired physiological effect, such a reduction of at least one symptom of cancer. For example, the inhibitors (small molecules, peptides, and/or nucleic acids encoding such peptides) can reduce FAK and Akt1 interaction and/or can decrease cancer cell adhesion and/or metastasis by 5%, or 10%, or 15%, or 20%, or 25%, or 30%, or 35%, or 40%, or 45%, or 50%, or 55%, or 60%, or 65%, or %70, or 80%, or 90%, 095%, or 97%, or 99%, or any numerical percentage between 5% and 100%. Symptoms of cancer can also include tumor cachexia, tumor-induced pain conditions, tumor-induced fatigue, tumor growth, and metastatic spread.

To achieve the desired effect(s), the small molecules, peptide inhibitors, nucleic acids encoding such peptide inhibitors, and combinations thereof, may be administered as single or divided dosages. For example, small molecules, peptide inhibitor(s) and/or nucleic acids encoding such peptide inhibitors, can be administered in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the small molecules, peptides, or nucleic acid chosen for administration, the disease, the weight, the physical condition, the health, and the age of the mammal. Such factors can be readily determined by the clinician employing animal models or other test systems that are available in the art.

Administration of the therapeutic agents (e.g., small molecules, peptides, or nucleic acids encoding such peptides) in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents and compositions of the invention may be essentially continuous over a preselected period of time or may be in a series of spaced doses. Both local and systemic administration is contemplated.

To prepare the composition, small molecules, peptides, nucleic acids, and other agents are synthesized or otherwise obtained, purified as necessary or desired. These molecules, peptides, nucleic acids, and other agents can be suspended in a pharmaceutically acceptable carrier and/or lyophilized or otherwise stabilized. The small molecules, peptide inhibitors, nucleic acids encoding such peptide inhibitors, and combinations thereof can be adjusted to an appropriate concentration, and optionally combined with other agents. The absolute weight of a given small molecule, peptide, nucleic acid, and/or other agent included in a unit dose can vary widely. For example, about 0.01 to about 2 g, or about 0.1 to about 500 mg, of at least one molecule, peptide, nucleic acid, and/or other agent, or a plurality of molecules, peptides, nucleic acids, and/or other agents can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the therapeutic agents of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of molecules, peptides, nucleic acids and/or other agents for use in treatment will vary not only with the particular carrier selected but also with the route of administration, the nature of the cancer condition being treated and the age and condition of the patient. Ultimately the attendant health care provider can determine proper dosage. In addition, a pharmaceutical composition can be formulated as a single unit dosage form.

Thus, one or more suitable unit dosage forms comprising the peptide(s), nucleic acid(s) and/or agent(s) can be administered by a variety of routes including parenteral (including subcutaneous, intravenous, intramuscular and intraperitoneal), oral, rectal, dermal, transdermal, intrathoracic, intrapulmonary and intranasal (respiratory) routes. The peptides, nucleic acids and/or agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system. For example the molecules and/or peptides can be linked to a convenient carrier such as a nanoparticle, albumin, polyalkylene glycol, or be supplied in prodrug form. The small molecules, peptide inhibitors, nucleic acids encoding such peptide inhibitors, and combinations thereof can be combined with a carrier and/or encapsulated in a vesicle such as a liposome.

The compositions of the invention may be prepared in many forms that include aqueous solutions, suspensions, tablets, hard or soft gelatin capsules, and liposomes and other slow-release formulations, such as shaped polymeric gels. Administration of inhibitors can also involve parenteral or local administration of the in an aqueous solution or sustained release vehicle.

Thus while the molecules, peptides, nucleic acids and/or other agents can sometimes be administered in an oral dosage form, that oral dosage form can be formulated so as to protect the molecules, peptides, nucleic acids from degradation or breakdown before the small molecules, peptide inhibitors, nucleic acids encoding such peptide inhibitors, and combinations thereof provide therapeutic utility. For example, in some cases the small molecules, peptide inhibitors, nucleic acids encoding such peptide inhibitors, and/or other agents can be formulated for release into the intestine after passing through the stomach. Such formulations are described, for example, in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicle before use. Such liquid pharmaceutical compositions may contain conventional additives such as suspending agents, emulsifying agents, non-aqueous vehicles (which may include edible oils), or preservatives. The pharmaceutical compositions may take such forms as suspensions, solutions, or emulsions in oily or aqueous vehicles, and may contain formulatory agents such as suspending, stabilizing and/or dispersing agents. Suitable carriers include saline solution, encapsulating agents (e.g., liposomes), and other materials. The inhibitors can be formulated in dry form (e.g., in freeze-dried form), in the presence or absence of a carrier. If a carrier is desired, the carrier can be included in the pharmaceutical formulation, or can be separately packaged in a separate container, for addition to the inhibitor that is packaged in dry form, in suspension or in soluble concentrated form in a convenient liquid.

An inhibitor can be formulated for parenteral administration (e.g., by injection, for example, bolus injection or continuous infusion) and may be presented in unit dosage form in ampoules, prefilled syringes, small volume infusion containers or multi-dose containers with an added preservative.

The compositions can also contain other ingredients such as chemotherapeutic agents, anti-viral agents, antibacterial agents, antimicrobial agents and/or preservatives. Examples of additional therapeutic agents that may be used include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as *vinca* alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The inhibitors can also be used in conjunction with radiation therapy.

The following non-limiting Examples illustrate some aspects of the development of the invention.

Example 1: Materials and Methods

This Example describes some of the materials and methods used during development of the invention.
Materials
Human Caco-2 and murine CT-26 colon cancer cells were cultured according to American Type Culture Collection (Rockville, Md.) recommendations. We obtained Lipofectamine 2000 and other transfection supplies from Invitrogen (Carlsbad, Calif.), Glutathione Sepharose 4B beads from GE Life Sciences (Pittsburgh, Pa.), and Akt1 and GST antibodies from Cell Signaling Technology (Beverly, Mass.). All primers were purchased from Integrated DNA Technologies (Coralville, Iowa). QIAquick Gel Extraction, QIAprep spin Miniprep, QIAquick PCR purification and QIAfilter Plasmid Maxi kits were purchased from Qiagen (Valencia, Calif.).

Generation of Constructs Mammalian expression vectors pGEX-4T-1 glutathione S-transferase (GST)-FAK-NT1 and its truncations were constructed via PCR of an HA-FAK (WT) plasmid template and introduced into the bacterial expression vector pGEX-4T1 (GE Healthcare, Munich, Germany) through 5'EcoRI and 3'XhoI cut sites. GST-Akt1 was generated by the same manner using a pcDNA3-myr-HA-Akt1 template (Addgene, Cambridge, Mass.). The HA-FAK (WT) itself, as well as the HA-FRNK (tagged at the COOH terminal), were gifts from Dr. David Schlaepfer. A similar protocol was used to generate the GFP-FAK-NT1 transient expression vector from the pEGFP-C1 vector Clontech (Mountain View, Calif.). Inducible GFP-FAK-NT1 expression was achieved using the pL6N2-RHS3H/ZF2-PL vector provided by the ARGENT regulated transcription retrovirus kit (now iDimerize inducible heterodimer system from Takara, Mountain View, Calif.).

Transfections

Caco-2 cells were plated on p100 dishes at 30-35% confluence one day prior to transfection. The constructed or empty plasmids were transfected into Caco-2 cells at final concentrations of 2 µg/ml plasmid and 5 µg/ml Lipofectamine 2000. Five hours after transfection, the medium was replaced with 15 ml pre-warmed Caco-2 media without antibiotics. Forty eight hours after DNA transfection, the cells were trypsinized for adhesion or pull-down experiments.

SW620 cells were transfected using Lipofectamine 2000 reagent (ThermoFisher, Waltham, Mass.) and HA-FAK (WT) plasmid (from Dr. J L Guan). Cells were grown in T75 flasks until 80% confluent, replated into 6 well plates at 80% confluence, and transfected 12 hours later per manufacturer's protocols.

Inducible Expression

A stable CT-26 cell line was generated per ARIAD-ARGENT protocols and GFP-FAK-NT1 expression was induced using 50 nM of the provided non-immunosuppressive rapalog, AP21967 with an equal volume of ethanol used as the control vehicle. Forty eight hours after induction, the cells were trypsinized for adhesion experiments.

Glutathione S-Transferase Pull-Down

Glutathione-Sepharose 4B beads (15 µl) were washed twice in ice-cold PBS and resuspended in 400 µl PBS. Bacterial lysate containing GST-Akt1, GST-FAK-NT1 (truncations), or GST proteins (gift of Dr. J. Chen) were then added in excess and incubated with the beads for 1 h. Glutathione-Sepharose 4B beads coupled to GST-Akt1, GST-FAK (truncations), or GST were then washed twice with PBS by centrifuge for 5 min at 500 g and incubated with nontransfected or transfected Caco-2 cell lysates (600-800 µg protein) overnight at 4° C. Transfected Caco-2 cells received plasmids encoding HA-WT-FAK or HA-FRNK. Nontransfected and transfected Caco-2 cell lysates were prepared in cell lysis buffer lysis buffer [50 mM Tris (pH 7.4), 150 mM NaCl, 1% Triton X-100, 1% sodium deoxycholate, 0.1% SDS, 1 mM EDTA, 1 mM phenylmethylsulfonyl fluoride, 1 mM Na3VO4, 50 mM NaF, 10 mM sodium pyrophosphate, 2 mg/ml aprotinin, and 2 mg/ml leupeptin (pH 7.4)]. Following incubation, beads were washed twice with lysis buffer without SDS and protease inhibitors. Proteins were eluted with Laemmli SDS sample dilution buffer, separated by 10% SDS-PAGE, and immunoblotted with GST, Akt1 (Cell Signaling Technology, Danvers, Mass.), or HA monoclonal antibodies (Covance, Chantilly, Va.).

In some cases Glutathione-Sepharose-4B beads (30 µl) (GE Healthcare Life Science, Pittsburgh, Pa.) were conjugated with GST (expressed protein from a 250 µl bacterial pellet per 30 µl of beads) or recombinant GST-tagged (expressed protein from a 3 ml bacterial pellet per 30 µl of beads) (24) and incubated with lysate from $2 \times 10^7$ Caco-2 or SW620 cells (1500 µg protein) or purified Akt1 (0.35 µg) (Origene, Rockville, Md.) overnight at 4° C. Similar incubation for two hours at 4° C. was performed with FAK-derived peptides (Peptide 2.0, Chantilly, Va.) reconstituted in sterile water and mixed with conjugated beads and cell lysate for a final concentration of 160 mM before overnight Akt1 incubation. Bound protein was eluted for western analysis (24).

Western Blotting

Western blots were performed as previously described[23]. Eluate from the pull-downs were resolved by SDS-polyacrylamide gel electrophoresis and transferred to Hybond ECL nitrocellulose membrane (Amersham Pharmacia Biotech, Piscataway, N.J.). Membranes were blotted with specific antibodies directed against either their wild-type structures or recombinant tags with the appropriate secondary antibody coupled to horseradish peroxidase. Bands were detected with enhanced chemiluminescence (Amersham) and analyzed with a Kodak Image Station 440CF (Perkin Elmer, Boston, Mass.). All exposures were within the linear range.

Protein concentrations were determined by bicinchoninic acid (BCA) protein assay (Pierce, Rockford, Ill.). Eluate from GST pull-downs or collected cell lysates was resolved by SDS-PAGE and transferred to Hybond P 0.45 PVDF blotting membrane (Amersham Life Science, Arlington Heights, Ill.). Membranes were blocked for 1 hour at room temperature with Odyssey TBS Blocking Buffer (Amersham Life Science, Arlington Heights, Ill.) and blotted overnight at 4° C. with antibodies against FAK (#3285), Phospho-FAK Tyr397 (#3283), Akt1 (#2967), Phospho-Akt1 Ser473 (#9271), GSK-3β (#9315), Phospho-GSK-3β Ser9 (#9315), or the GST tag (#2624) (CST, Beverly, Mass.). Membranes were visualized by the infrared fluorescent IRDye system (LI-COR Biosciences, Lincoln, Nebr.) and analyzed on an Odyssey scanner (LI-COR Biosciences, Lincoln, Nebr.) within the linear range. The doublet produced by the Akt1 antibody is consistent with results with this antibody (Ko et al., Elife: 5 (2016); Wu et al. Cell Discov 3: 16054 (2017)) and other (Datta et al. Cell 91: 231-41 (1997)) anti-Akt antibodies. Results were normalized to the appropriate GST tag, GAPDH, or total protein (for phosphorylated proteins) and relative to associated ambient controls unless stated otherwise.

Pressure Regulation

Experimental pressure conditions were controlled using an airtight box with inlet and outlet valves, thumb screws, a pressure gauge and an O-ring for an airtight (11, 25). The box was prewarmed to 37° C. for 1 hour to seal as previously described minimize temperature fluctuations experienced by the cells. The gas used for pressurization was a filtered 5% $CO_2$/95% air mixture consistent with the atmosphere in which the cells were routinely cultured. The temperature was maintained within ±2° C. and the pressure within ±1.5 mmHg. Partial pressures of O2 and CO2 and pH do not change appreciably during pressurization[11].

In some cases, pressure was controlled using an airtight apparatus previously described, pressurized with filtered 5% CO2/95%, and maintaining temperature, pressure, pO2, pCO2, and pH (Basson et al. J Cell Biochem 78:47-61 (2000).

Cell Adhesion Studies 100,000 Caco-2 or CT-26 cells were seeded to collagen I coated 6-well plates under ambient or increased pressure conditions for 30 minutes. Non-adherent cells were washed away, and the remainder fixed with 0.01 M NaIO$_4$, 0.75 M lysine, 0.0375 M sodium phosphate buffer, pH 7.4, and 2% paraformaldehyde on ice for 1 hour. The adherent cells were counted microscopically in at least 20 random high power fields per well under a fluorescent microscope.

In some cases SW620 colorectal adenocarcinoma cells (ATCC, Manassas, Va.) at 90% confluence, which had been split 1:4 two days previously to achieve 50-60% confluence on the day of adhesion assay. SW620 cells were trypsinized, plated randomly at 5×10$^4$ cells/well, and allowed to adhere to collagen-I-coated plates for 30 minutes at 37° C. under ambient or 15 mmHg increased pressure. After 30 minutes, non-adherent cells were washed away with warm PBS. Ambient and pressure-treated plates were encoded to prevent treatment identification during washing. Adherent cells were incubated for 1 hour at 37° C. with CellTiter 96 Aqueous One Solution Reagent (Promega, Madison, Wis.), and absorbance measured at 490 nm with an Epoch plate reader (Biotek, Winooski, Vt.). For adenoviral experiments, SW620 cells were grown to 90% confluence in a T25 flask (Corning, Corning, N.Y.) before viral infection (13×10$^3$ vp/cell) for 1 hour before replacing infection media with growth media. After 24 hours, infected SW620s were replated in new T25 flasks at a 1:4 ratio. At 72 hours, adhesion was assayed as above. Cells were used within ten passages and authenticated by ATCC.

FAK1 Structural Analysis

Structures were obtained from the Protein Data Bank (see website at www.rcsb.org): 2AL6. Structures were analyzed using Pymol from DeLano Scientific (San Carlos, Calif.).

Structure-Based Design of Peptidyl Epitopes to Compete with FAK for Binding Akt1

Figure 4B:
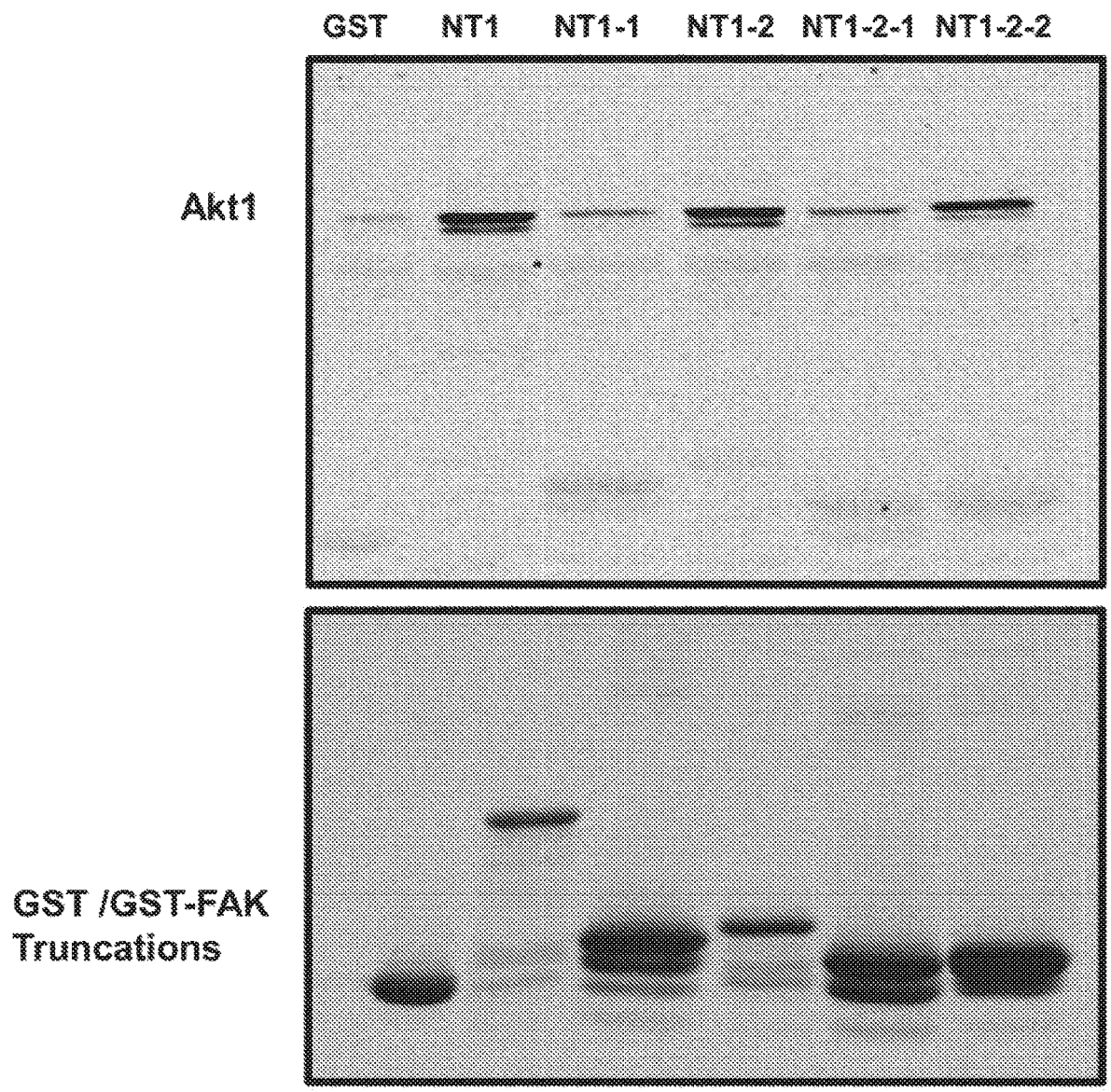
Figure 4C:
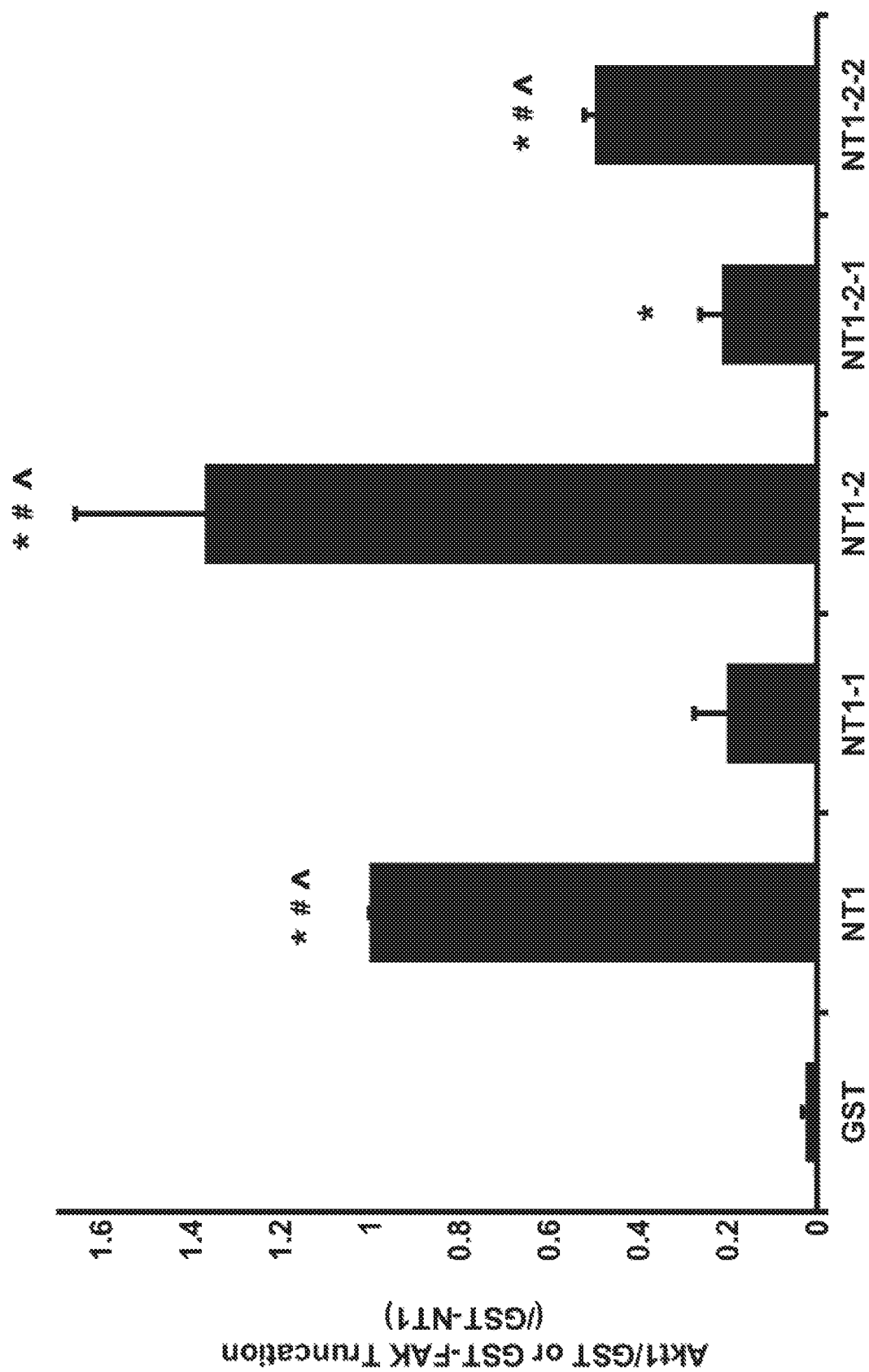

The crystal structure of human FAK (PDB 2AL6) and preliminary data showing Akt1 pulldown by a truncated 33 amino acid segment of the F1 lobe of FAK designated NT1-2-2 (Zeng et al. Gastroenterology 148 (4):5954-5955 (2015)) was evaluated. The inventors hypothesized that the NT1-2-2 region of FAK binds Akt1 through a short helical secondary structure accessible from the protein surface. The 33-residue peptide, NT1-2-2 (residues 94-126, SEQ ID NO:2) includes the second and fourth strands from a small β sheet in FAK (labelled 34 and (35 in FIG. 6D, based on their order in the sequence of PDB 2AL6 (31). This peptide does not include the third strand, which is needed for β-sheet integrity, so NT1-2-2 cannot mimic an intact β-sheet. However, the NT1-2-2 peptide does immunoprecipitate Akt1 (FIG. 4B). This indicates that the structurally self-determinate helical region in the NT1-2-2 peptide is the epitope involved in Akt1 binding, formed by the α2 helix plus a single turn of helix formed by residues 116-118 (PPE) (FIG. 7). Because hydrophobic interactions are important in protein-protein interfaces, we designed peptide variants centered on the hydrophobic C-terminal end of α2, followed by the PPE motif: LAHPPEE (SEQ ID NO:1, residues 113-117). Consideration of statistical amino acid preferences to occur in α helices, β sheets and reverse (β) turns was augmented by Sequery and SSA analysis (Craig et al. J Mol Biol 281:183-201 (1998); Prevelige & Fasman, Chou-Fasman Prediction of the Secondary Structure of Proteins: The Chou-Fasman-Prevelige Algorithm. In: Fasman G D, editor. Prediction of the Structure and the Principles of Protein Conformation. New York: Springer; 1989. p 391-416 (1989)) of the preferred 3D conformations of tetrapeptide sequences in this region (e.g., LAHP, AHPP, HPPE, etc.) across a representative set of 4300 non-homologous structures in the Protein Data Bank. Mutants of FAK (shown as the LAHPPEE, SEQ ID NO:1, sequence for simplicity) were designed and free peptides were used for competition with FAK as follows:

L113A: AAHPPEE (SEQ ID NO:12)—Enhanced a helical preference

P116N: LAHNPEE (SEQ ID NO:13)—Similar a helical, 0 turn preference in the PPE region, increased polarity P116C: LAHCPEE (SEQ ID NO:14)—Structurally labile, greater hydrophobicity P116G: LAHGPEE (SEQ ID NO:15)—Stronger turn preference, greater flexibility, less hydrophobicity P117K: LAHPKEE (SEQ ID NO:16)—Structurally labile, enhanced polarity P117S: LAHPSEE (SEQ ID NO:17)—More structurally labile and polar Triple mutant L113A, P116N, P117K: AAHNKEE (SEQ ID NO:18)—Enhanced helicity and polarity Triple mutant L113A, P116C, P117G: AAHCGEE (SEQ ID NO:19)—More structurally labile and hydrophobic Triple mutant: L113A, P116A, P117A: AAHAAEE—More helical and hydrophobic Generation and Expression of GST Fusion Proteins Bacterial expression vector pGEX-4T1 (GE Healthcare, Munich, Germany) was used as a template to generate mutated and truncated human FAK as GST (Glutathione S-transferase) fusion proteins. Point mutations (L113A, P116C, P116G, P116N, P117K, and P116S) and triple mutants (L113A/P116N/P117K, L113A/P116C/P117G, L113A/P116A/P117A) were generated using the Quick Change II XL Site-Directed Mutagenesis kit (Agilent Technologies, (Santa Clara, Calif.).

A FAK protein with a L113A mutation is shown below as SEQ ID NO: 27.

```
  1 MAAAYLDPNL NHTPNSSTKT HLGTGMERSP GAMERVLKVF

41 HYFESNSEPT TWASIIRHGD ATDVRGIIQK IVDSHKVKHV

81 ACYGFRLSHL RSEEVHWLHV DMGVSSVREK YEAAHPPEEW

121 KYELRIRYLP KGFLNQFTED KPTLNFFYQQ VKSDYMLEIA

161 DQVDQEIALK LGCLEIRRSY WEMRGNALEK KSNYEVLEKD

201 VGLKRFFPKS LLDSVKAKTL RKLIQQTFRQ FANLNREESI

241 LKFFEILSPV YRFDKECFKC ALGSSWIISV ELAIGPEEGI

281 SYLTDKGCNP THLADFTQVQ TIQYSNSEDK DRKGMLQLKI

321 AGAPEPLTVT APSLTIAENM ADLIDGYCRL VNGTSQSFII

361 RPQKEGERAL PSIPKLANSE KQGMRTHAVS VSDEISGDET

401 DDYAEIIDEE DTYTMPSKSY GIDEARDYEI QRERIELGRC

441 IGEGQFGDVH QGIYMSPENP ALAVAIKTCK NCTSDSVREK

481 FLQEACLKLP GDKDHVCFAH HSILSVLHST
```

A FAK protein with a P116C mutation is shown below as SEQ ID NO: 28.

```
  1 MAAAYLDPNL NHTPNSSTKT HLGTGMERSP GAMERVLKVF
 41 HYFESNSEPT TWASIIRHGD ATDVRGIIQK IVDSHKVKHV
 81 ACYGFRLSHL RSEEVHWLHV DMGVSSVREK YELAHCPEEW
121 KYELRIRYLP KGFLNQFTED KPTLNFFYQQ VKSDYMLEIA
161 DQVDQEIALK LGCLEIRRSY WEMRGNALEK KSNYEVLEKD
201 VGLKRFFPKS LLDSVKAKTL RKLIQQTFRQ FANLNREESI
241 LKFFEILSPV YRFDKECFKC ALGSSWIISV ELAIGPEEGI
281 SYLTDKGCNP THLADFTQVQ TIQYSNSEDK DRKGMLQLKI
321 AGAPEPLTVT APSLTIAENM ADLIDGYCRL VNGTSQSFII
361 RPQKEGERAL PSIPKLANSE KQGMRTHAVS VSDEISGDET
401 DDYAEIIDEE DTYTMPSKSY GIDEARDYEI QRERIELGRC
441 IGEGQFGDVH QGIYMSPENP ALAVAIKTCK NCTSDSVREK
481 FLQEACLKLP GDKDHVCFAH HSILSVLHST
```

A FAK protein with a P116G mutation is shown below as SEQ ID NO: 29.

```
  1 MAAAYLDPNL NHTPNSSTKT HLGTGMERSP GAMERVLKVF
 41 HYFESNSEPT TWASIIRHGD ATDVRGIIQK IVDSHKVKHV
 81 ACYGFRLSHL RSEEVHWLHV DMGVSSVREK YELAHGPEEW
121 KYELRIRYLP KGFLNQFTED KPTLNFFYQQ VKSDYMLEIA
161 DQVDQEIALK LGCLEIRRSY WEMRGNALEK KSNYEVLEKD
201 VGLKRFFPKS LLDSVKAKTL RKLIQQTFRQ FANLNREESI
241 LKFFEILSPV YRFDKECFKC ALGSSWIISV ELAIGPEEGI
281 SYLTDKGCNP THLADFTQVQ TIQYSNSEDK DRKGMLQLKI
321 AGAPEPLTVT APSLTIAENM ADLIDGYCRL VNGTSQSFII
361 RPQKEGERAL PSIPKLANSE KQGMRTHAVS VSDEISGDET
401 DDYAEIIDEE DTYTMPSKSY GIDEARDYEI QRERIELGRC
441 IGEGQFGDVH QGIYMSPENP ALAVAIKTCK NCTSDSVREK
481 FLQEACLKLP GDKDHVCFAH HSILSVLHST
```

A FAK protein with a P116N mutation is shown below as SEQ ID NO: 30.

```
  1 MAAAYLDPNL NHTPNSSTKT HLGTGMERSP GAMERVLKVF
 41 HYFESNSEPT TWASIIRHGD ATDVRGIIQK IVDSHKVKHV
 81 ACYGFRLSHL RSEEVHWLHV DMGVSSVREK YELAHCPEEW
121 KYELRIRYLP KGFLNQFTED KPTLNFFYQQ VKSDYMLEIA
161 DQVDQEIALK LGCLEIRRSY WEMRGNALEK KSNYEVLEKD
201 VGLKRFFPKS LLDSVKAKTL RKLIQQTFRQ FANLNREESI
241 LKFFEILSPV YRFDKECFKC ALGSSWIISV ELAIGPEEGI
281 SYLTDKGCNP THLADFTQVQ TIQYSNSEDK DRKGMLQLKI
321 AGAPEPLTVT APSLTIAENM ADLIDGYCRL VNGTSQSFII
361 RPQKEGERAL PSIPKLANSE KQGMRTHAVS VSDEISGDET
401 DDYAEIIDEE DTYTMPSKSY GIDEARDYEI QRERIELGRC
441 IGEGQFGDVH QGIYMSPENP ALAVAIKTCK NCTSDSVREK
481 FLQEACLKLP GDKDHVCFAH HSILSVLHST
```

A FAK protein with a P116K mutation is shown below as SEQ ID NO: 31.

```
  1 MAAAYLDPNL NHTPNSSTKT HLGTGMERSP GAMERVLKVF
 41 HYFESNSEPT TWASIIRHGD ATDVRGIIQK IVDSHKVKHV
 81 ACYGFRLSHL RSEEVHWLHV DMGVSSVREK YELAHKPEEW
121 KYELRIRYLP KGFLNQFTED KPTLNFFYQQ VKSDYMLEIA
161 DQVDQEIALK LGCLEIRRSY WEMRGNALEK KSNYEVLEKD
201 VGLKRFFPKS LLDSVKAKTL RKLIQQTFRQ FANLNREESI
241 LKFFEILSPV YRFDKECFKC ALGSSWIISV ELAIGPEEGI
281 SYLTDKGCNP THLADFTQVQ TIQYSNSEDK DRKGMLQLKI
321 AGAPEPLTVT APSLTIAENM ADLIDGYCRL VNGTSQSFII
361 RPQKEGERAL PSIPKLANSE KQGMRTHAVS VSDEISGDET
401 DDYAEIIDEE DTYTMPSKSY GIDEARDYEI QRERIELGRC
441 IGEGQFGDVH QGIYMSPENP ALAVAIKTCK NCTSDSVREK
481 FLQEACLKLP GDKDHVCFAH HSILSVLHST
```

A FAK protein with a P116S mutation is shown below as SEQ ID NO: 32.

```
  1 MAAAYLDPNL NHTPNSSTKT HLGTGMERSP GAMERVLKVF
 41 HYFESNSEPT TWASIIRHGD ATDVRGIIQK IVDSHKVKHV
 81 ACYGFRLSHL RSEEVHWLHV DMGVSSVREK YELAHSPEEW
121 KYELRIRYLP KGFLNQFTED KPTLNFFYQQ VKSDYMLEIA
161 DQVDQEIALK LGCLEIRRSY WEMRGNALEK KSNYEVLEKD
201 VGLKRFFPKS LLDSVKAKTL RKLIQQTFRQ FANLNREESI
241 LKFFEILSPV YRFDKECFKC ALGSSWIISV ELAIGPEEGI
281 SYLTDKGCNP THLADFTQVQ TIQYSNSEDK DRKGMLQLKI
321 AGAPEPLTVT APSLTIAENM ADLIDGYCRL VNGTSQSFII
361 RPQKEGERAL PSIPKLANSE KQGMRTHAVS VSDEISGDET
401 DDYAEIIDEE DTYTMPSKSY GIDEARDYEI QRERIELGRC
441 IGEGQFGDVH QGIYMSPENP ALAVAIKTCK NCTSDSVREK
481 FLQEACLKLP GDKDHVCFAH HSILSVLHST
```

A FAK protein with a L113A/P116N/P117K mutations is shown below as SEQ ID NO: 33.

```
  1 MAAAYLDPNL NHTPNSSTKT HLGTGMERSP GAMERVLKVF
 41 HYFESNSEPT TWASIIRHGD ATDVRGIIQK IVDSHKVKHV
 81 ACYGFRLSHL RSEEVHWLHV DMGVSSVREK YEAAHNKEEW
121 KYELRIRYLP KGFLNQFTED KPTLNFFYQQ VKSDYMLEIA
161 DQVDQEIALK LGCLEIRRSY WEMRGNALEK KSNYEVLEKD
201 VGLKRFFPKS LLDSVKAKTL RKLIQQTFRQ FANLNREESI
241 LKFFEILSPV YRFDKECFKC ALGSSWIISV ELAIGPEEGI
281 SYLTDKGCNP THLADFTQVQ TIQYSNSEDK DRKGMLQLKI
321 AGAPEPLTVT APSLTIAENM ADLIDGYCRL VNGTSQSFII
361 RPQKEGERAL PSIPKLANSE KQGMRTHAVS VSDEISGDET
```

```
-continued
401 DDYAEIIDEE DTYTMPSKSY GIDEARDYEI QRERIELGRC

441 IGEGQFGDVH QGIYMSPENP ALAVAIKTCK NCTSDSVREK

481 FLQEACLKLP GDKDHVCFAH HSILSVLHST
```

A FAK protein with L113A/P116C/P117G mutations is shown below as SEQ ID NO: 34.
```
  1 MAAAYLDPNL NHTPNSSTKT HLGTGMERSP GAMERVLKVF

41 HYFESNSEPT TWASIIRHGD ATDVRGIIQK IVDSHKVKHV

81 ACYGFRLSHL RSEEVHWLHV DMGVSSVREK YEAAHCGEEW

121 KYELRIRYLP KGFLNQFTED KPTLNFFYQQ VKSDYMLEIA

161 DQVDQEIALK LGCLEIRRSY WEMRGNALEK KSNYEVLEKD

201 VGLKRFFPKS LLDSVKAKTL RKLIQQTFRQ FANLNREESI

241 LKFFEILSPV YRFDKECFKC ALGSSWIISV ELAIGPEEGI

281 SYLTDKGCNP THLADFTQVQ TIQYSNSEDK DRKGMLQLKI

321 AGAPEPLTVT APSLTIAENM ADLIDGYCRL VNGTSQSFII

361 RPQKEGERAL PSIPKLANSE KQGMRTHAVS VSDEISGDET

401 DDYAEIIDEE DTYTMPSKSY GIDEARDYEI QRERIELGRC

441 IGEGQFGDVH QGIYMSPENP ALAVAIKTCK NCTSDSVREK

481 FLQEACLKLP GDKDHVCFAH HSILSVLHST
```

A FAK protein with L113A/P116A/P117A is shown below as SEQ ID NO: 35.
```
  1 MAAAYLDPNL NHTPNSSTKT HLGTGMERSP GAMERVLKVF

41 HYFESNSEPT TWASIIRHGD ATDVRGIIQK IVDSHKVKHV

81 ACYGFRLSHL RSEEVHWLHV DMGVSSVREK YEAAHAAEEW

121 KYELRIRYLP KGFLNQFTED KPTLNFFYQQ VKSDYMLEIA

161 DQVDQEIALK LGCLEIRRSY WEMRGNALEK KSNYEVLEKD

201 VGLKRFFPKS LLDSVKAKTL RKLIQQTFRQ FANLNREESI

241 LKFFEILSPV YRFDKECFKC ALGSSWIISV ELAIGPEEGI

281 SYLTDKGCNP THLADFTQVQ TIQYSNSEDK DRKGMLQLKI

321 AGAPEPLTVT APSLTIAENM ADLIDGYCRL VNGTSQSFII

361 RPQKEGERAL PSIPKLANSE KQGMRTHAVS VSDEISGDET

401 DDYAEIIDEE DTYTMPSKSY GIDEARDYEI QRERIELGRC

441 IGEGQFGDVH QGIYMSPENP ALAVAIKTCK NCTSDSVREK

481 FLQEACLKLP GDKDHVCFAH HSILSVLHST
```

Truncations were generated through PCR using forward and reverse primers to direct truncation (Table 1).

TABLE 1

PCR forward primers for FAK truncations

| Truncation name | Secondary-structure(s) truncated | Forward primer (EcoRI restriction site underlined) | Reverse primer (XhoI restriction site underlined) |
|---|---|---|---|
| Truncation 1 | β-strand 4 | 5'-CCGGAATTCGTCTCCAGTGT GAGGGAGAAGTATGAGCTTGC TCACCCACCA-3' (SEQ ID NO: 36) | 5'-CCGCTCGAGAATTCTCAATTCAT ATTTCCACTCCTCTGGTGGGTGAG CAAG-3' (SEQ ID NO: 37) |
| Truncation 2 | β-strand 4, β-strand 5 | 5'-CCGGAATTCGTCTCCA GTGTGAGGGAGAAGTAT GAGCTTGCT-3' (SEQ ID NO: 38) | 5'-CCGCTCGAGCTCCTCTGGTGGG TGAGCAAGCTCATACTTCTC-3' (SEQ ID NO: 39) |
| Truncation 3 | β-strand 4, α-helix 2 | 5'-CCGGAATTCCTTGCTCA CCCACCAGAGGAGTGGA AATAT-3' (SEQ ID NO: 40) | 5'-CCGCTCGAGAATTCTCAATTCAT ATTTCCACTCCTCGGT-3' (SEQ ID NO: 41) |
| Truncation 4 | β-strand 4, β-strand 5, α-helix 2 | 5'-CCGGAATTCCTTGCTCA CCCACCAGAGGAG-3' (SEQ ID NO: 42) | 5'-CCGCTCGAGCTCCTCTGGTGGG TGAGCAAG-3' (SEQ ID NO: 43) |

PCR products were introduced into the pGEX-4T1 template between 5' EcoRI and 3'XhoI sites. Plasmids were purified via MiniPrep (QIAGEN, Valencia, Calif.) before sequencing. BL21 competent *E. coli* (New England Biolabs, Ipswich, Mass.) were transformed with appropriate plasmids, and IPTG-induced.

Adenovirus vector construction and production cDNA coding a seven amino acid segment from the F1 lobe of FAK (FAK-Helix, amino acids 113-119 LAHPPEE, SEQ ID NO:1) and a scrambled version of this sequence (FAK-HelixScr, HPELAPE, SEQ ID NO:23) were cloned in-frame into the MCS region of separate pShuttle-CMV vectors (Agilent, Santa Clara, Calif.) using forward primers that added 5'-NotI and reverse primers that added 3'-HindIII restriction sites:

```
FAK-Helix forward (SEQ ID NO: 44):
5'-CCGTCGACGCGGCCGCATGCTTGCTCACCCACCAGAGGAGTAA-3'

FAK-Helix reverse (SEQ ID NO: 45):
5'-TCTTATCTAGAAGCTTTTACTCCTCTGGTGGGTGAGCAAGCAT-3')

FAK-HelixScr forward (SEQ ID NO: 46):
5'-CCGTCGACGCGGCCGCATGCACCCAGAGCTTGCTCCAGAGTAA-3'

|FAK-HelixScr reverse (SEQ ID NO: 47):
5'-TCTTATCTAGAAGCTTTTACTCTGGAGCAAGCTCTGGGTGCAT-3').
```

The PCR did not use template DNA as forward and reverse primers collectively spanned the entire product. Recombinants were generated per manufacturer's protocols (AdEasy, Agilent, Santa Clara, Calif.), selected using kanamycin resistance, confirmed by sequencing, amplified in XL10-gold ultracompetent cells, purified, PacI-linearized, and transfected into HEK293 cells to produce adenoviral vectors coding for FAK-Helix (Ad-FAK-Helix, LAHPPEE, SEQ ID NO:1) and the FAK-HelixScr (Ad-FAK-HelixScr, HPELAPE, SEQ ID NO:23). Viral particles were expanded and collected per manufacturer's protocols, and passed through a Fast-Trap Adenovirus Purification and Concentration kit (EMD Millipore, Darmstadt, Germany) before reading OD at 260 nm. Viral titer was calculated as one A260 unit to 1012 viral particles with a 50:1 ratio of particles to infectious particles.

Phosphorylation

SW620 cells were transfected with Ad-FAK-Helix or Ad-FAK-HelixScr for 72 hours, trypsinized, and exposed to ambient or 15 mmHg increased pressure for 30 minutes at 37° C. in growth media in 48 well plates pacificated with 1% heat-inactivated BSA in PBS (to prevent adhesion). SW620 cells allowed to adhere to collagen-I-coated plates for 30 minutes at 37° C. were positive controls. Cells were lysed for western analysis.

Cell Proliferation

SW620 colorectal adenocarcinoma cells were seeded at $10^4$ cells/well on 96 well plates, recovered at 37° C. for 12 hours, allowed for proliferation, and counted using CellTiter 96 Aqueous One Solution Reagent as above. In adenoviral studies, SW620 cells were transfected with Ad-FAK-Helix or Ad-FAK-HelixScr 60 hours before plating on 96 well plates. For nonsurvival wound adhesion studies, cells were dyed with 10 µM Tag-it Violet proliferation and cell tracking dye (BioLegend, San Diego, Ca), or equivalent amounts of DMSO vehicle.

FAK-Akt1 Coimmunoprecipitation

Coimmunoprecipitations were performed as described by Craig et al. (Am J Physiol Cell Physiol 293:C1862-74 (2007)) using mouse monoclonal antibodies to Akt1 (CST, Beverly, Mass.) and HA (Convance, Berkley, Calif.).

Wound Implantation

SW620 colorectal adenocarcinoma cells were transfected with Ad-FAK-Helix or Ad-FAK-HelixScr. After 72 hours, cells for nonsurvival studies were trypsinized and dyed with 10 µM Tag-it Violet (BioLegend, San Diego, Ca) per manufacturer's protocols; survival studies used undyed cells. Cells were incubated for 30 minutes at 37° C. under ambient or 15 mmHg increased pressure in a 48 well plate pacificated with 1% heat inactivated BSA in PBS to prevent adhesion to the plate. These cells were then collected and washed in warm PBS. In nonsurvival studies, 1 cm groin incisions were made bilaterally in 6-7 week old 22.9-24.2 gram male BALB/cAnNHsd mice (Envigo, Haslett, Mich.) anesthetized i.p. with ketamine (100 mg/kg), xylazine (10 mg/kg), and acepromazine (3 mg/kg). In survival studies, a single 1 cm groin incision was made in 6-7 week old 22.9-24.2 gram male athymic nude-Foxn1nu mice (Envigo, Haslett, Mich.) anesthetized with continuous inspired 1-2% IsoFlo (Abbott Laboratories, North Chicago, Ill.) in oxygen. A 50 µl suspension ambient or increased pressure of $5 \times 10^5$ cells was randomly applied to the wounds. After 30 minutes, the fluid was aspirated and the wounds were washed with warm phosphate buffered saline six times to remove nonadherent cells. In nonsurvival studies, the mice were euthanized following wound irrigation, and wounds were excised to quantify tumor adhesion by fluorescence-activated cell sorting (FACS). The excised wound tissue was mechanically (paired scissors) and then enzymatically (3 ml/sample collagenase incubation for 1hour at 37° C. with agitation) disaggregated before passage through a cell strainer and 20 minute room temperature incubation in BioLegend fixation buffer (BioLegend, San Diego, Ca). Fixed cells were resuspended in PBS with 5% FBS and Tag-IT dye. Fluorescence and cellular auto-fluorescence were detected using a LSR flow cytometer (BD Biosciences, San Jose, Calif.) with a filter for Pacific Blue (ex/em 410/455). In survival studies, the wounds were instead closed and followed as described (9). Animal studies were sized to yield 95% confidence with 80% power and approved by the Institutional Animal Care and Use Committee of the University of North Dakota.

Statistical Analysis

Results were compared by Student's unpaired t-test and considered statistically significant when p<0.05. All experiments were done independently at least three times unless indicated otherwise. Data are expressed as mean±SEM. Results were compared by Student's unpaired t-test and log-rank test as appropriate seeking 95% confidence. In vivo studies were analyzed by Mantel-Haenszel testing. Assays were within linear ranges.

Example 2: FRNK is not the Primary Binding Site for FAK Binding to Akt1

FRNK (FAK-related non-kinase, 67 kDa) is a segment from the COOH-terminal region of the FAK molecule, the C-terminal Focal Adhesion Targeting domain, which functions as an endogenous FAK inhibitor by competitively binding to focal contacts while lacking catalytic capability. It might have been predicted that the FRNK sequence is also important in Akt-binding. We transfected either HA-tagged wild type FAK or HA-tagged FRNK plasmids into Caco-2 cells, and incubated the resulting cell lysate with Sepharose beads conjugated to GST-Akt1 before Western blotting for HA. Passage over the GST-Akt1 column enriched the resulting eluate for HA-conjugated wild type FAK while the amount of HA-conjugated FRNK was markedly reduced by this procedure. (FIG. 1, 1 of 2 similar experiments).

Example 3: Transient Expression of FAK-NT1 Inhibits Pressure-Induced Adhesion

Figure 2:
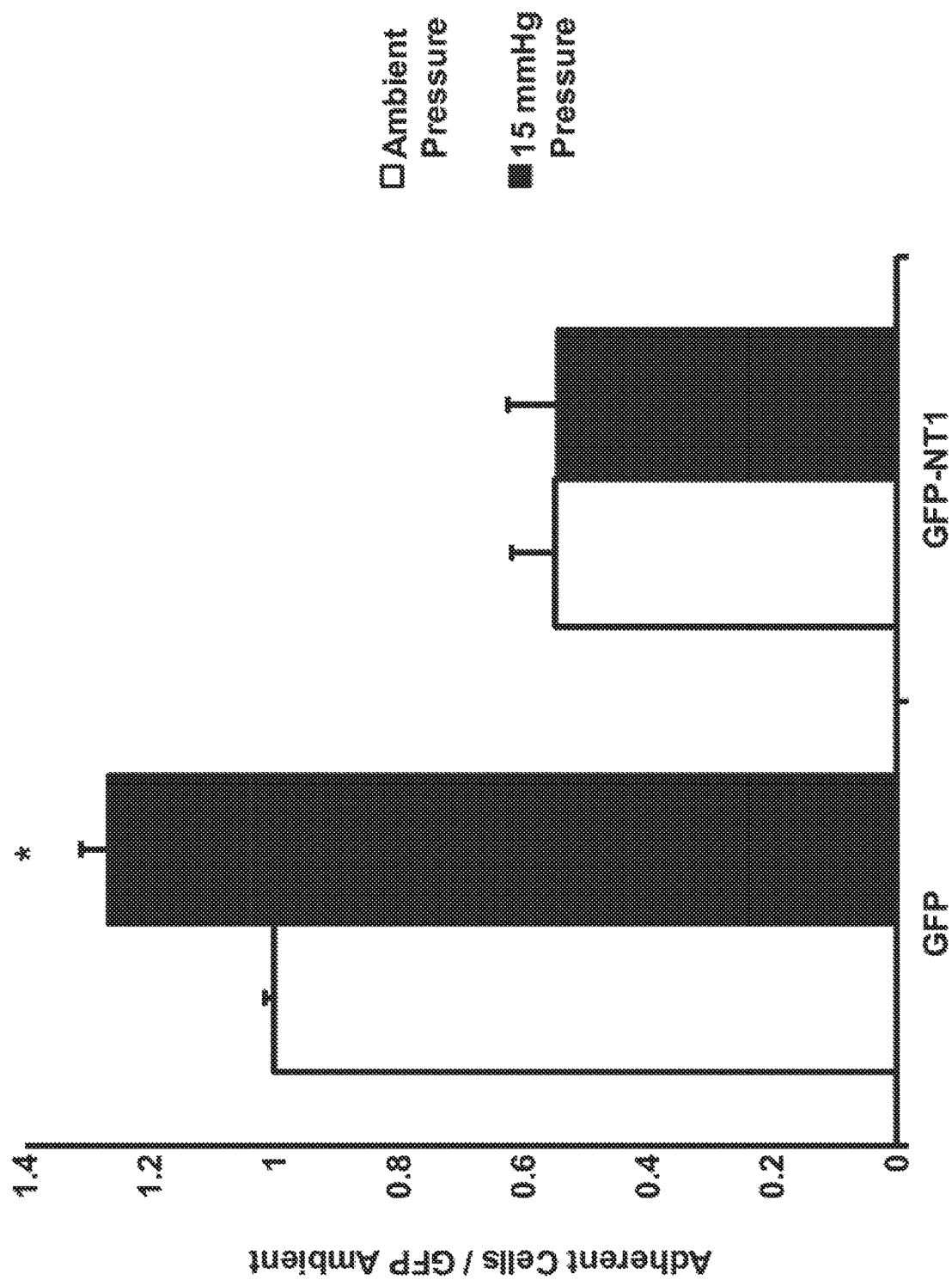
FIG. 2 illustrates that transient expression of FAK-NT1 (residues 1-126 of FAK; SEQ ID NO:3) inhibits pressure-induced adhesion. Caco-2 cells transiently expressing the GFP control demonstrated increased cell adhesion after exposure to 15 mmHg pressure. Transient expression of GFP-FAK-NT1 blocked pressure-induced cell adhesion. Decreases in basal levels of cell adhesion were also seen in the cells expressing GFP-FAK-NT1 (N=6; *$p<0.05$ vs the ambient GFP control).

In contrast, previous preliminary observations indicated that the F1 lobe of FAK (herein referred to as the NT1 region) of wild-type FAK was sufficient to pull down Akt1. To test whether this interaction of NT1 with Akt1 might have biological effects, we evaluated the effect of overexpressing NT1 in Caco-2 cells on the adhesive response to increased extracellular pressure, which requires FAK-Akt1 interaction. Caco2 cells transiently expressing the GFP-FAK-NT1 construct were therefore exposed to ambient or 15 mmHg increased pressure for 30 minutes. Pressure-induced adhesion was inhibited in the cells expressing GFP-FAK-NT1 but not in those expressing the control GFP alone (FIG. 2). Interestingly, the basal levels of adhesion were also reduced in the GFP-FAK-NT1 population.

Example 4: Inducible Expression of FAK-NT1 Inhibits Pressure-Induced Adhesion

Figure 3:
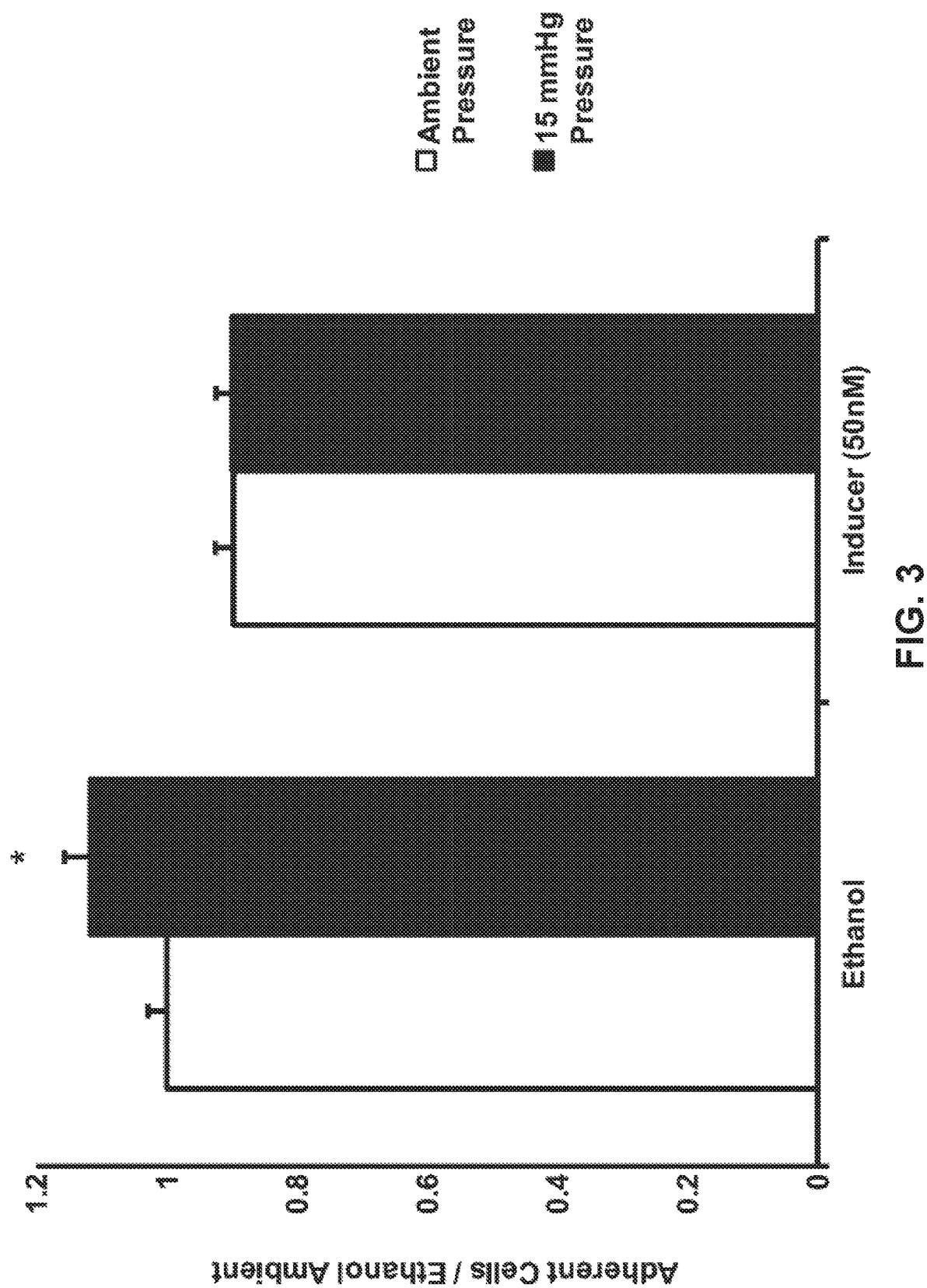
FIG. 3 illustrates that inducible expression of FAK-NT1 (SEQ ID NO:3) inhibits pressure-induced adhesion. As with the transient expression model, CT-26 cells inducibly expressing the GFP control exhibited increased cell adhesion after exposure to 15 mmHg pressure. Inducible expression of GFP-FAK-NT1 blocked pressure-induced cell adhesion (N=6; *$p<0.05$ vs the ambient GFP control).

To establish the generalizability of this phenomenon, we constructed a stable murine CT26 colon cancer line which expressed GFP-FAK-NT1 on induction with rapalog, along with a control cell line which only expressed GFP on induction. Expression of the GFP-FAK-NT1 construct in CT26 cells was induced 48 hours prior to exposure to ambient or 15 mmHg increased pressure for 30 minutes. Inducing expression of the GFP-FAK-NT1 construct prevented the stimulation of cell adhesion by increased pressure. In contrast, cells in which only GFP was inducibly expressed did display increased adhesion in response to increased extracellular pressure. (FIG. 3). Basal levels of adhesion were reduced in the GFP-FAK-NT1 population.

Example 5: The FAK-NT1-2-2 Region is Sufficient to Bind Akt1

Because the NT1 region of FAK is still quite large, we further truncated FAK-NT1 in an attempt to specify the region responsible for Akt1 binding. Five truncations were generated: NT1 (residues 1-126), NT1-1 (residues 1-60), NT1-2 (residues 61-126), NT1-1-2-1 (residues 61-93), and NT1-2-2 (residues 94-126) (FIG. 4A). The truncations that contained the 33 amino acids found in the NT1-2-2 truncation (NT1, NT1-2, and NT1-2-2) were able to pull down more significantly more Akt1 than the constructs that did not (GST, NT1-1, and NT1-2-1) (FIG. 4B-4C; $p<0.05$).

Example 6: GST-FAK Wild Type and Mutant Fusion Proteins Pull-Down Purified and Endogenous Akt1

Tests involved use of 0.3 μg of purified Akt1 in pull-down assays to approximate the Akt1 in 1,500 μg of whole cell lysate, the lysate from $1 \times 10^7$ SW620 cells previously used in similar pull-down assays. This amount (0.3 μg of purified Akt1) was selected from Western blots comparing band intensity of 0.001-0.05 μg/lane of purified Akt1 against the band intensity of 40 or 80 μg/lane of cell lysate (not shown).

Figure 6A:
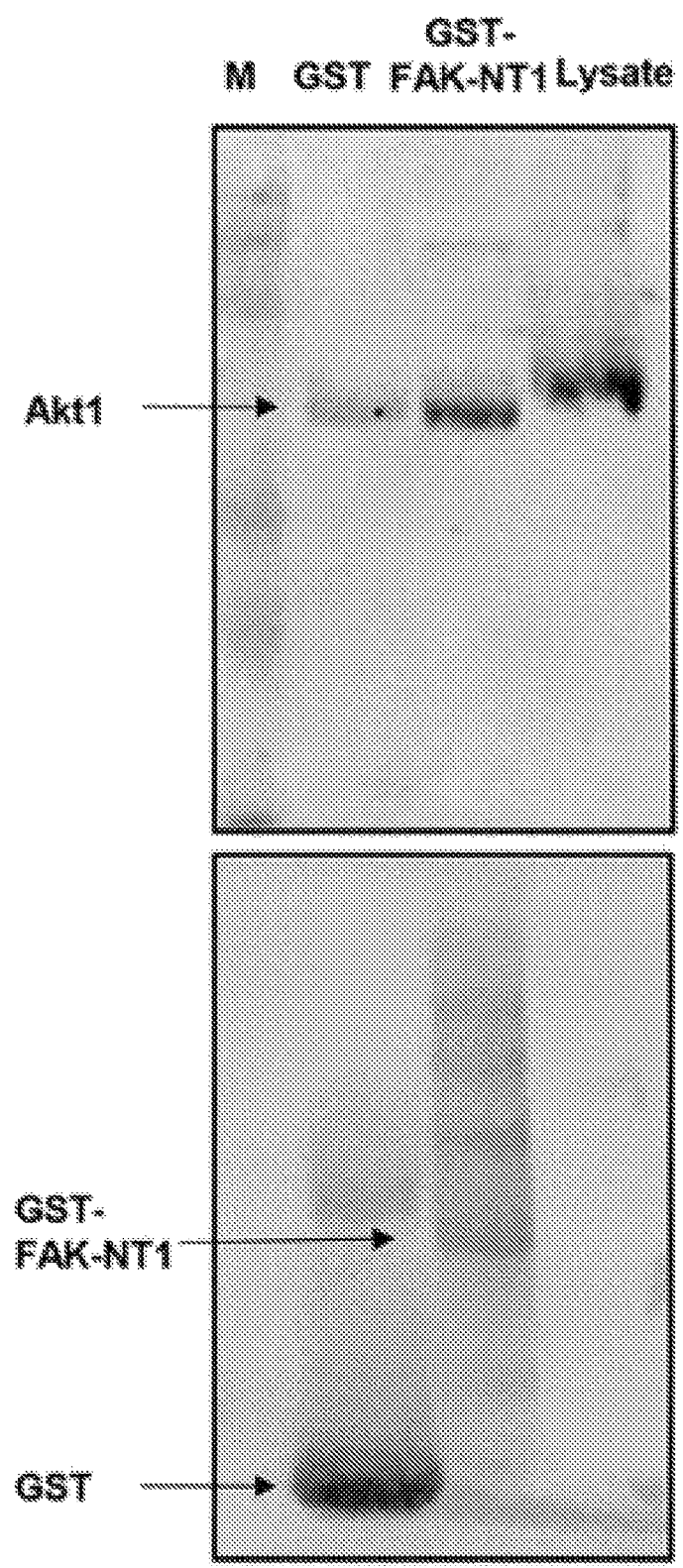
FIG. 6A-6F illustrate that FAK truncated peptides interact with Akt1.

GST-FAK-NT1-conjugated Sepharose beads pulled down Akt1 after overnight incubation with either cell lysate or purified Akt1 (FIG. 6A), indicating that FAK and Akt1 bind directly without intermediary or scaffolding proteins.

Figure 6B:
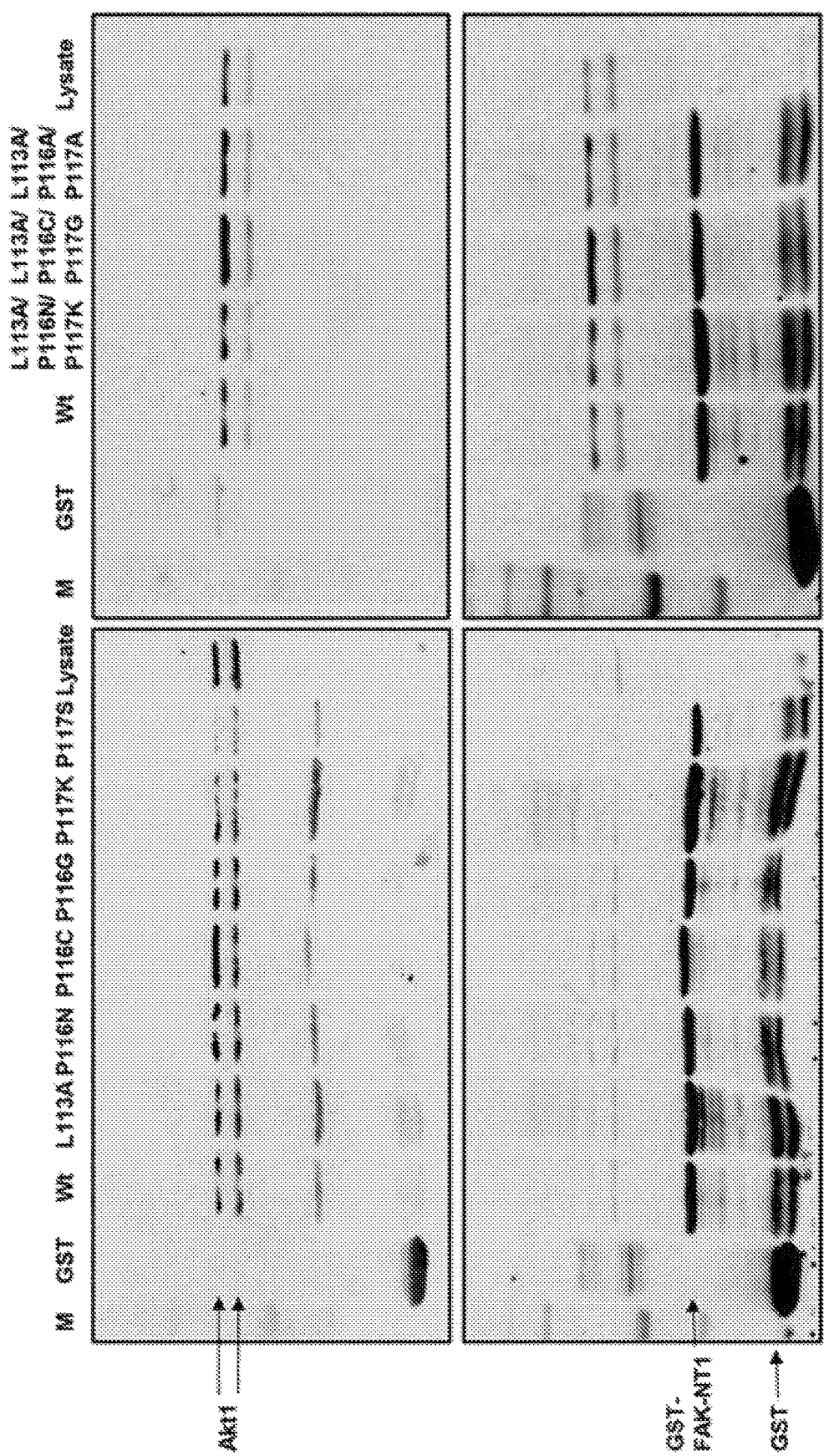

The role of a short helical secondary structure (LAHPPEE, SEQ ID NO:1) was examined using mutated variants of FAK-NT1 (FIG. 6B). FAK-NT1 is a larger truncation of FAK encompassing the NT1-2-2 region of interest; it is sufficient to pull down Akt1 and was chosen as a conservative platform that could support the native folding of the NT1-2-2 region in our mutation assays.

Figure 6C:
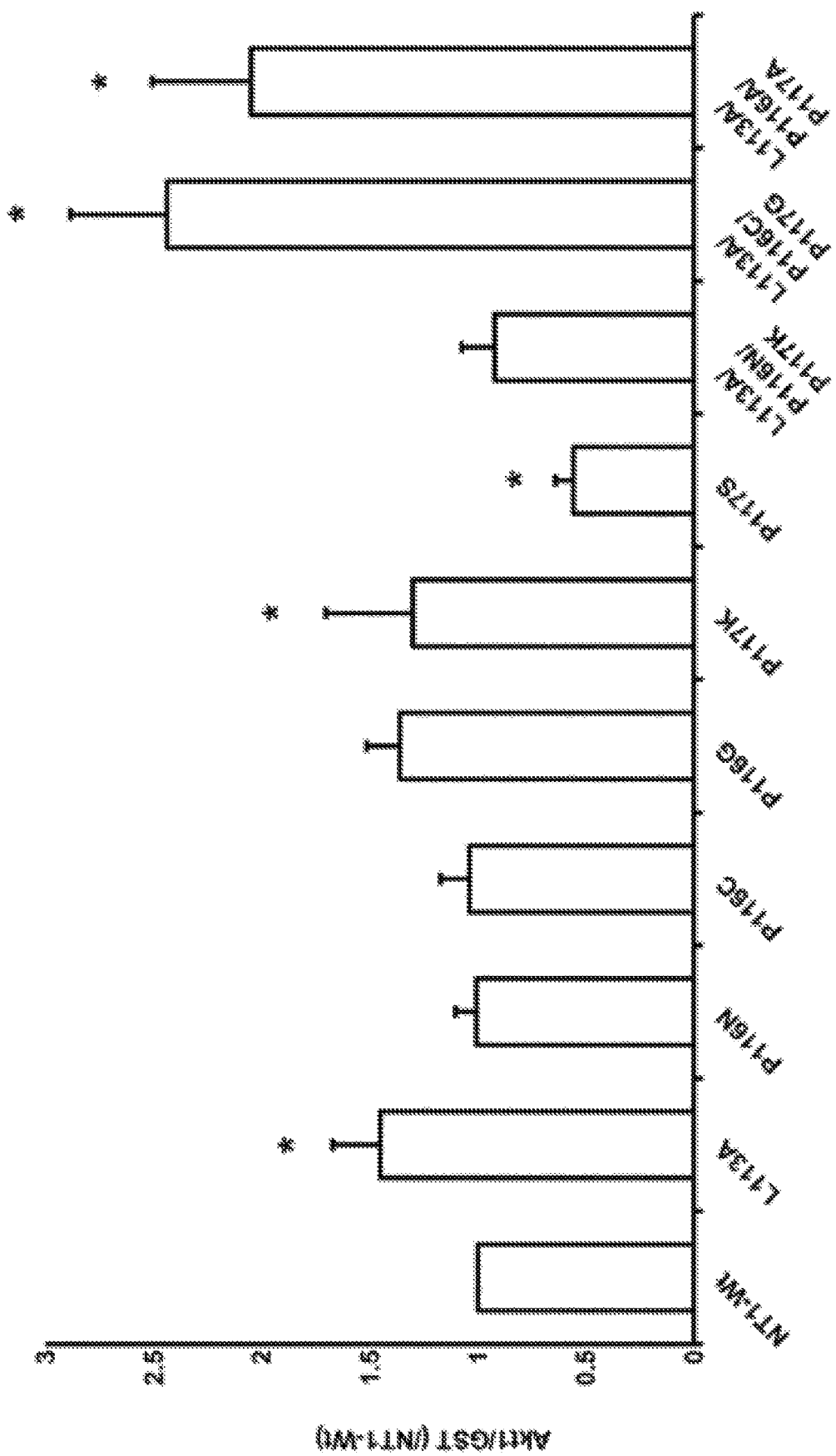

Of the nine mutants studied, Akt1 binding affinity was significantly different from that of the wild-type F1 lobe for FAK(L113A), (P116G), (P117S), (L113A/P116C/P117G), and (L113A/P116A/P117A) (FIG. 6B-6C). The FAK (P117S) mutant was designed to increase short helix rigidity and lowered Akt1 pull-down ($p<0.05$, N=11). Conversely, mutants FAK(L113A), (P116G), (L113A/P116C/P117G), and (L113A/P116A/P117A) aimed to destabilize the region and consequently increased Akt1 pull-down (FIG. 6C).

Single mutants with altered short helix hydrophobicity, FAK(P116N), (P116C), (P116G), and (P117K), did not change Akt1 pull-down except for FAK(P116G). This FAK (P116G) proline to glycine substitution intended to decrease hydrophobicity but also lowered the propensity for maintaining the wild-type helical structure by Chou-Fasman analysis. Altogether, FAK NT1 pull-down of Akt1 is altered by point mutations to this short helical region.

Figure 6D:
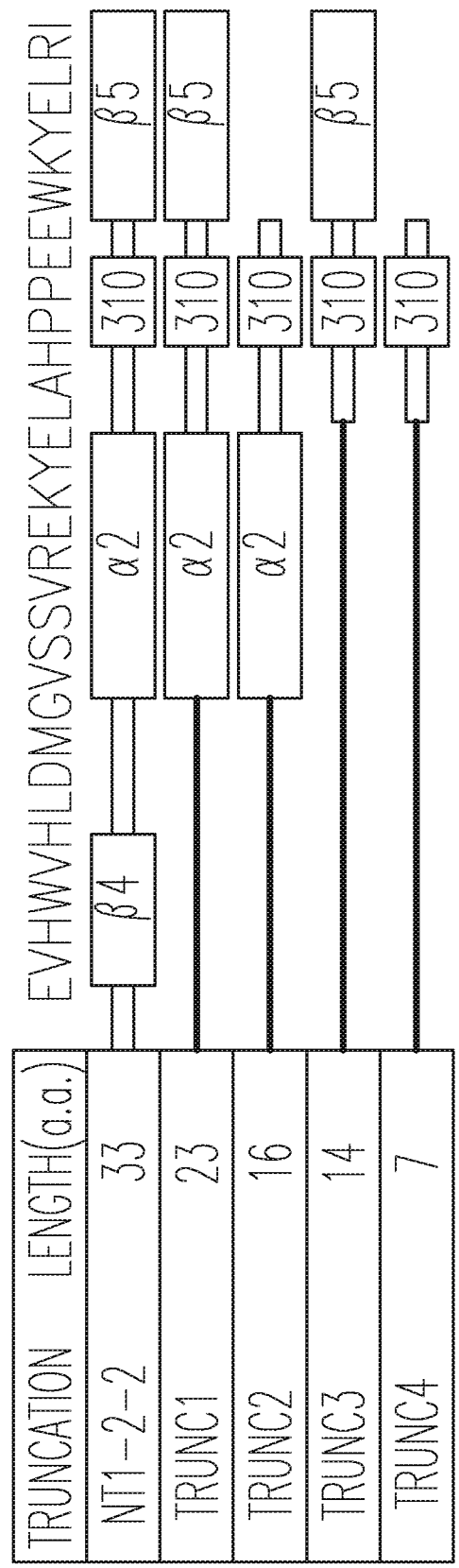
Figure 6E:
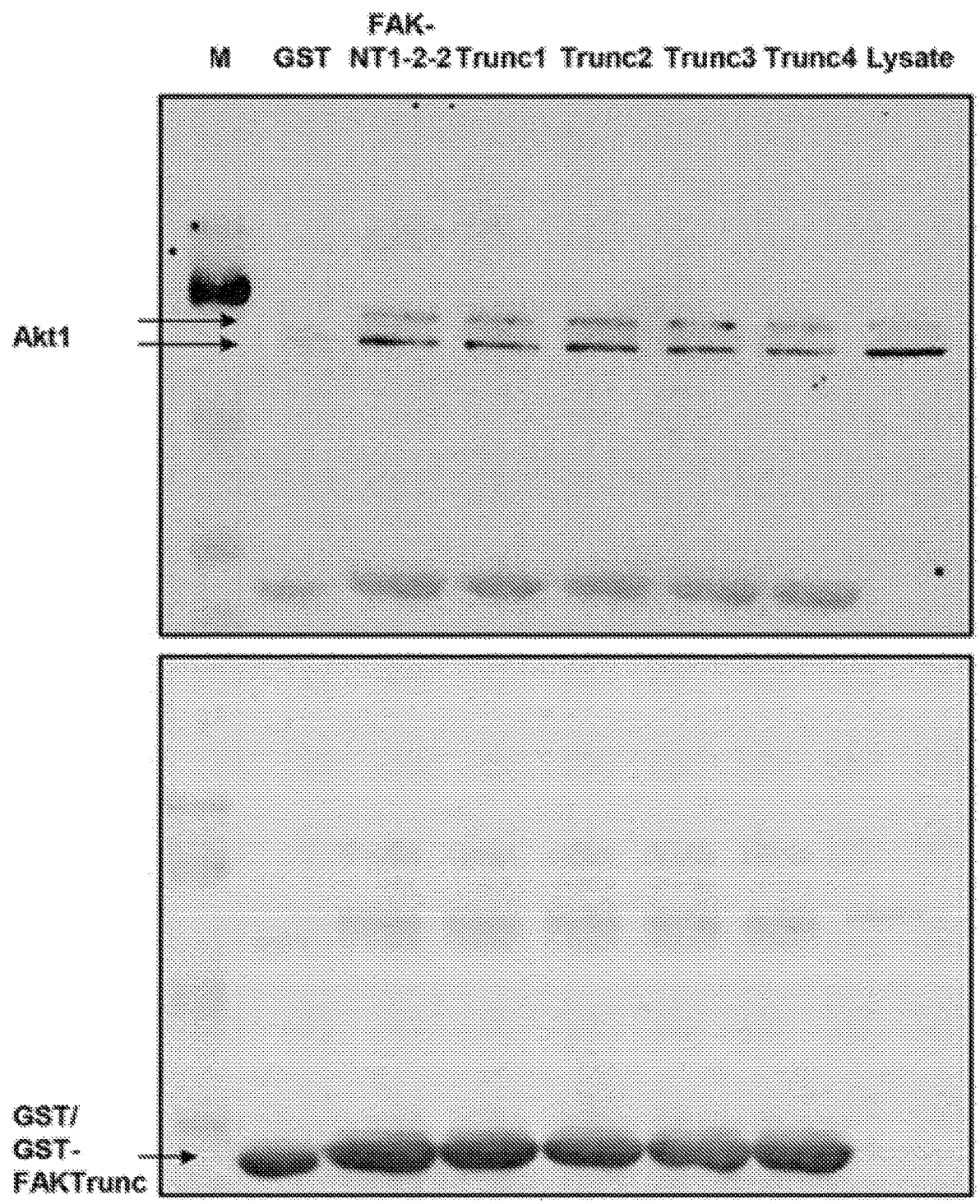
Figure 6F:
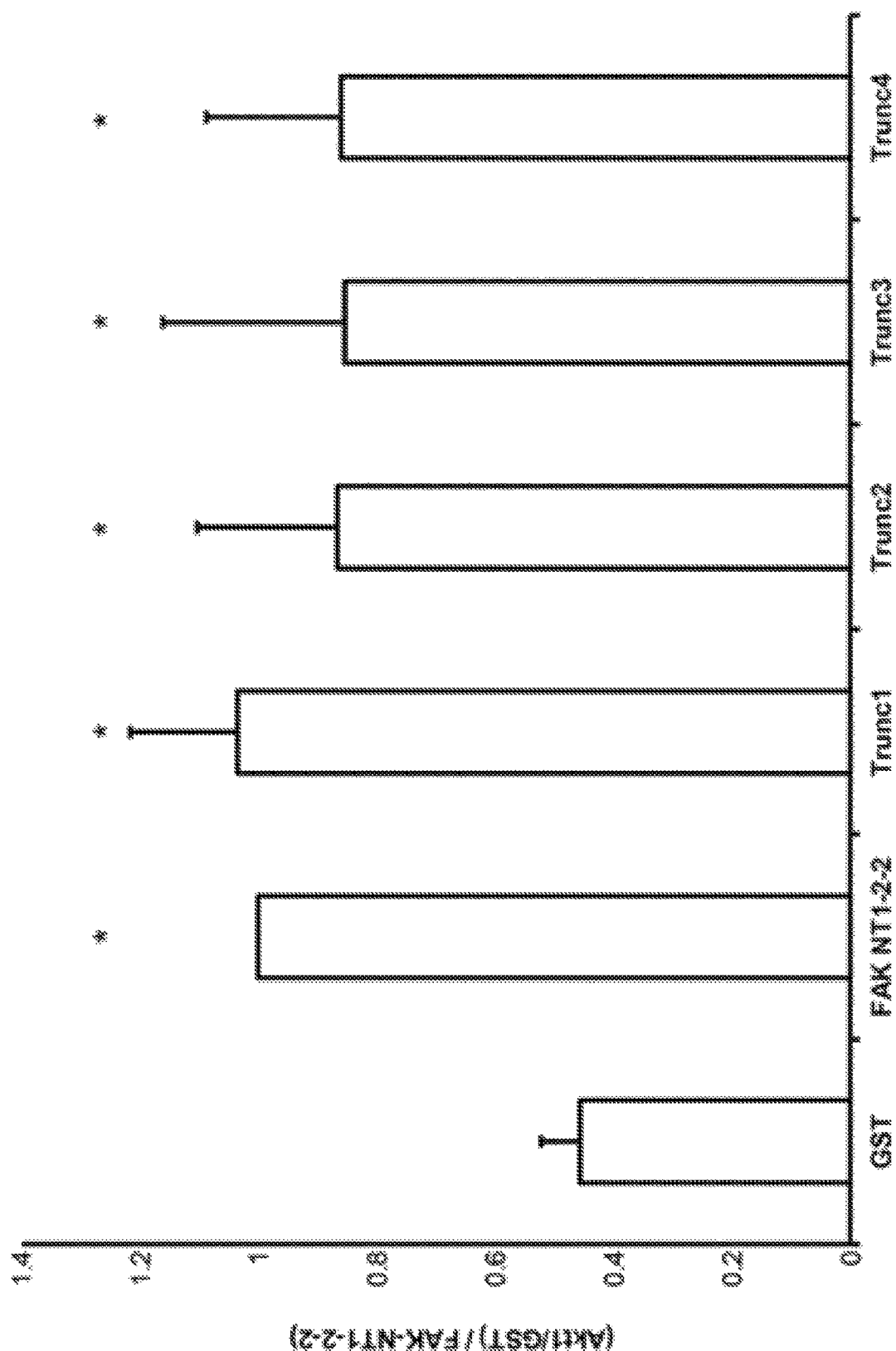

To investigate the importance of individual subdomain structures within NT1-2-2 (SEQ ID NO:2) in FAK-Akt1 binding, four variants were generated that successively excluded secondary structures in the N- and C-terminal of the short helical segment while preserving the short helix itself (FIG. 6D). These truncated versions of NT1-2-2 were challenged by Akt1 pull-down. Some non-specific GST-binding of Akt1 was observed, but NT1-2-2 pulled down much more. Truncation did not interfere with the Akt1-binding of the larger peptide (FIG. 6E).

Example 7: NT1-2-2 Derived Peptides Inhibit FAK Pull-Down of Akt1

To minimize the effect of non-specific binding to GST, a larger FAK-NT1 peptide (relative to GST) was used as bait and the effects of interference by NT1-2-2 FAK truncated peptides were assessed.

The wild-type 33 amino acid peptide (Pep-FAK-NT1-2-2) reduced binding between GST-FAK-NT1 and Akt1. A scrambled 33 amino acid control peptide containing the same amino acids in a different order (Pep-FAK-NT1-2-2Scr) did not (FIG. 7A-7B). A full length GST-FAK was used as bait to further validate the ability of the interfering peptides to block Akt1 interaction with the entire FAK molecule. Because the seven-amino acid sequence from the short helix (LAHPPEE, SEQ ID NO:1) seemed sufficient for Akt1 binding (e.g., as shown in in FIG. 6E), the focus was placed on this seven amino acid sequence and mutants thereof. Wild-type LAHPPEE and mutant (LAHPSEE (SEQ ID NO:17) and AAHCGEE (SEQ ID NO:19)) versions of the FAK peptide reduced Akt1 pulldown by human wild type GST-FAK in the presence of vehicle alone (FIG. 7C-7D). Neither a scrambled version of the short helix (HPELAPE, SEQ ID NO:23) nor a peptide derived from the β-strand secondary structure C-terminal adjacent to the short helix (WKYELRI) interfered with pulldown.

Example 8: Pressure Induced Phosphorylation of FAK and HA-FAK Inhibits Akt1 Coimmunoprecipitation Adenoviral vectors were created to deliver the wild type peptide (with sequence LAHPPEE, SEQ ID NO:1; also called Ad-FAK-Helix) or a peptide with a scrambled sequence (HPELAPE (SEQ ID NO:23); called Ad-FAK-HelixScr) into intact human SW620 colon cancer cells. q-RT-PCR analysis of the helical and scrambled peptide messages indicated similar expressions in infected cells (not shown). Pressure-induced signaling was assessed in these cancer cells that expressed either the wild type peptide or the scrambled peptide by subjecting the cells to a 15 mmHg increase in pressure.

Figure 8A:
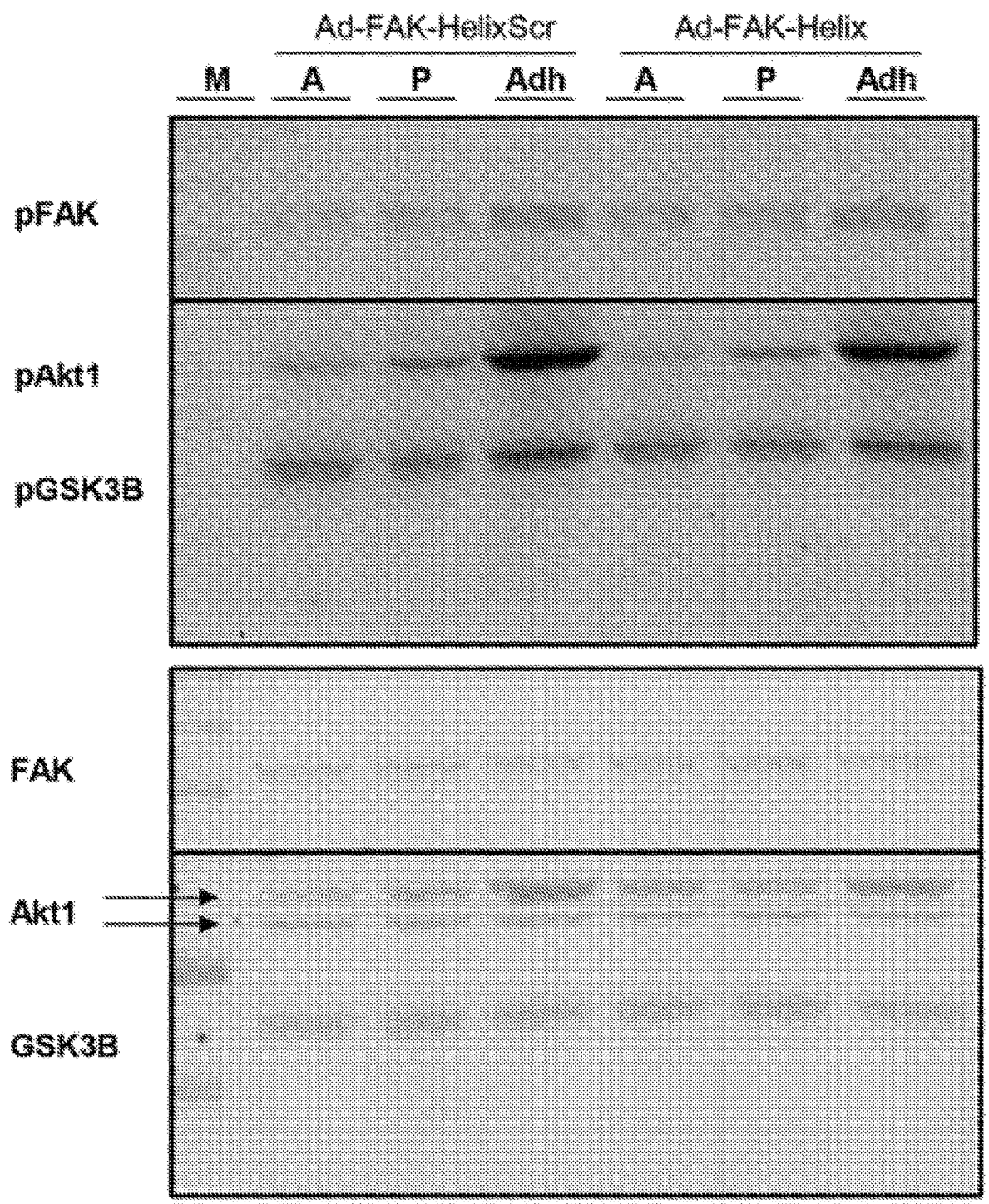
Figure 8B:
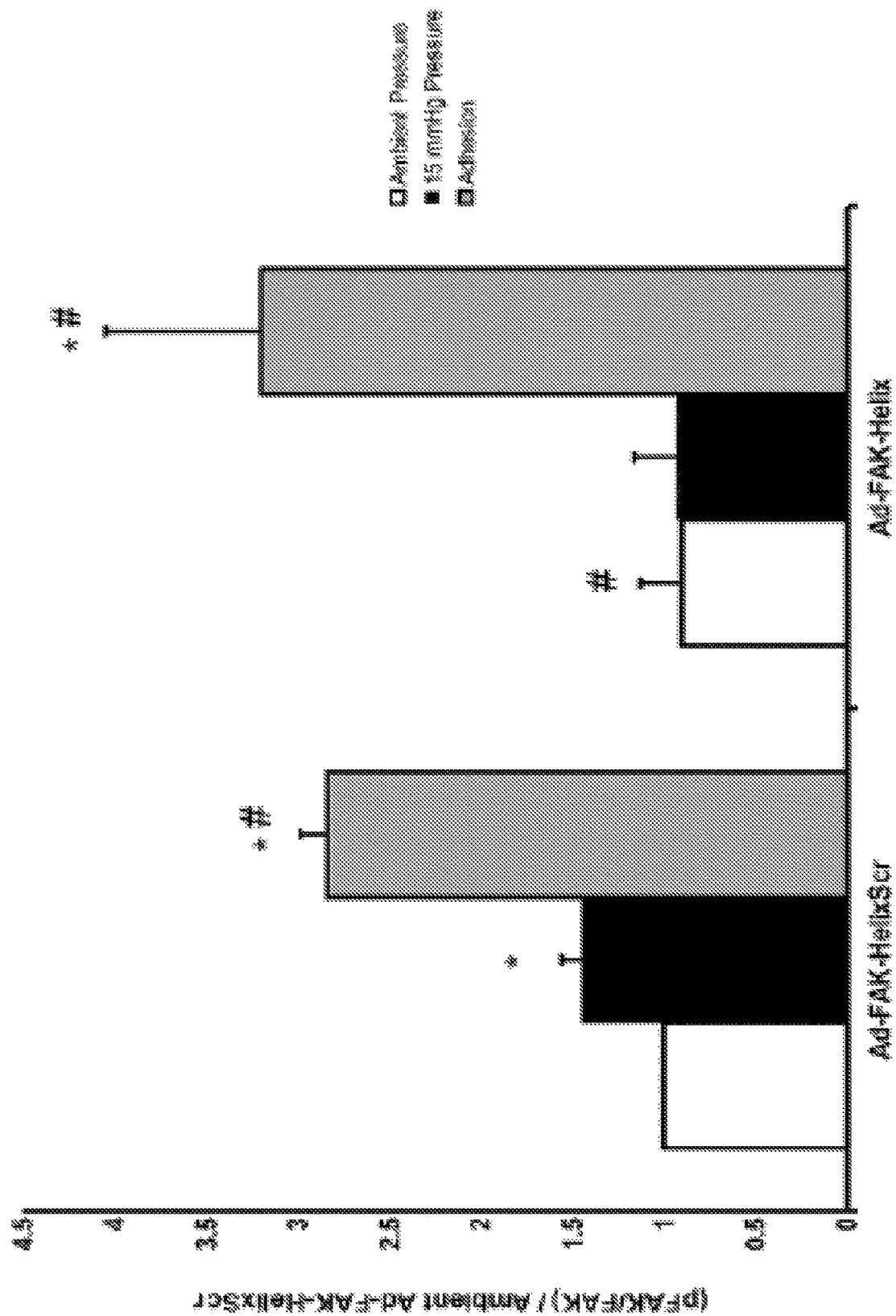

The increased pressure stimulated FAK Tyr397 phosphorylation ($145\pm10\%$) in cells infected with the scrambled Ad-FAK-HelixScr control compared to cells at ambient pressure (FIG. 8A-8B). In contrast, pressure did not stimulate FAK Tyr397 phosphorylation in cells infected with the wild type Ad-FAK-Helix peptide construct that expressed the native FAK-derived seven amino acid sequence.

Pressure-induced FAK and Akt1 phosphorylation is initiated by cytoskeletal mechanosensing in suspended cells (Thamilselvan et al., FASEB J 21:1730-41 (2007)) independent of traditional adhesion-induced signaling, which begins with surface integrin binding and progresses inward activating associated proteins. Adhesion to collagen I induced FAK Tyr397 phosphorylation in both Ad-FAK-HelixScr and Ad-FAK-Helix infected cells similarly (FIG. 8B), illustrating the specificity of the effect of LAHPPEE in inhibiting FAK-Akt1 interaction.

Figure 8C:
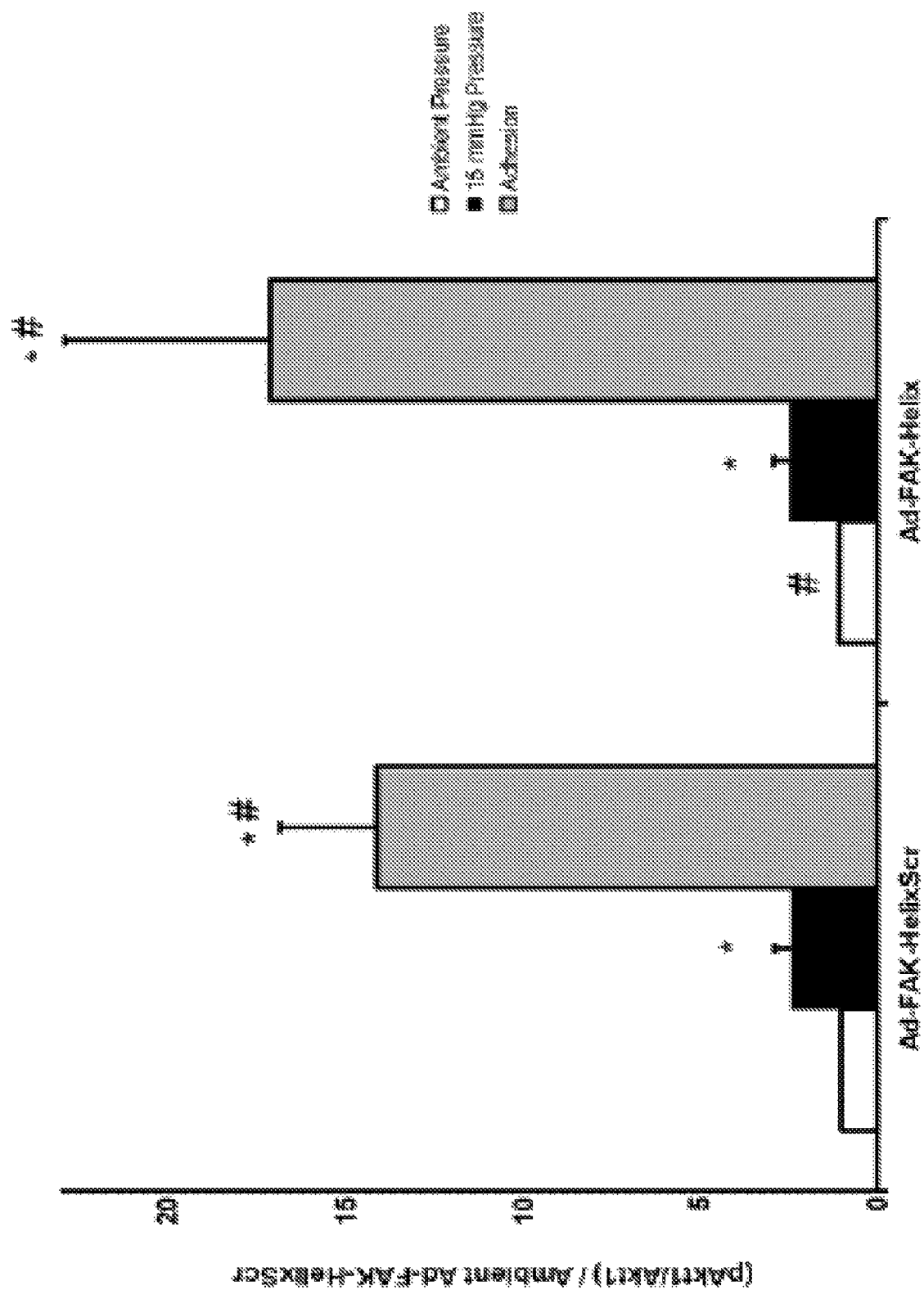

Pressure stimulates Akt1 Ser473 phosphorylation and Akt1 activation before Akt1 phosphorylates FAK. The inventors hypothesized that LAHPPEE would not interfere with other aspects of Akt1 signaling. Neither virus inhibited pressure-induced Akt1 Ser473 phosphorylation (consistent with the model that Akt1 activation by pressure occurs upstream of Akt1-FAK interaction) or adhesion-induced Akt1 Ser473 phosphorylation (FIG. 8C).

Figure 8D:
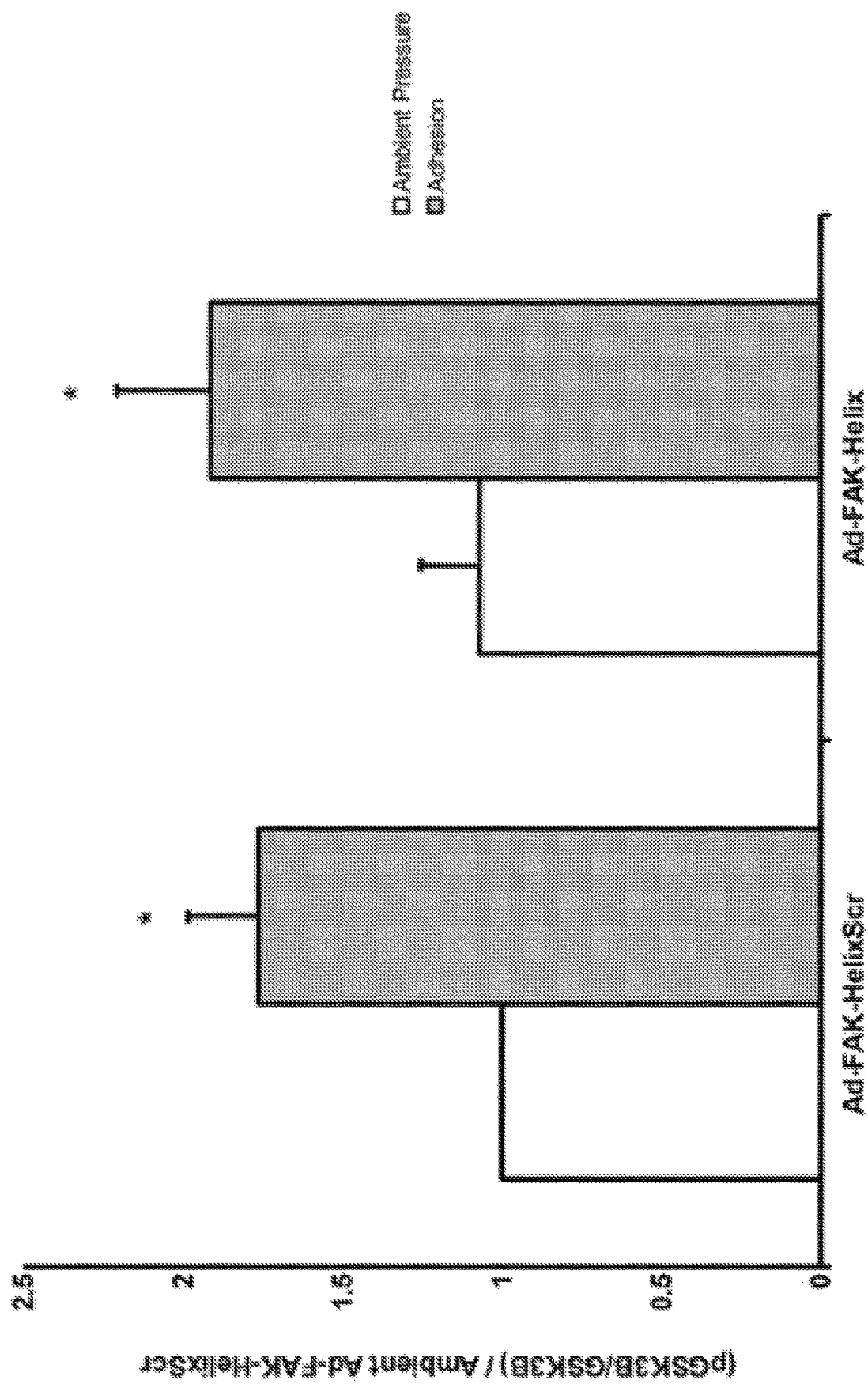

Phosphorylation of the Akt target protein GSK-3β after adhesion was examined to further evaluate the potential for peptide overexpression to modulate Akt1 downstream signaling. FIG. 8D shows that cell adhesion stimulated GSK-3β Ser9 phosphorylation similarly in Ad-FAK-HelixScr-infected and Ad-FAK-Helix-infected cells.

Figure 8F:
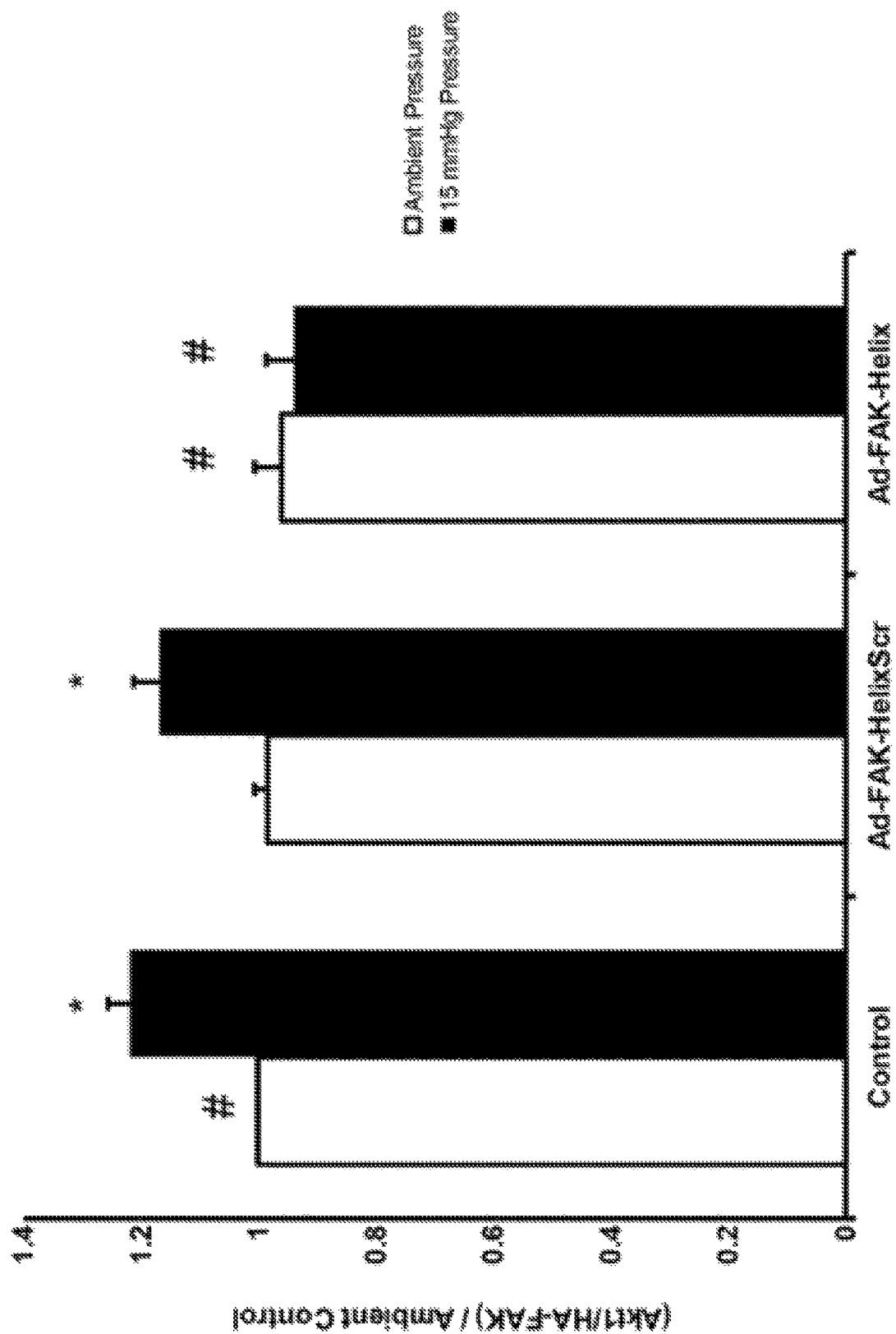

The inventors have previously demonstrated that pressure stimulates FAK-Akt1 interaction in intact SW620 cells transfected with HA-FAK before immunoprecipitation with anti-HA to amplify the signal produced by basal FAK-Akt1 interaction. Parallel studies were now performed to validate these in vitro findings within intact cells, using adenoviral infection to introduce FAK-derived peptides (FIG. 8E). Pressure increased co-precipitation of Akt1 in uninfected SW620 cells compared with cells at ambient atmospheric pressure. Infection with Ad-FAK-Helix blocked this effect. Expression of the scrambled Ad-FAK-HelixScr peptide did not block the increase in Akt1 co-precipitation (FIG. 8F).

Example 9: FAK-Derived Peptide Overexpression Prevents Pressure-Induced SW620 Cell Adhesion but does not Affect Proliferation The inventors hypothesized that peptide overexpression would inhibit pressure-stimulated adhesion, the downstream consequence of pressure-activated FAK phosphorylation.

To evaluate this hypothesis, equal numbers of virus-treated cells were seeded onto collagen-I-coated plates under ambient or increased pressure for 30 minutes. The plates were washed in blinded fashion to remove nonadherent cells. The remaining adherent cells were quantified by MTS assay.

Pressure-induced adhesion was inhibited by Ad-FAK-Helix infection but not by expression of the scrambled Ad-FAK-HelixScr peptide (FIG. 9A).

Figure 9B:
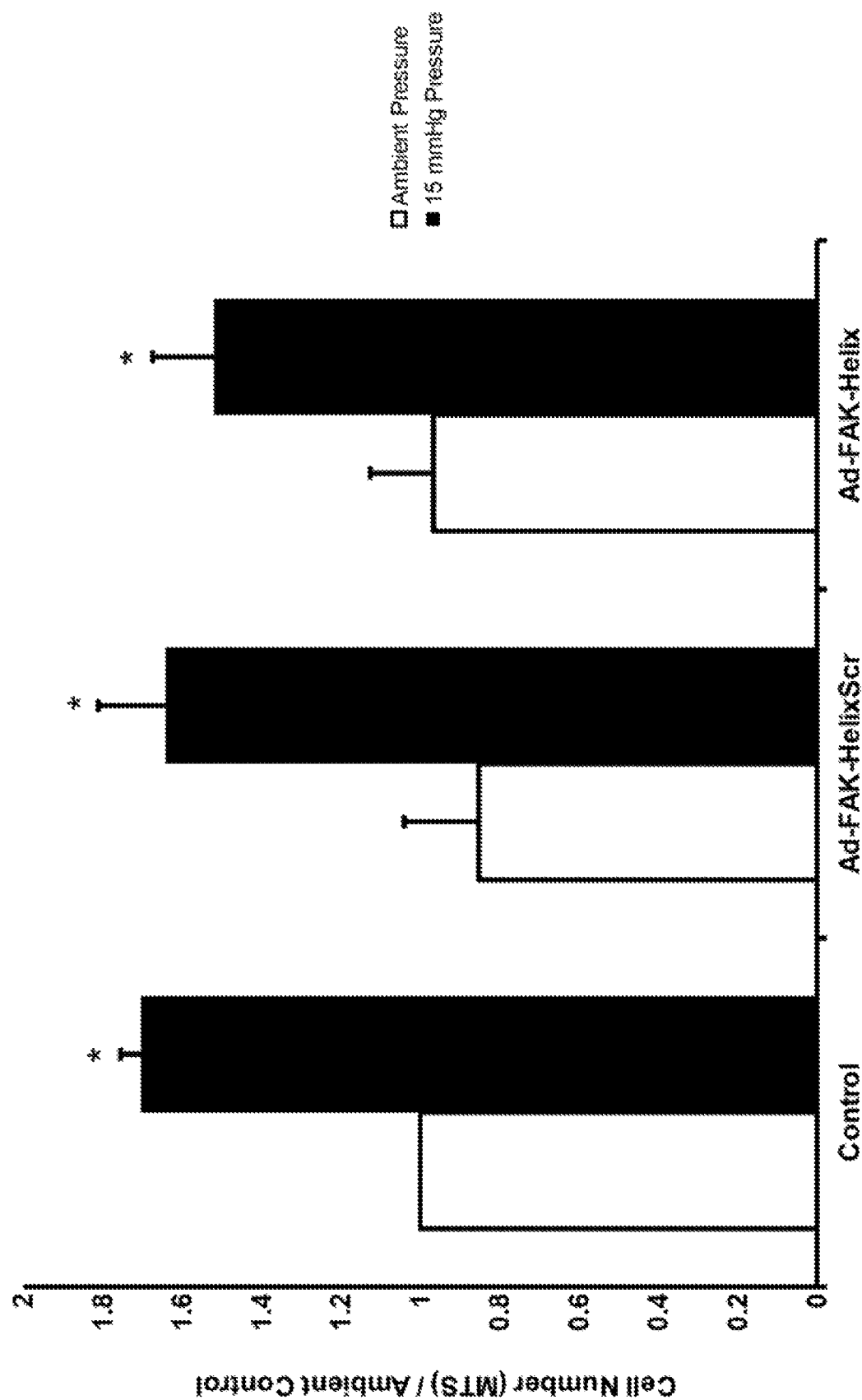

Increased pressure stimulates cancer cell proliferation. The effect of Ad-FAK-Helix on ambient and pressure-stimulated SW620 proliferation was examined to determine whether observed changes in FAK signaling and adhesion might reflect non-specific disruption of cell physiology. Neither proliferation at ambient pressure nor the mitogenic effect of increased pressure was affected by either Ad-FAK-HelixScr or Ad-FAK-Helix (FIG. 9B).

Example 10: Infection with Adenovirus Expressing FAK-Derived Peptides Inhibits Pressure-Stimulated Wound-Implantation Physiologic tissues are more complex than purified matrix proteins. Hence, SW620 cell adhesion to surgical wounds was investigated in BALB/c mice.

SW620 cells infected with either Ad-FAK-HelixScr or Ad-FAK-Helix were labeled with Tag-it Violet dye, exposed to ambient or 15 mmHg increased pressure for 30 minutes in suspension, and seeded into standardized murine surgical wounds. After 30 minutes, copious irrigation removed non-adherent cells as in surgical settings. After sacrifice and wound excision, adherent SW620 cells were distinguished from mouse tissue by fluorescence-activated cell sorting (FACS) for the Tag-it Violet dye. The dye was non-toxic and did not alter proliferation (not shown).

Figure 10:
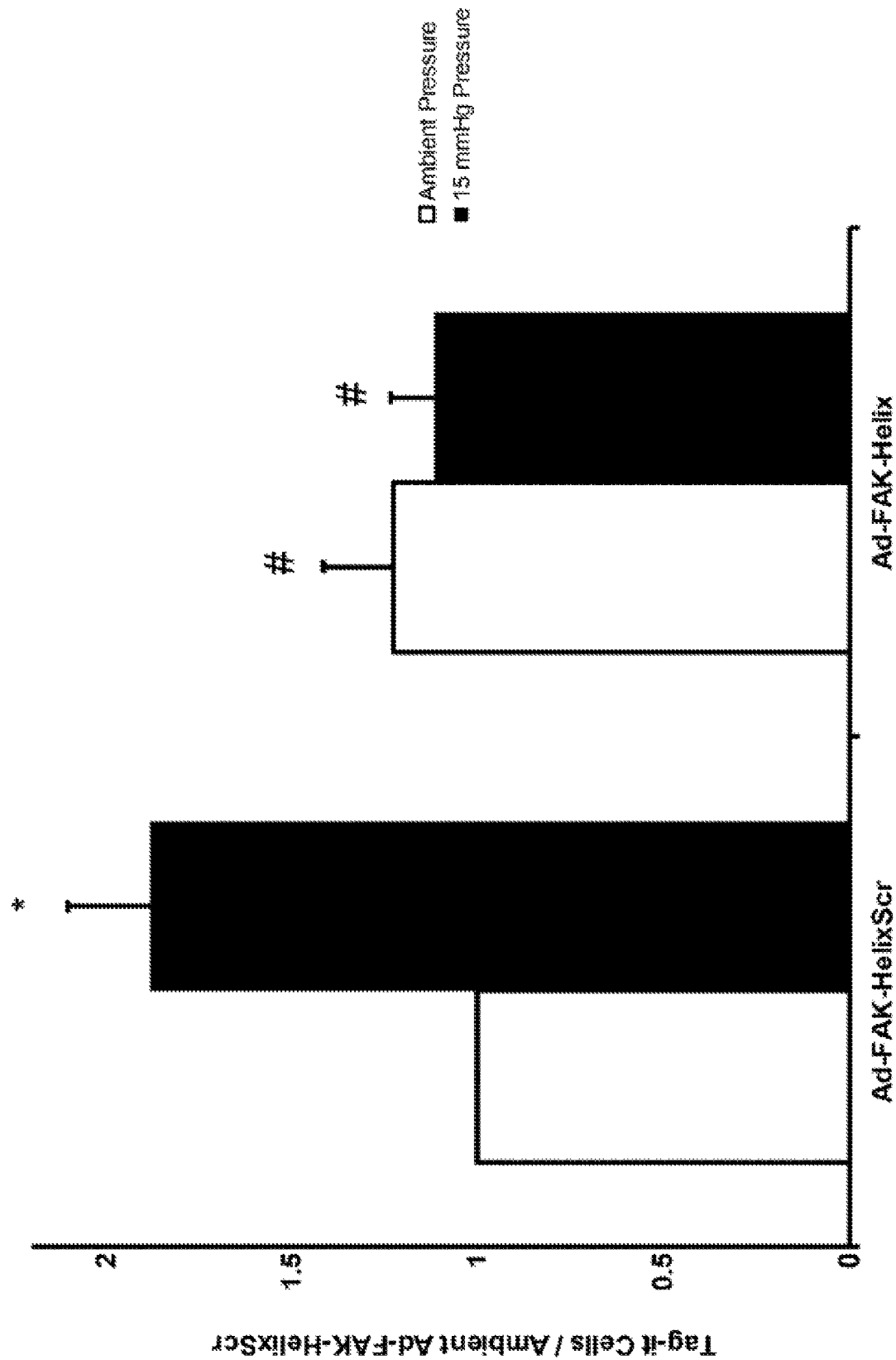
FIG. 10 graphically illustrates that FAK-derived peptides block pressure stimulation of adhesion of cancer cells to murine surgical wounds. Tag-it-labeled, Ad-FAK-HelixScr virus treated cells (expressing HPELAPE, SEQ ID NO:23) displayed increased wound implantation under elevated pressure conditions, after assay by complete excision of the wound and flow cytometric quantitation of labelled cells in wound tissues. Treatment with the Ad-FAK-Helix (LAHPPEE, SEQ ID NO:1) blocked this effect (n=14, * p<0.05 vs. the paired ambient pressure group, #p<0.05 vs. 15 mmHg Ad-FAK-HelixScr).

Pressure activation increased Ad-FAK-HelixScr-infected cell implantation into wound tissue. Ad-FAK-Helix infection blocked this effect (FIG. 10).

Example 11: Infection with Adenovirus Expressing FAK-Derived Peptide Reduces Subsequent Murine Tumor Development by Pre-Exposure of Implanted Tumor Cells to Elevated Pressure This Example describes experiments designed to investigate whether differences in cell adhesion alter tumor development.

Figure 11A:
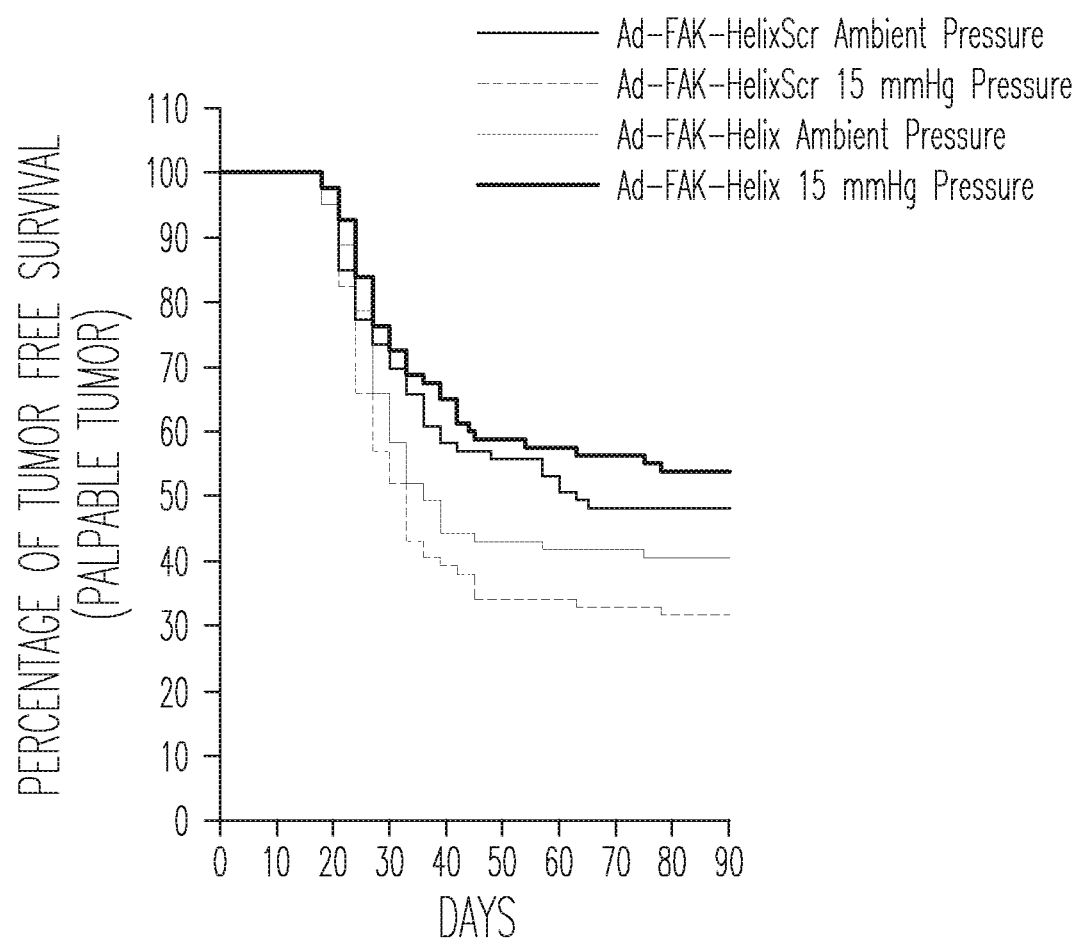
FIG. 11A-11B illustrate the effects of transient expression of a FAK-derived peptide on subsequent tumor development in a model of surgical wound occurrence. Murine tumor development and tumor-free survival were evaluated after exposing standardized surgical wounds to SW620 tumor cell suspensions for 30 minutes and then irrigating copiously before wound closure. Before implantation, the cells were infected with Ad-FAK-HelixScr (expressing HPELAPE, SEQ ID NO:23) or Ad-FAK-Helix (expressing LAHPPEE, SEQ ID NO:1) and exposed to ambient pressure or 15 mmHg increased pressure.
Figure 11B:
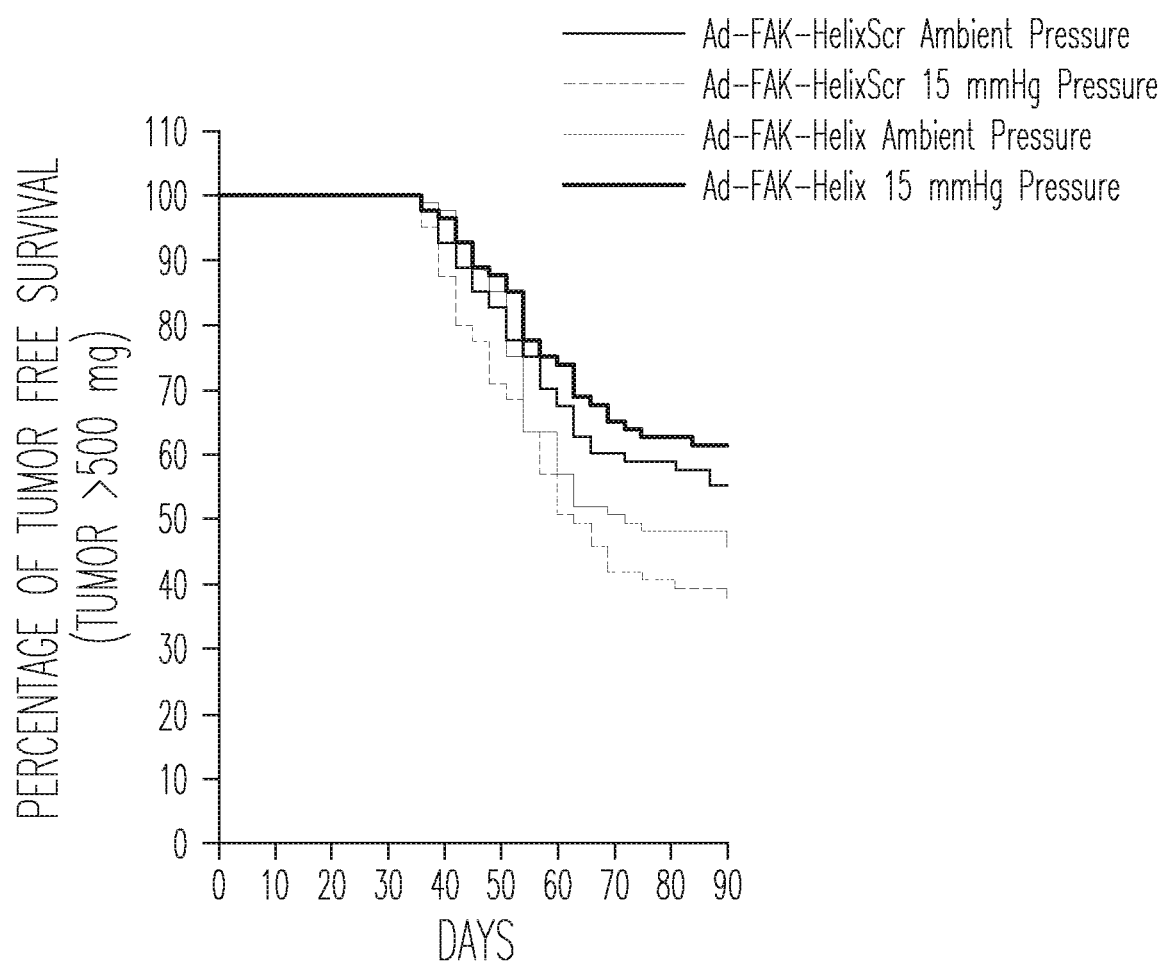

Suspended cells from each of four conditions (ambient or increased pressure, infected with Ad-FAK-HelixScr or Ad-FAK-Helix) were relabeled to blind the surgical investigator and seeded into surgical wounds in mice. After 30 minutes, the wounds were washed six times with warm PBS and closed. The mice were observed for 90 days during which time the tumors were assessed as palpable or non-palpable (FIG. 11A) and palpable tumors were measured to provide objective data (FIG. 11B). Mice were euthanized at a 500 mg tumor burden per veterinary recommendations.

In the mice implanted with Ad-FAK-HelixScr (expressing HPELAPE, SEQ ID NO:23) cells, 52% from the ambient pressure group eventually developed palpable tumors, with an average tumor-free survival time of 27 days, and a mean 500 mg tumor-burden by 58 days. In the mice that received pressure-activated Ad-FAK-HelixScr cells, 68% developed palpable tumors, and the average tumor-free survival and time to maximum tumor burden decreased to 24 and 50 days, respectively. Log-rank analysis of both the time to palpable tumor and time to 500 mg tumor burden curves demonstrated statistically significant effects of pressure pre-activation in mice that received Ad-FAK-HelixScr cells (p<0.05, N=83). See FIG. 11A-11B.

In contrast, pressure pre-activation did not worsen survival in mice that received Ad-FAK-Helix (expressing LAHPPEE, SEQ ID NO:1) cells. The mean average tumor-free survival remained at 27 days for mice receiving Ad-FAK-Helix cells previously exposed to either ambient or increased pressure. Indeed, the time till maximum tumor burden increased from 52 days in the ambient pressure group to 55 days in the increased pressure group (p<0.05, N=83) and the percentage of palpable tumors decreased (but not statistically significantly) from 60% in the ambient group to 46% in the increased pressure group. See FIG. 11A-11B.

Viral toxicity seems unlikely to explain the observed differences. Control cells were similarly infected, and Ad-FAK-Helix-infected adherent SW620 cells continued basal proliferation and responded to increased pressure with increased proliferation, similar to uninfected cancer cells. These results indicate that the Ad-FAK-Helix-infected cells' were viable and maintained their ability to respond to other mechano-transduced pathways. Because adenoviral infection was transient and cell proliferation was unaffected, neither host effects nor long-term effects on the tumor cells seem likely to contribute to the effects of peptide delivery on tumor development that were constrained to the initial adhesive event.

Therefore, expression of FAK peptides that inhibit interaction of FAK and Akt1 increase the tumor-free survival and the time till maximum tumor burden in tumor-prone mammals.

Example 12: Small Molecule Inhibition of Cell Adhesion

This Example describes identification of small molecules that inhibit FAK and Akt1 interactions.

The following compound (compound 5) with the following structure was evaluated to determine if it inhibits cell adhesion:

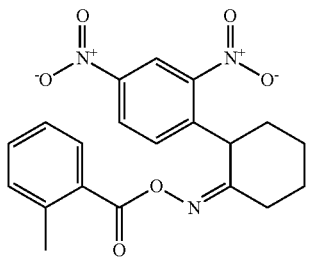

100,000 SW620 human colon cancer cells were seeded to collagen I coated 6-well plates in the presence of compound 5 (50 µM) or in the presence of DMSO (control) under ambient or increased pressure conditions for 30 minutes. Non-adherent cells were washed away, and the remainder fixed with 0.01 M NaIO4, 0.75 M lysine, 0.0375 M sodium phosphate buffer, pH 7.4, and 2% paraformaldehyde on ice for 1 hour. The adherent cells were counted microscopically in at least 20 random high-power fields per well under a fluorescent microscope.

Figure 12A:
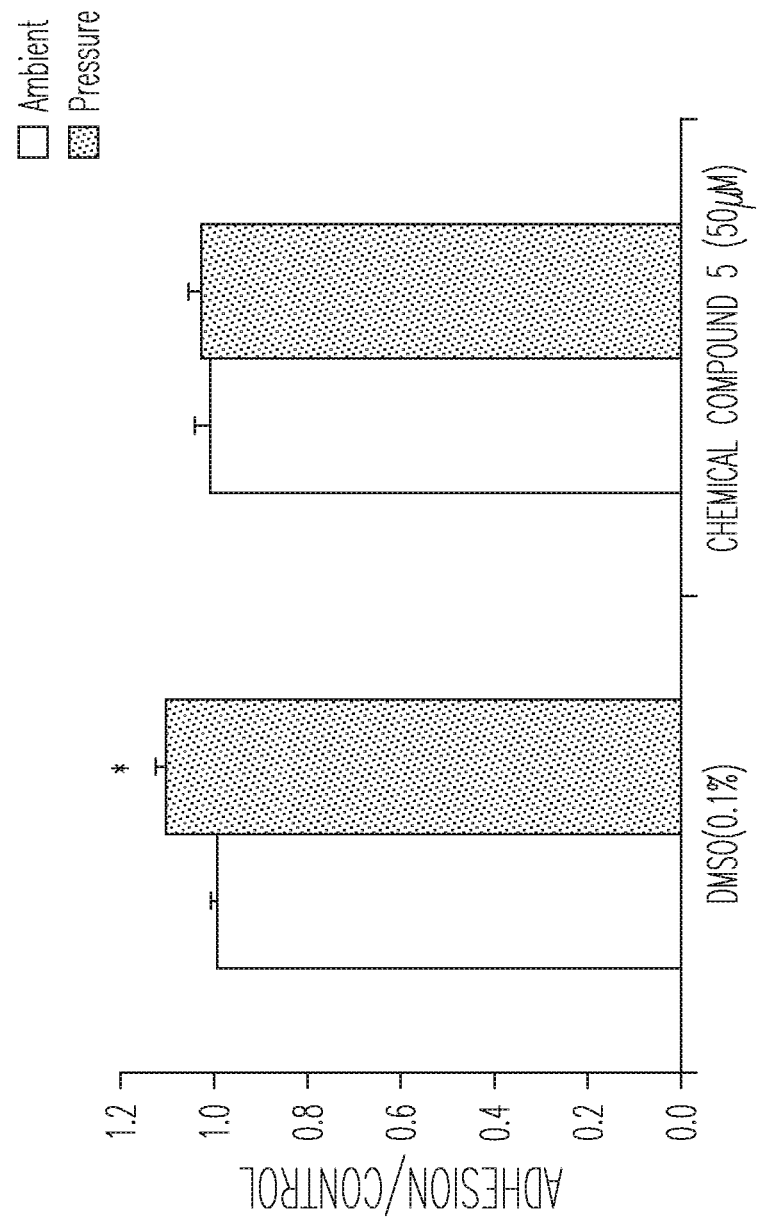
FIG. 12A-12D illustrate that compound 5 inhibits cell adhesion and phosphorylation of FAK.

As shown in FIG. 12A, compound 5 inhibited cell adhesion compared to the control without compound 5.

Example 13: Compound 5 Inhibits FAK Phosphorylation but not Akt Phosphorylation This Example describes experiments showing that compound 5 inhibits FAK phosphorylation but not Akt phosphorylation.

SW620 cells were incubated with compound 5 for 72 hours, trypsinized, and exposed to ambient or 15 mmHg increased pressure for 30 minutes at 37° C. in growth media in 48 well plates pacificated with 1% heat-inactivated BSA in PBS (to prevent adhesion). Cells were lysed for western analysis.

Figure 12B:
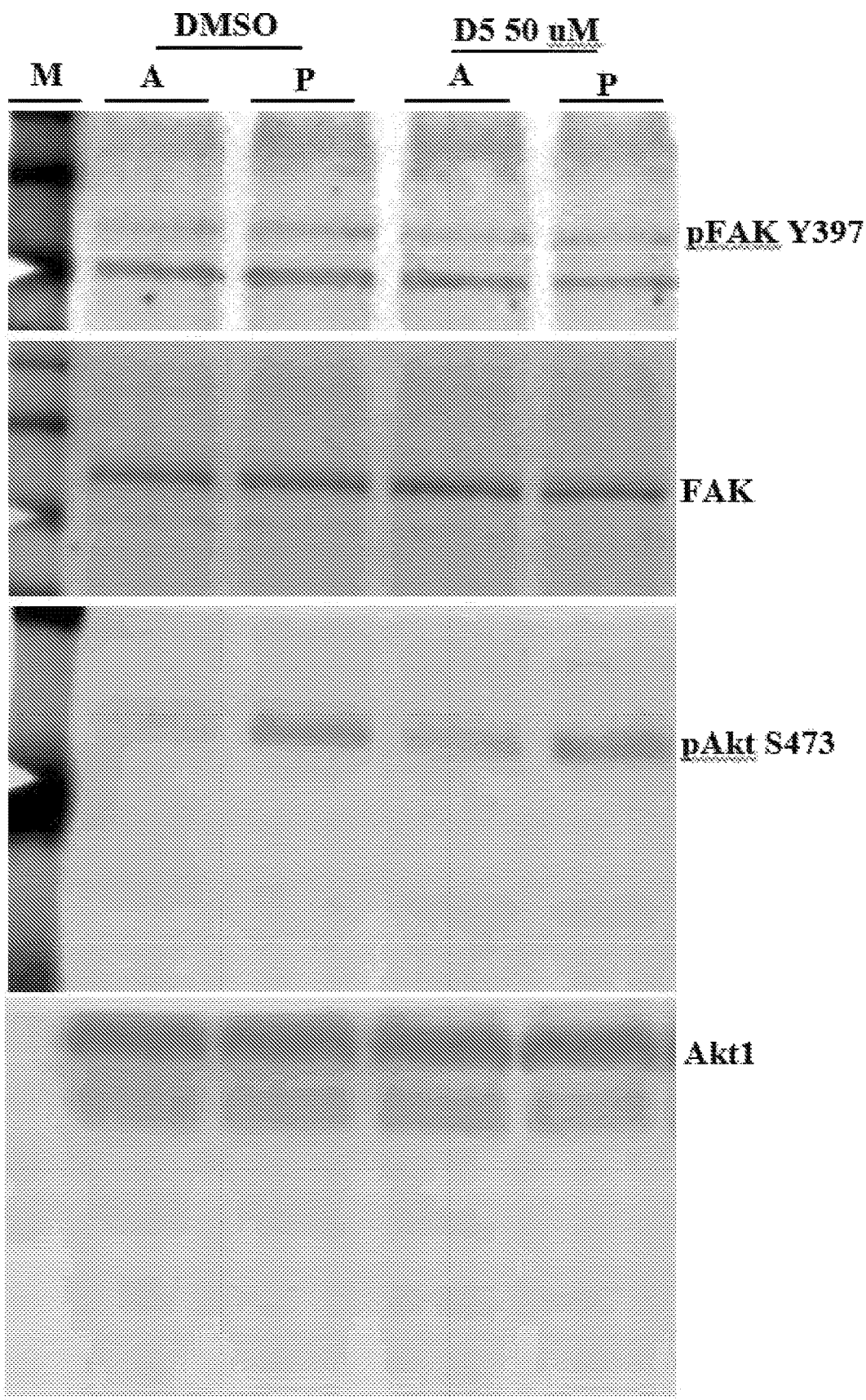
Figure 12C:
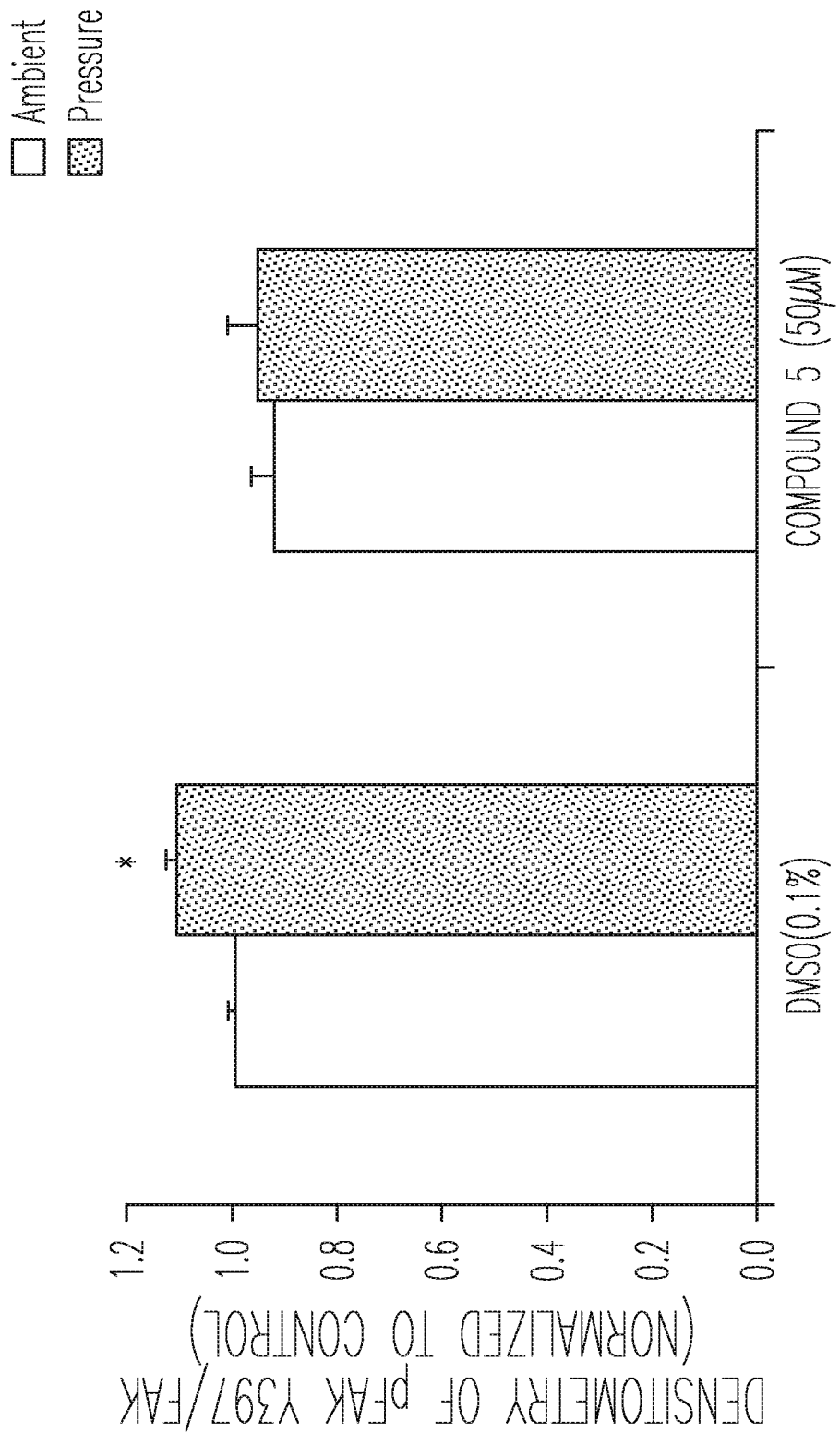
Figure 12D:
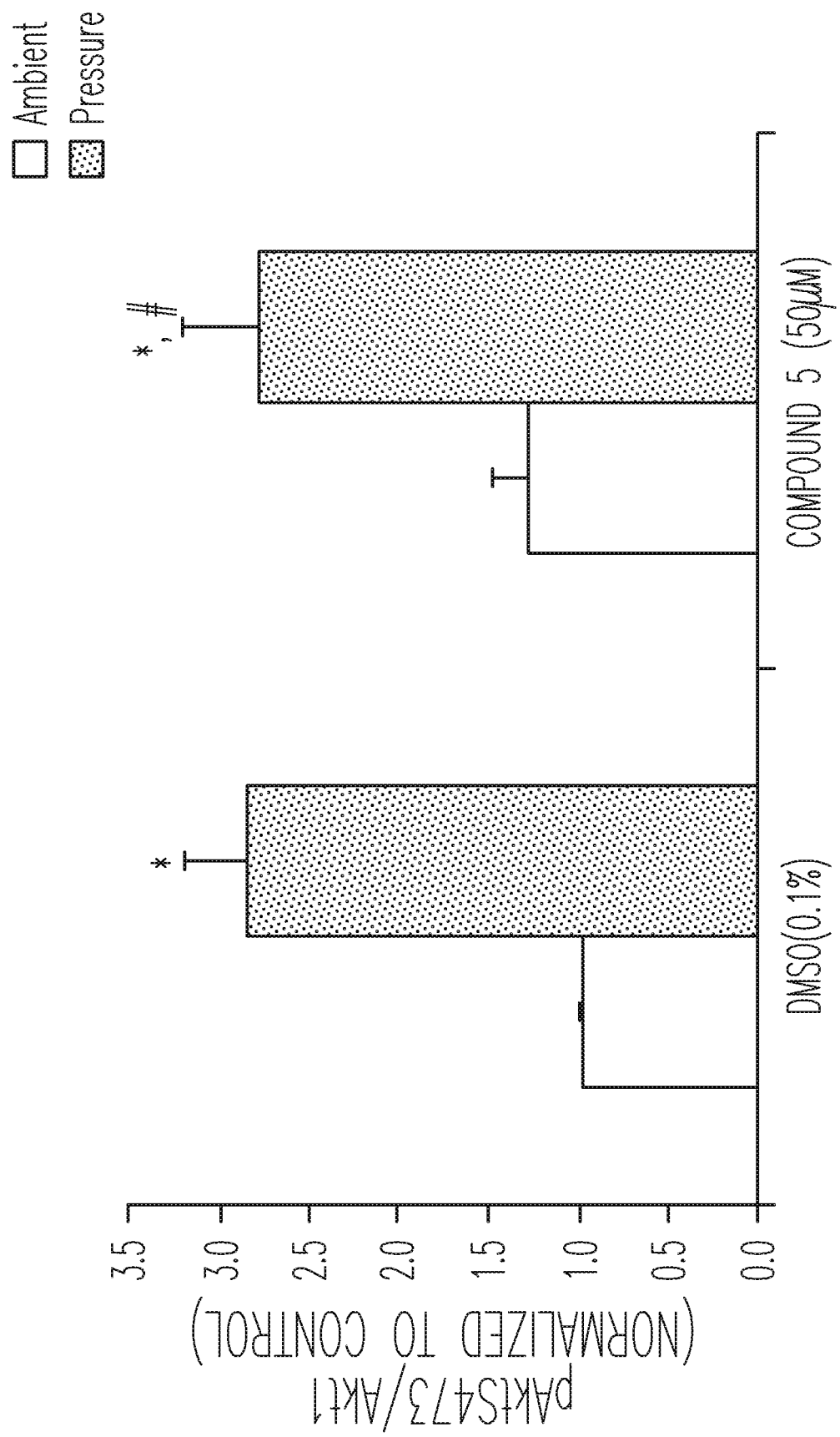

FIG. 12B shows images of western blots of cellular proteins after incubation of cells with compound 5 (D5) or DMSO (control) either at ambient pressure (A) or at 15 mmHg pressure (P). The top western blot shows phospho-FAK (pFAK, Y397), phospho-Akt1 (pAkt1, Ser473). The second western blot from the top shows total FAK. The third western blot from the top shows the amounts of pAkt1 S473. The bottom western blot shows amounts of Akt1. In each set, the blots were cut at the level of 75 kD as determined by a protein standard marker (M), and the higher weight bands were incubated with pFAK/FAK (125 kDa) antibodies while the lower weight bands received pAkt1/Akt1 (60 kDa) robes. Samples containing compound 5 or DMSO (control) were treated by exposure to ambient pressure (A), or 15 mmHg pressure (P). FIG. 12C graphically illustrates inhibition of pressure-induced FAK phosphorylation by compound 5 as evaluated by densitometric data and plotted as the percentage of phosphorylated FAK over non-phosphorylated FAK. FIG. 12D graphically illustrates that compound 5 does not inhibit pressure-induced phosphorylation of Akt at serine 473.

Example 14: Small Molecule Inhibition of Cell Adhesion

This Example describes identification of small molecules that inhibit FAK and Akt1 interactions.

Computational Screening for Small Molecule

Figure 13:
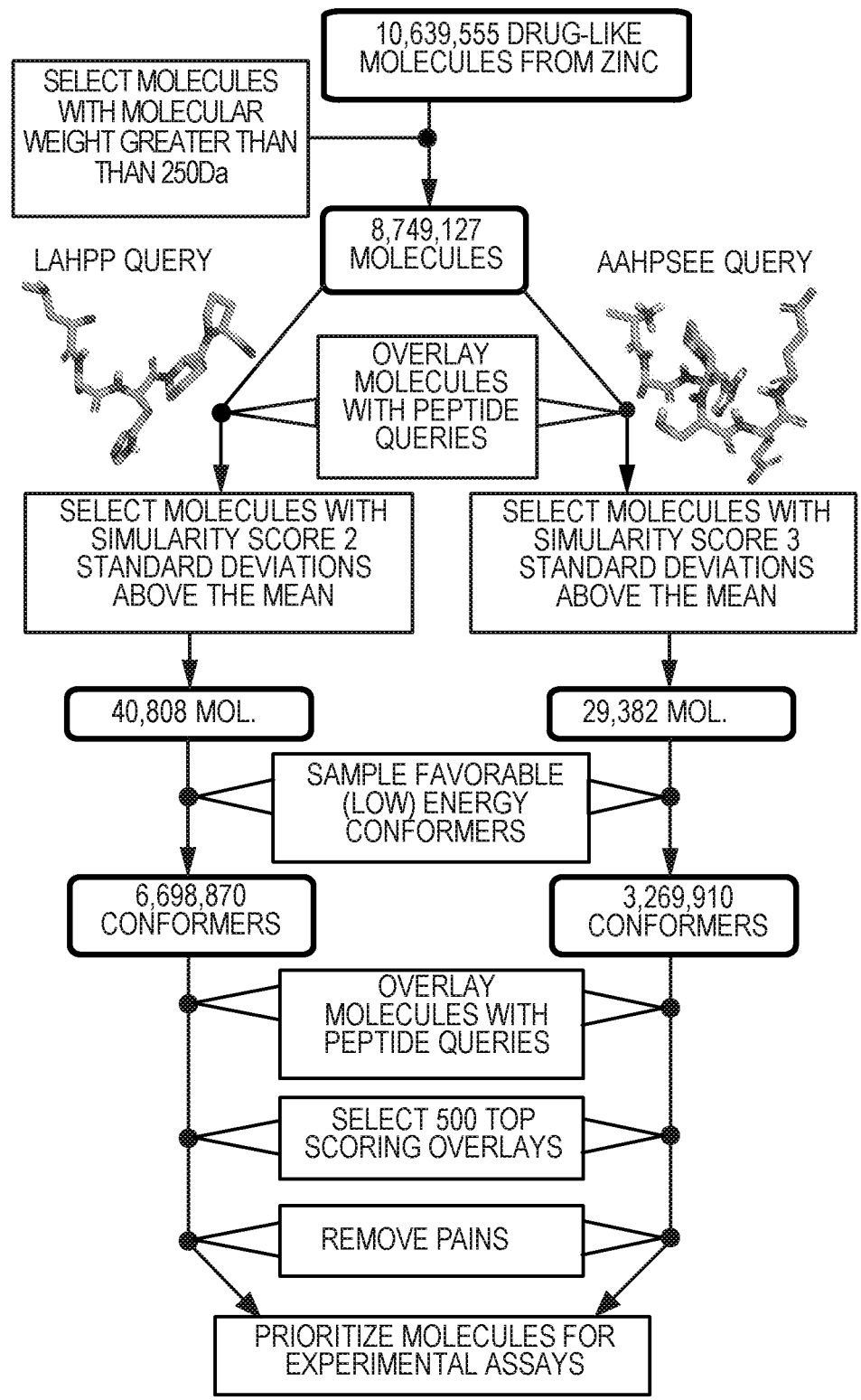
FIG. 13 illustrates a flowchart outlining a 3D ligand-based virtual screening process for identifying small-molecule mimics of epitopes from FAK.

A ligand-based virtual screening protocol was developed as illustrated in FIG. 13 to identify small-molecule mimics of a the FAK peptidyl epitope (LAHPPEE; SEQ ID NO:1) and a more helical analog (AAHPSEE, SEQ ID NO:24) that also binds AKT1 (Zeng et al., Oncotarget, 8 98051-98067 (2017)). The focus for LAHPPEE, was on the more rigid LAHPP (SEQ ID NO:25) region (helix-turn) as likely bearing a similar peptidyl structure to intact human FAK (NCBI accession number: NP 722560.1) (Jang et al., J Biol Chem 292: 16321-16332 (2017)). The 3D atomic coordinates for residues 113-117 (LAHPP, SEQ ID NO:25) were extracted from the crystal structure of FAK (PDB entry: 2a16) (Ceccarelli et al. J Biol Chem 281: 252-259 (2006)). To consider side-chain flexibility, structures reflecting eight favorable alternative positions of Leu were created with backbone-dependent rotamer sampling (Shapovalov et al. Structure 19: 844-858 (2011)) in PyMOL v. 1.8.2.2 (Schrödinger, LLC); no alternative favorable positions for His were identified. The N-terminus and C-terminus of the peptide structure were capped to a neutral state, reflecting their state within intact FAK. To enable chemical matching of polar atoms during screening, partial atomic charges were computed and assigned to the LAHPP (SEQ ID NO:25) structures using molcharge (QUACPAC v. 1.6.3.1; see website at www.eyesopen.com/quacpac; OpenEye Scientific Software, Santa Fe, N. Mex.) with the AM1BCC force-field (Jakalian et al. J Comput Chem, 23: 1623-1641 (2002). Following partial charge assignment, extra protons were removed from the C- and N-terminal nitrogen atoms, and nitrogen charges were set to −0.55, mimicking their state within FAK at physiological pH.

Figure 14A:
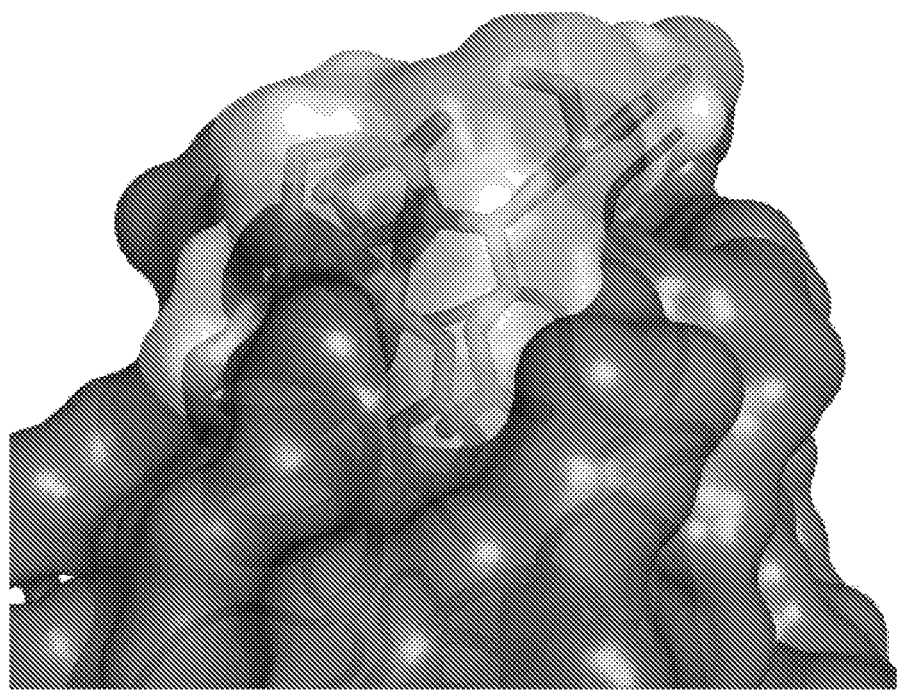
FIG. 14A-14C illustrates structures of peptide and potential small molecule inhibitors of FAK-Akt1 interactions.

The second query peptide, AAHPSEE (SEQ ID NO:24; FIG. 14A), was a two-site mutant of residues 113-119 in human FAK. In the wild-type structure, the 7-residue peptide consists of a helix terminus followed by a turn. Together they may form a continuous helical epitope upon interaction with AKT1. To test this possibility, the AAHPSEE sequence (SEQ ID NO:24) was designed as a peptide variant with greater helicity, based on the high helical propensity of Ala and the ability of Pro-Ser to form a less bent helix than Pro-Pro. Sequery (Collawn et al. Cell 63: 1061-1072 (1990)) and Superpositional Structure Assignment (Craig et al. J Mol Biol 281: 183-201 (1998)) were used to evaluate the helicity of sequences matching AAHPSEE (SEQ ID NO:24) in the Protein Data Bank (Zeng et al., Oncotarget, 8 98051-98067 (2017); Craig et al. J Mol Biol 281: 183-201 (1998); P. G. D. F. Prevelige Jr., Chou-Fasman prediction of the secondary structure of proteins, Plenum Press, N Y, 1989)). AAHPSEE (SEQ ID NO:24) was subsequently shown to effectively compete with FAK for binding to AKT1 (Zeng et al., Oncotarget, 8 98051-98067 (2017)). For 3D ligand-based screening, the structure of the AAHPSEE (SEQ ID NO:24) query was built as an alpha-helix in PyMOL (W. L. DeLano, CCP4 Newsletter On Protein Crystallography 40: 82-92 (2002)), with Ser modeled to match the wild-type Pro conformation. The structure was then energy-minimized with YASARA (see website at www.yasara.org/minimizationserver.htm; Krieger et al. Proteins, 57: 678-683 (2004)), with charges and termini handled as above for LAHPP (SEQ ID NO:25). These peptide structures were then used as queries to discover the most similar drug-like candidates for testing as potential inhibitors of FAK activation by AKT1 and pressure stimulation of cancer cell adhesion.

Figure 14B:
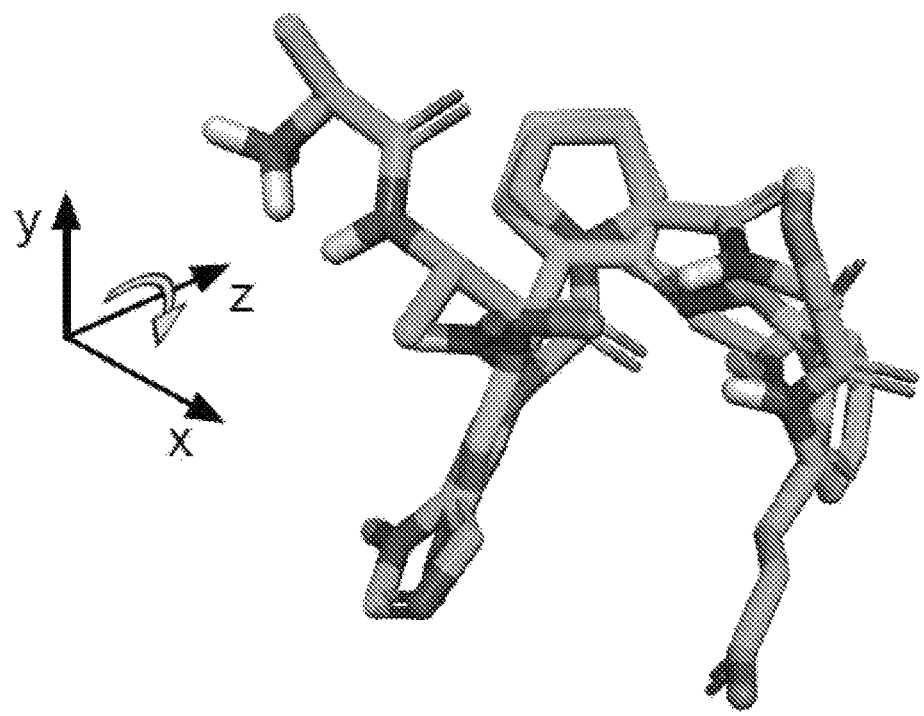
Figure 14C:
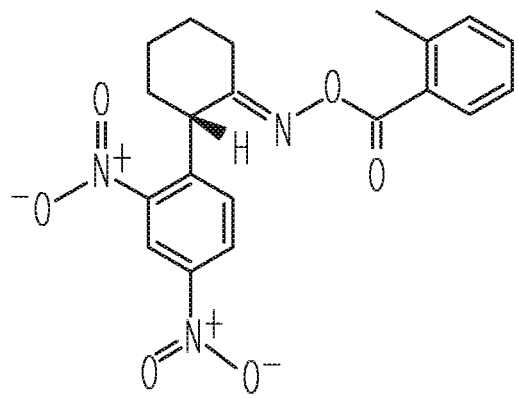

For screening, 3D structure files of 10,639,555 commercially available molecules with drug-like properties defined by the Rule of 5 (Lipinski et al., Advanced Drug Delivery Reviews, 23: 3-25 (1997)) were downloaded from ZINC (see website at zinc.docking.org; Irwin & Shoichet, J Chem Inf Model, 45 (2005) 177-182 (2005)) in MOL2 format. To test the ability of molecules from ZINC to match the known conformation and charge distribution for LAHPP (SEQ ID NO:25) and AAHPSEE (SEQ ID NO:24) peptides, up to 200 favorable 3D conformations were generated for each ZINC molecule using default settings in Omega (version 2.4.1; see website at www.eyesopen.com/omega; OpenEye Scientific Software, Santa Fe, N. Mex.; Hawkins & Nicholls, J Chem Inf Model, 52: 2919-2936 (2012)). To identify structural mimics of the FAK peptide queries, the 3D structures of the drug-like molecular conformers were overlaid on the query molecules using ROCS (version 2.4.6; see website at www.eyesopen.com/rocs; OpenEye Scientific Software, Santa Fe, N. Mex.; Hawkins et al. J Med Chem, 50: 74-82 (2007)). The 3D overlays were assessed by TanimotoCombo scoring, which equally weighs volumetric and chemical similarity. After the top-500 LAHPP (SEQ ID NO:25) and AAHPSEE (SEQ ID NO:24) mimics were identified via ligand-based screening, we removed any that were categorized as pan-assay interference compounds, using the PAINS-Remover server (see website at cbligand.org/PAINS/; Baell et al. J Med Chem, 53: 2719-2740 (2010)). Final prioritization of molecules for assays was based on visual inspection in PyMOL (W. L. DeLano CCP4 Newsletter On Protein Crystallography 40: 82-92 (2002)), evaluating the closeness of alignment between the rigid scaffold of the inhibitor candidate and the peptide backbone, and the chemical and volumetric similarity in contiguous, surface-accessible side chains in the peptide. Close analogs of one of the molecules discovered by 3D virtual screening, ZINC04085549 (FIG. 14C), were also selected for assays (FIG. 16-17) using the SwissSimilarity webserver (see website at www.swisssimilarity.ch; Zoete et al., J Chem Inf Model 56: 1399-1404 (2016)) and the website at zinc.docking.org/search/structure search with the ZINC database to find the most shape and chemically similar structures to ZINC04085549. In total, eleven molecules were selected for assay (FIGS. 16-17), representing different scaffolds.

The structure for ZINC04085549 is also shown below.

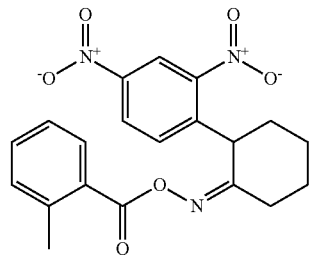

Cells and Reagents

Human SW620 colon cancer cells from the American Tissue Culture Collection were cultured as described by Thamilselvan & Basson, Gastroenterology 126: 8-18 (2004)). Chemical compounds from commercial suppliers (Tables 2 and 3) were at the highest available purity.

TABLE 2

Four compounds that mimic the LAHPP epitope (SEQ ID NO:25) in FAK

| ZINC name | Concentrations studied | Basal FAK-pTyr397 | Pressure stimulation of FAK-pTyr397 | Vendor/Supplier |
|---|---|---|---|---|
| ZINC31501681 | 1 pM-300 µM | Increased | No further increase | FCH Group (Made to order), Chernigov, Ukraine |
| ZINC58264388 | 1 nM-100 nM | Increased (10-100 nM) | No further increase (10-100 nM) | ENAMINE Limited, Kiev, Ukraine |
| ZINC40099027 | 10 pM-10 nM | Increased | No further increase | ENAMINE Limited, Kiev, Ukraine |
| ZINC25613745 | 1 nM | No change | Maintained | ENAMINE Limited, Kiev, Ukraine |

TABLE 3

Seven compounds that mimic the active two-site FAK mutant peptide, AAHPSEE

| ZINC name | Concentrations studied | Basal adhesion | Pressure stimulated adhesion | Vendor,Supplier |
|---|---|---|---|---|
| ZINC04085549 | 10-100 µM | Maintained | Blocked ≥50 µM | BIONET/Keyorganics Limited, Bedford, MA, USA |
| ZINC02457454 | 10-200 µM | Maintained | Not inhibited | Chem-Div, Inc. Vistas-M Laboratory, Ltd. (Premium), San Diego, USA |
| ZINC04085550 | 50 µM | Maintained | Not inhibited | BIONET/Keyorganics Limited, Bedford, MA, USA |
| ZINC12960430 | 50 µM | Maintained | Not inhibited | BIONET/Keyorganics Limited, Bedford, MA, USA |
| ZINC4085554 | 10-50 µM | Maintained | Blocked ≥50 µM | BIONET/Keyorganics Limited, Bedford, MA, USA |
| ZINC6241139 | 50 µM | Maintained | Not inhibited | BIONET/Keyorganics Limited, Bedford, MA, USA |

TABLE 3-continued

Seven compounds that mimic the active two-site FAK mutant peptide, AAHPSEE

| ZINC name | Concentrations studied | Basal adhesion | Pressure stimulated adhesion | Vendor,Supplier |
|---|---|---|---|---|
| ZINC5816335 | 10-50 μM | Maintained | Not inhibited | BIONET/Keyorganics Limited, Bedford, MA. USA |

Extracellular Pressure Treatment

Extracellular pressure was increased by 15 mmHg over ambient pressure using a temperature and pressure-controlled box as described by Basson et al. (J Cell Biochem, 78: 47-61 (2000)).

FAK-Y397 Western Blotting

Cells were maintained at ambient or increased pressure in bacteriologic plastic dishes pacificated with heat-inactivated bovine serum albumin to prevent adhesion and avoid adhesion-associated background FAK activation. Cells were lysed in lysis buffer, resolved by 10% SDS-PAGE, transferred to nitrocellulose and blotted with antibody to Tyr-397-phosphorylated FAK (rabbit monoclonal ab81298, Abcam, San Francisco, Calif., USA) and anti-rabbit 680 (LI-COR Inc. Lincoln, Nebr., USA), before quantitation using Kodak Scientific Imaging Systems 1D, V.3.5.4 (Zeng et al., Oncotarget, 8 98051-98067 (2017)). Total FAK (Anti-FAK, clone 4.47 Merck, Darmstadt, Germany with secondary anti-mouse 800, LI-COR Inc. Lincoln, Nebr., USA) served as a loading control. FAK and Tyr-397-phosphorylated FAK western blots yielded doublets similar to those previously observed by others (McConnell et al. Mol Cancer 10: 75 (2011); Aflaki et al. Cell Mol Life Sci, 68: 3933-3947 (2011)); Das et al. Cancer Res, 72: 6217-6226 (2012); Ammoun et al. Oncogene, 31: 1710-1722 (2012)). Both bands were quantitated together.

Adhesion Assay

Cells were seeded in an amount of 50,000 cells/well into 24 well plates precoated with collagen I (Sigma, St. Louis, Mo., USA) at 37° C. under ambient or 15 mmHg increased pressure as described by Basson et al. J Cell Biochem 78: 47-61 (2000)). After 30 minutes, non-adherent cells were washed away. Adherent cells were stained with MTS (Cell-Titer 96® AQ$_{ueous}$ One Solution Cell Proliferation Assay, Madison, Wis., USA) and plates were read at 490 nm.

Statistical Analysis

All assays were performed within linear ranges. Data were normalized against ambient pressure controls treated with DMSO as a vehicle control, represented as X±SE, and analyzed by t-test seeking 95% confidence.

Results

The eleven molecules described above and in FIGS. 14, 16 and 17 were tested in human SW620 colon cancer cells for their ability to prevent either stimulation of FAK phosphorylation or stimulation of adhesion to collagen.

FAK Phosphorylation Studies

Four structurally similar molecules to the FAK-derived sequence LAHPP (SEQ ID NO:25) (Table 2) were evaluated for their ability to prevent FAK activation by 15 mmHg increased extracellular pressure in human SW620 colon cancer cells. FAK-Tyr-397 phosphorylation was measured as an early step in FAK activation, as previously demonstrated in the pressure-activated adhesion pathway (Thamilselvan & Basson, Gastroenterology 126: 8-18 (2004)) and in FAK activation by other stimuli (Schlaepfer et al. Prog Biophys Mol Biol, 71: 435-478 (1999); Pasons, J Cell Sci, 116: 1409-1416 (2003)). Hence, compounds that inhibit FAK phosphorylation were of interest as FAK inhibitors. Three molecules, ZINC31501681, ZINC58264388, and ZINC40099027 increased basal FAK-Tyr-397 phosphorylation even at ambient pressure (Table 2 and FIG. 17). The structures of these compounds are shown below (and in FIG. 17).

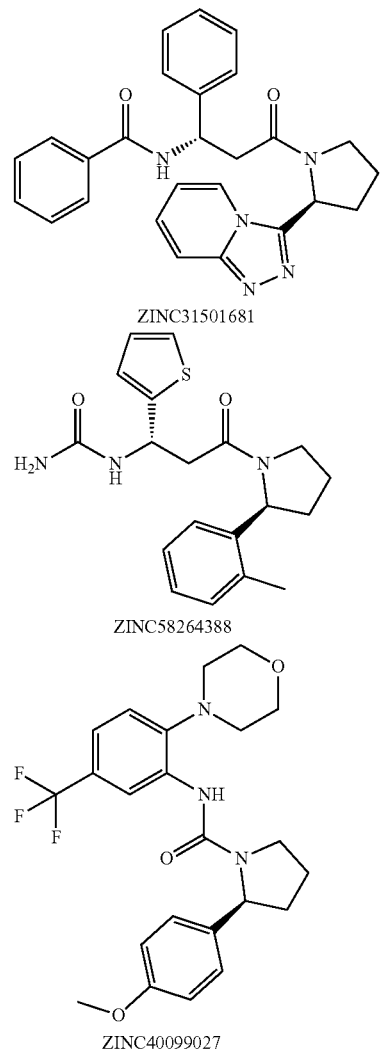

ZINC31501681

ZINC58264388

ZINC40099027

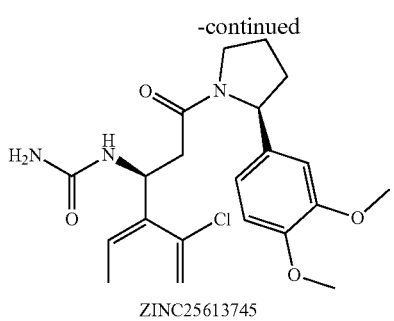

ZINC25613745

Figure 15A:
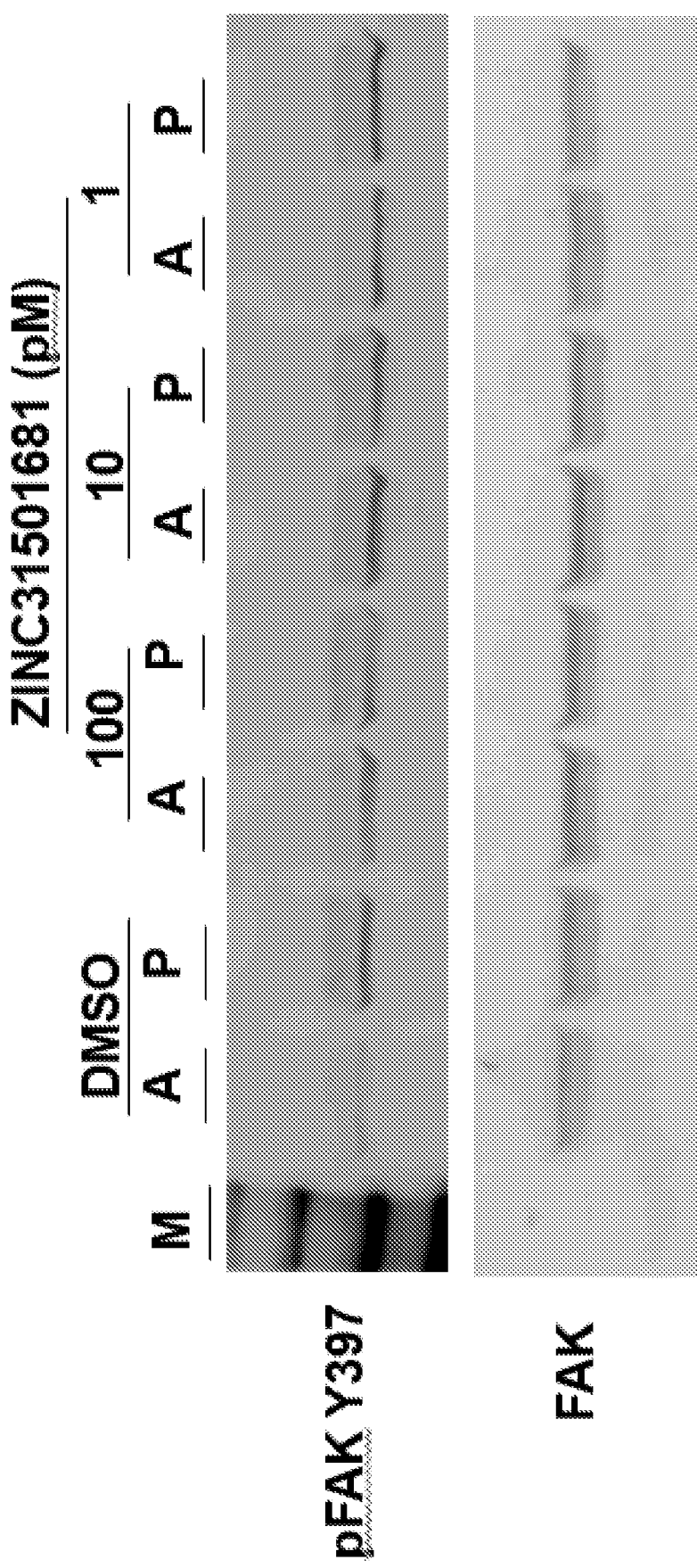
FIG. 15A-15B illustrate that ZINC31501681 enhances the phosphorylation of FAK-Tyr-397 in suspended human SW620 cells at ambient pressure.
Figure 15B:
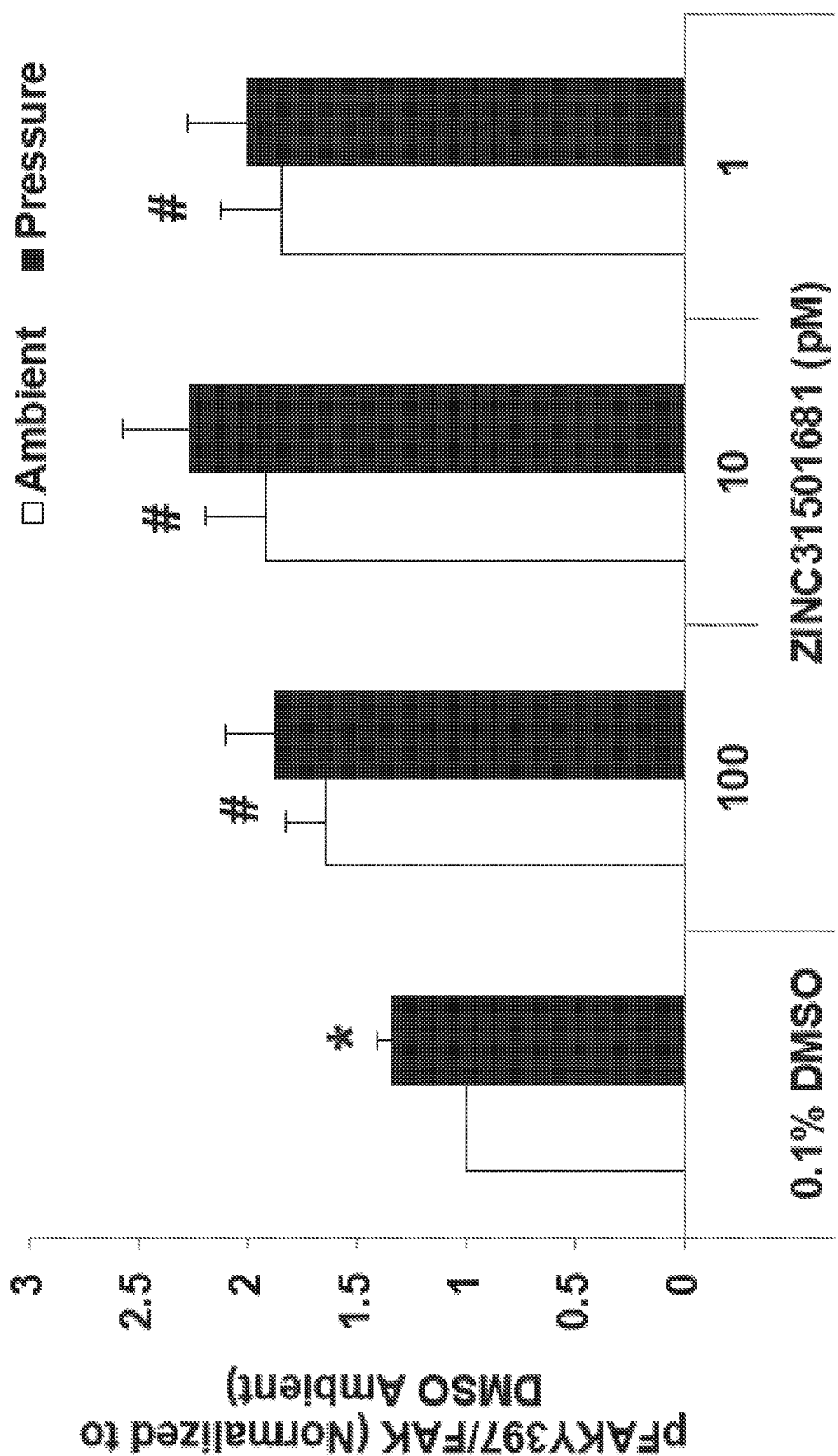
Figure 16A:
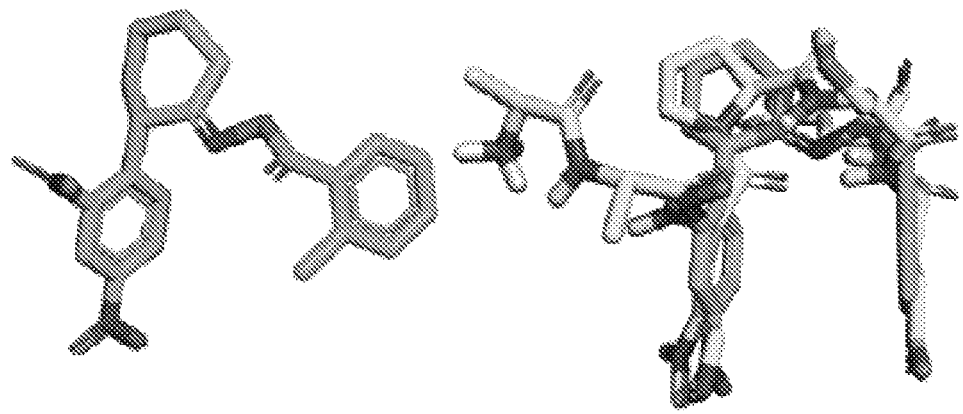
FIG. 16A-16G shows structures of the AAHPSEE (SEQ ID NO:24) small molecule mimics tested.
Figure 16A:
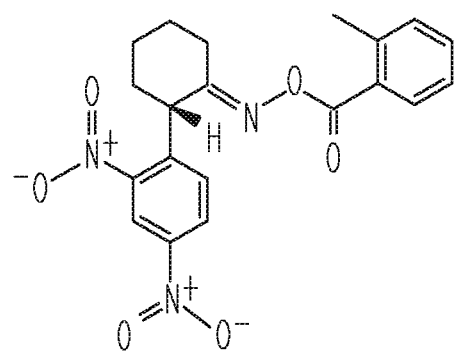
Figure 16B:
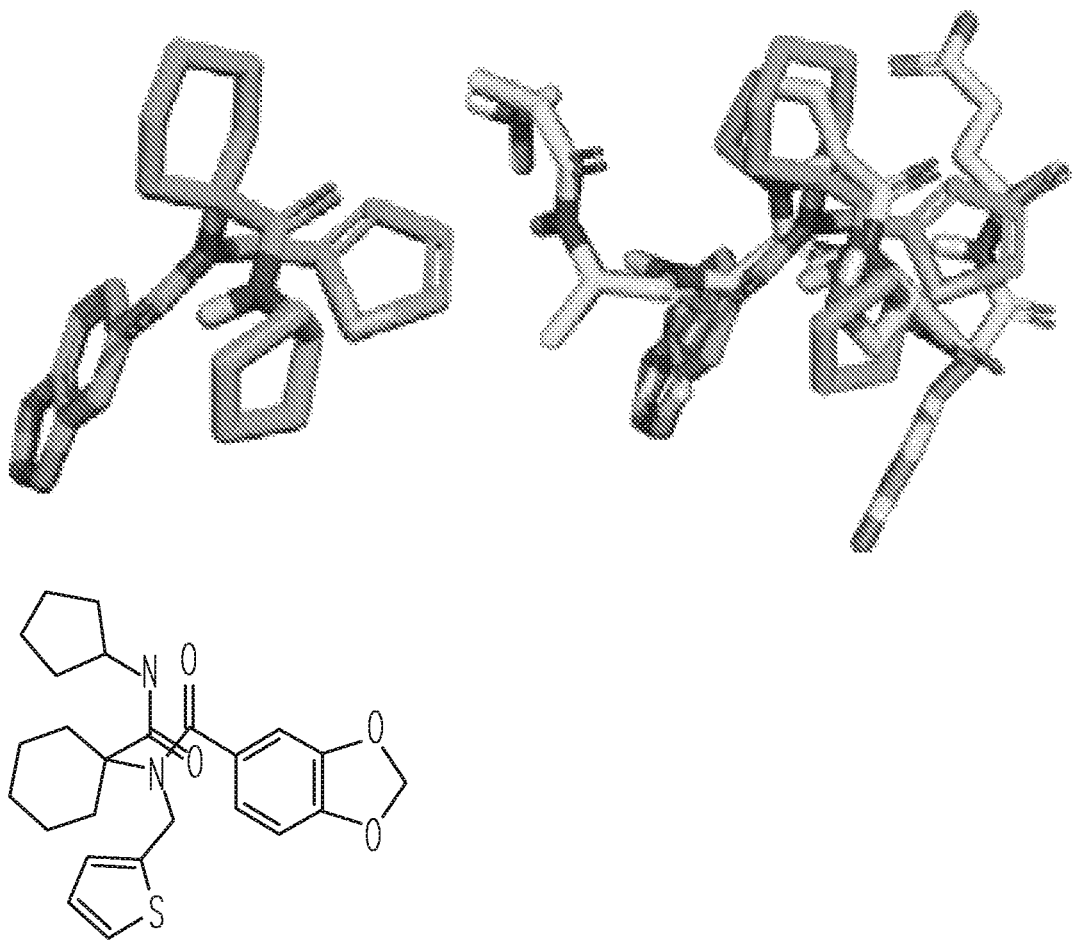
Figure 16C:
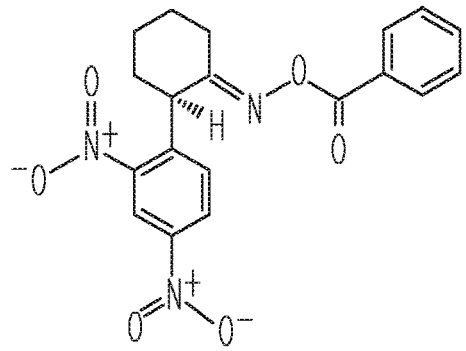
Figure 16D:
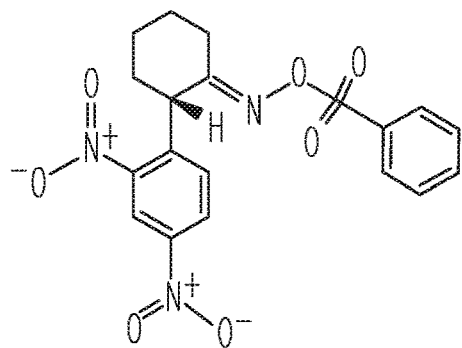
Figure 16E:
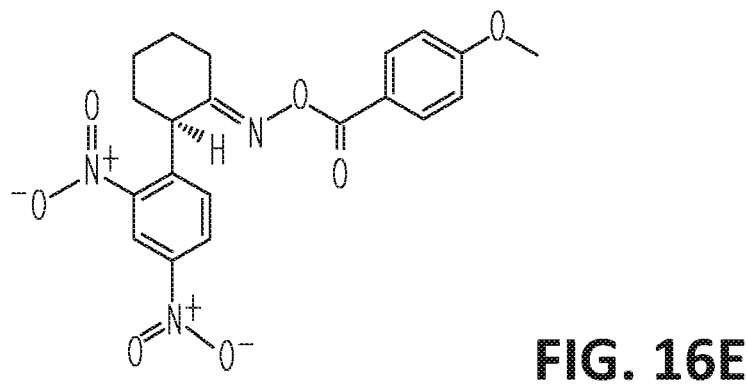
Figure 16F:
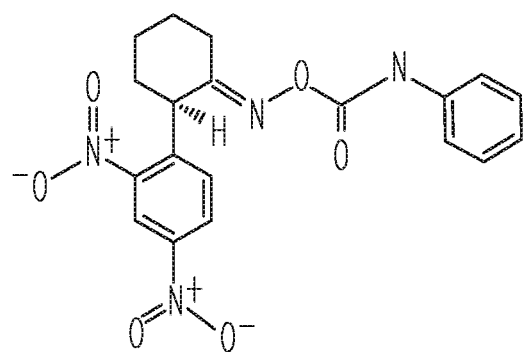
Figure 16G:
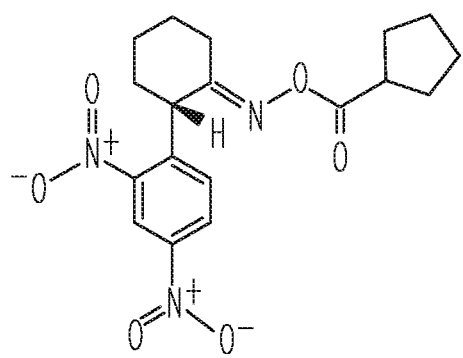
Figure 17A:
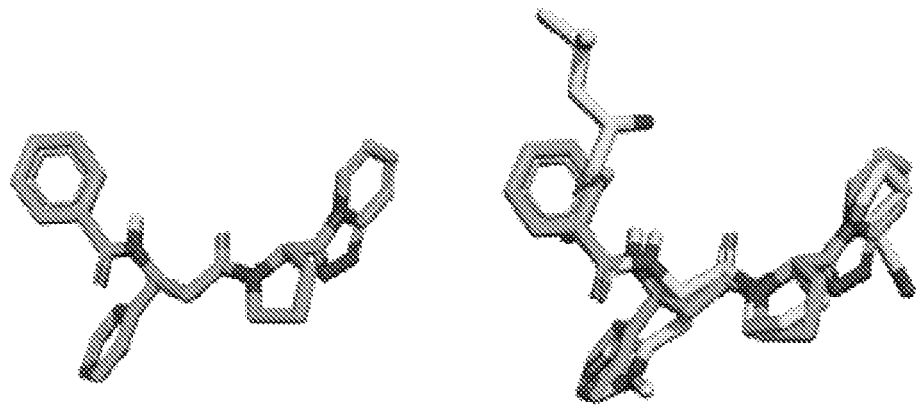
FIG. 17A-17D show structures of small molecule mimics of the LAHPP (SEQ ID NO:25) peptide that were assayed. The drug-like mimics overlaid by ROCS are shown with carbons in green in the original; LAHPP (SEQ ID NO:25) is overlaid with carbons in yellow in the original.
Figure 17B:
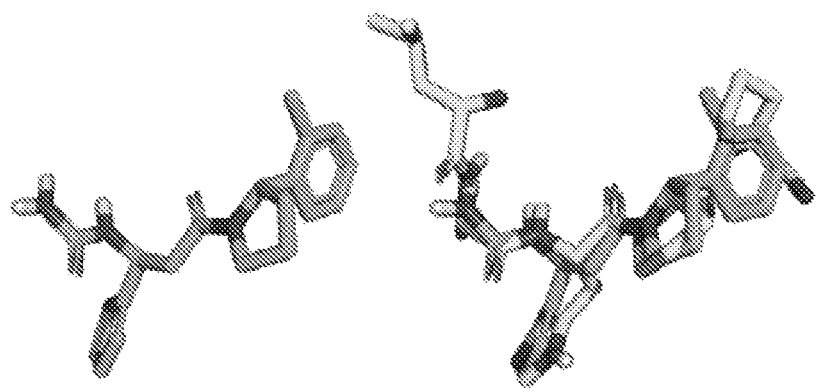
Figure 17C:
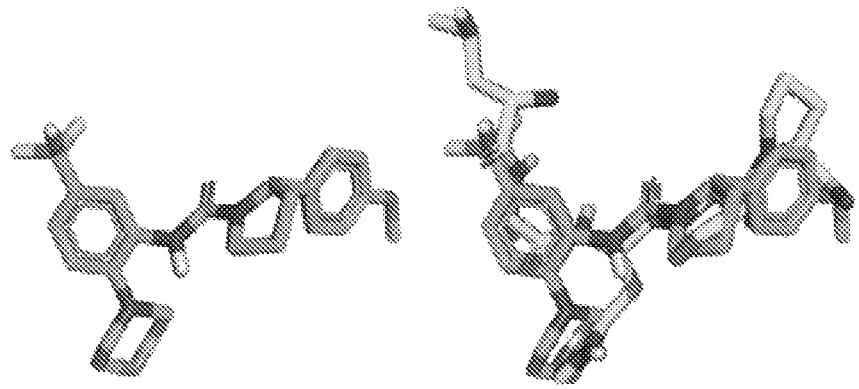
Figure 17D:

Each of ZINC31501681, ZINC58264388, and ZINC40099027 also prevented a further pressure-induced increase in FAK-Tyr-397 phosphorylation. In comparison, at 1 nM, ZINC25613745 affected neither basal nor pressure-stimulated FAK-Tyr-397 phosphorylation. FIG. 15A-15B show a typical study. The tendency of these compounds to increase basal FAK phosphorylation at ambient pressure made these LAHPP (SEQ ID NO:25) small molecule mimics unattractive for further study. Instead, the goal had been to block FAK activation by blocking FAK phosphorylation.

Adhesion Studies

Figure 18:
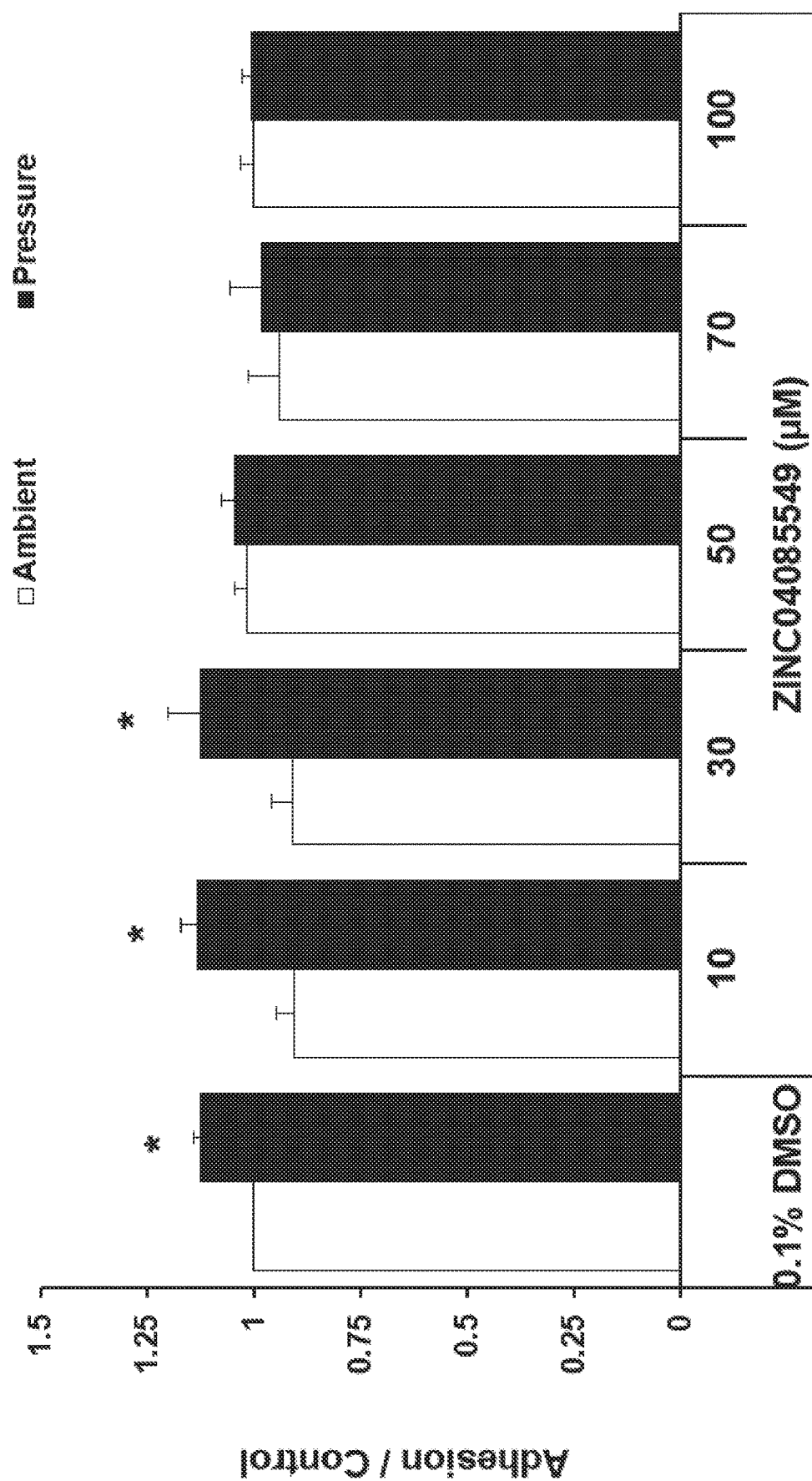
FIG. 18 graphically illustrates that the ZINC04085549 compound blocks stimulation of SW620 cell adhesion to collagen I by increased extracellular pressure. SW620 cells were treated with 0.1% DMSO (vehicle control) or ZINC04085549 at 10-100 µM and allowed to adhere to collagen I for 30 minutes at ambient or 15 mmHg increased pressure. (n=4, *p≤0.05).

Seven molecules were studied that structurally mimic AAHPSEE (SEQ ID NO:24), including five analogs of ZINC04085549 (FIG. 16A-16G). These molecules' effects on basal and pressure-stimulated human SW620 colon cancer cell adhesion to collagen I were assayed first. Most molecules had no effect at the concentrations studied (Table 3). However, two molecules, ZINC04085549 and ZINC4085554, prevented pressure-stimulated increases in SW620 adhesion without altering basal adhesiveness at ambient pressure (Table 3; FIG. 18).

Effects of ZINC04085549 on FAK-Tyr-397 Phosphorylation

Figure 19A:
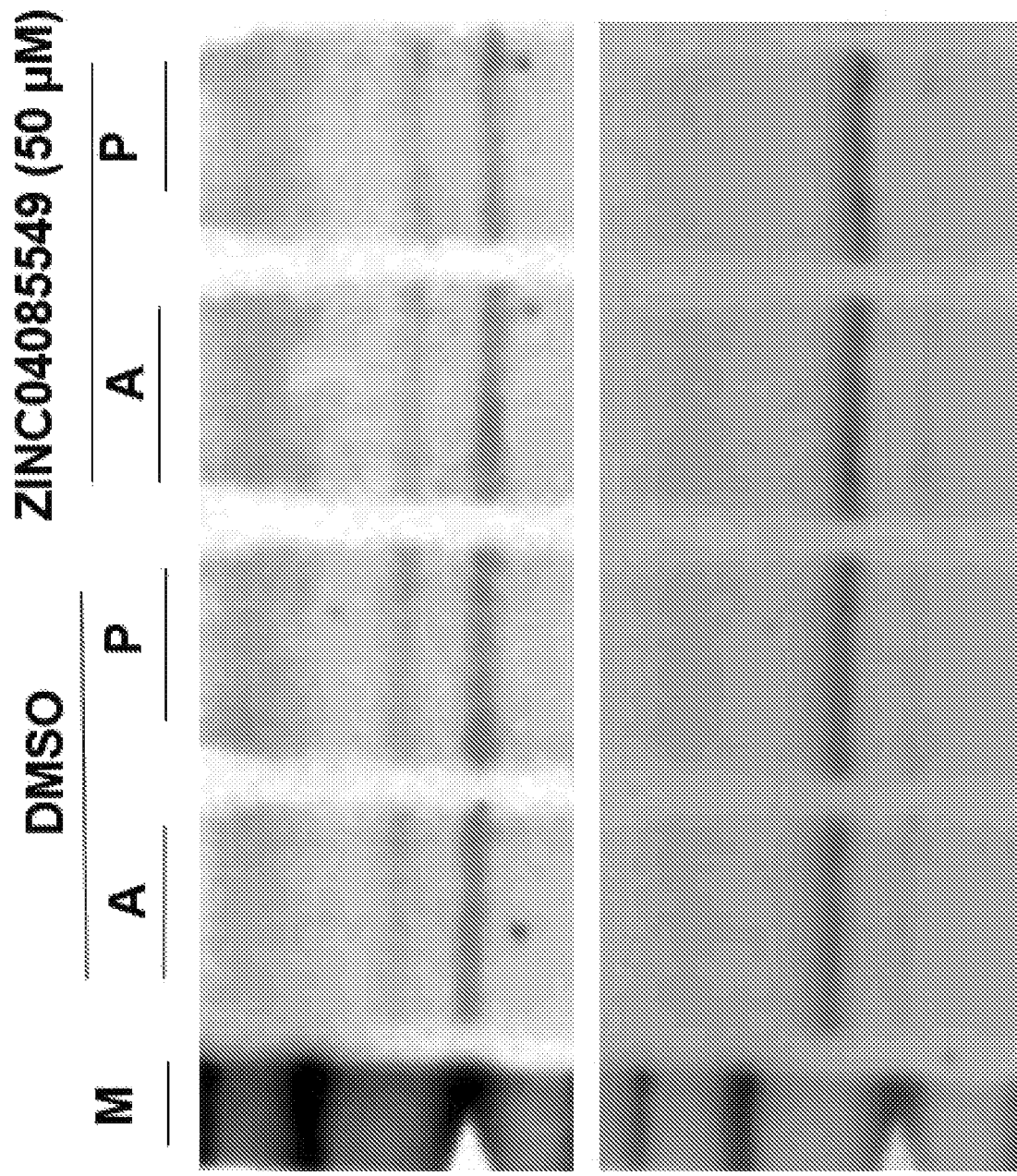
FIG. 19A-19B illustrate that ZINC04085549 blocks pressure-stimulated phosphorylation of FAK-Tyr-397. Suspended SW620 cells treated with 0.1% DMSO (vehicle control) or 50 µM ZINC04085549 were incubated at ambient (A) or 15 mmHg increased pressure (P).
Figure 19B:
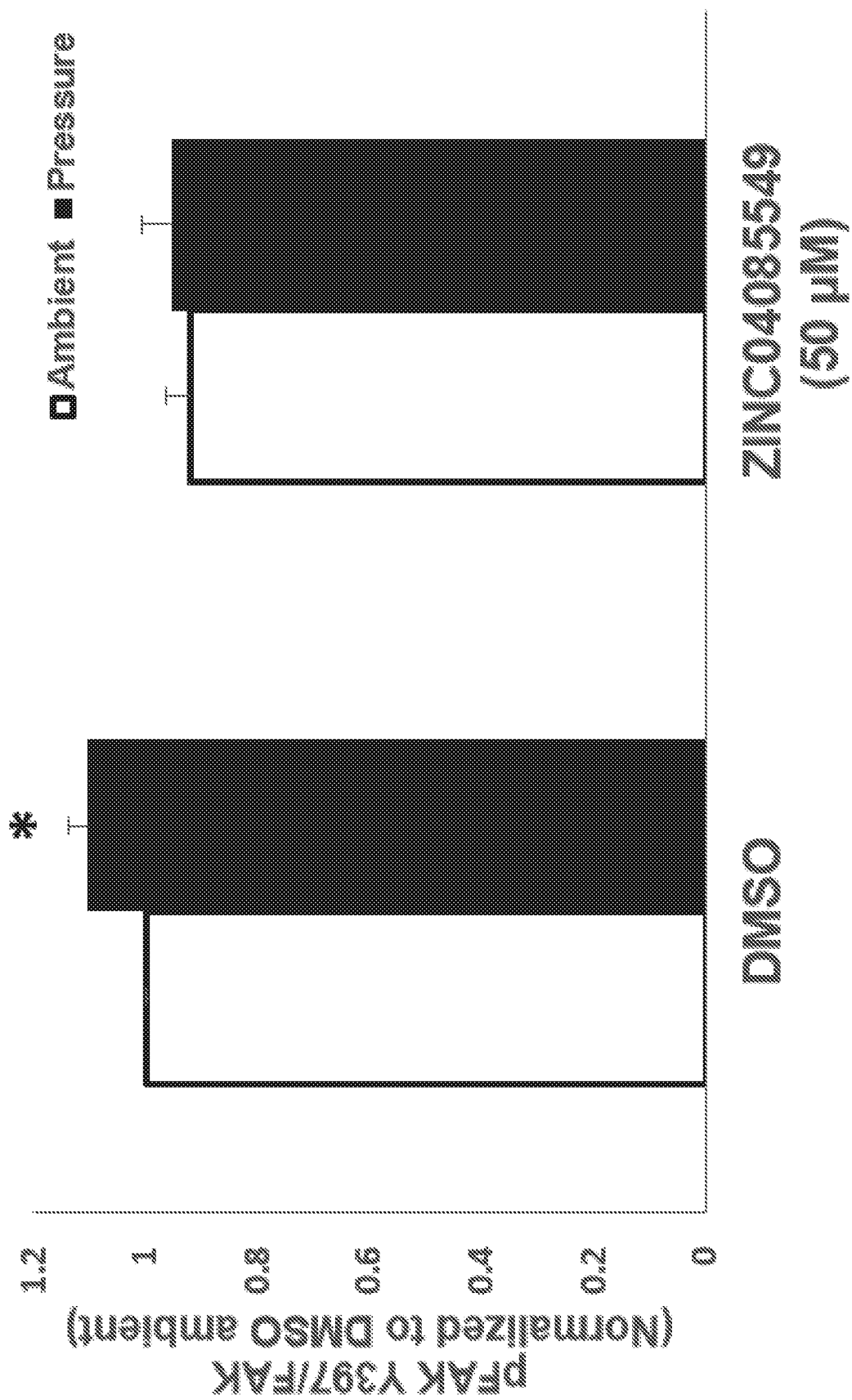

As one of the promising molecules preventing pressure-stimulated adhesion, ZINC04085549 was further evaluated for the ability to prevent pressure-stimulated FAK-Tyr-397 phosphorylation. At 50 μM, ZINC04085549 prevented pressure-stimulated FAK-Tyr-397 phosphorylation without affecting basal ambient pressure FAK-Tyr-397 phosphorylation (FIG. 19).

REFERENCES

1. Fidler U. Cancer biology is the foundation for therapy. Cancer Biol Ther. 2005; 4(9):1036-9.
2. Sugarbaker P H. Successful management of microscopic residual disease in large bowel cancer. Cancer Chemother Pharmacol. 1999; 43 Suppl:S15-25.
3. Allardyce R, Morreau P, Bagshaw P. Tumor cell distribution following laparoscopic colectomy in a porcine model. Dis Colon Rectum. 1996; 39(10 Suppl):547-52.
4. Weitz J, Koch M, Kienle P, Schrodel A, Willeke F, Benner A, et al. Detection of hematogenic tumor cell dissemination in patients undergoing resection of liver metastases of colorectal cancer. Ann Surg. 2000; 232(1):66-72.
5. Choy A, McCulloch P. Induction of tumour cell shedding into effluent venous blood breast cancer surgery. Br J Cancer. 1996; 73(1):79-82.
6. Uchikura K, Takao S, Nakajo A, Miyazono F, Nakashima S, Tokuda K, et al. Intraoperative molecular detection of circulating tumor cells by reverse transcription-polymerase chain reaction in patients with biliary-pancreatic cancer is associated with hematogenous metastasis. Ann Surg Oncol. 2002; 9(4):364-70.
7. Yamaguchi K, Takagi Y, Aoki S, Futamura M, Saji S. Significant detection of circulating cancer cells in the blood by reverse transcriptase-polymerase chain reaction during colorectal cancer resection. Ann Surg. 2000; 232 (1):58-65.
8. Hayashi N, Egami H, Kai M, Kurusu Y, Takano S, Ogawa M. No-touch isolation technique reduces intraoperative shedding of tumor cells into the portal vein during resection of colorectal cancer. Surgery. 1999; 125(4):369-74.
9. Clinical Outcomes of Surgical Therapy Study G, Nelson H, Sargent D J, Wieand H S, Fleshman J, Anvari M, et al. A comparison of laparoscopically assisted and open colectomy for colon cancer. N Engl J Med. 2004; 350 (20):2050-9.
10. Turnbull R B, Jr., Kyle K, Watson F R, Spratt J. Cancer of the colon: the influence of the no-touch isolation technic on survival rates. Ann Surg. 1967; 166(3):420-7.
11. Basson M D, Yu C F, Herden-Kirchoff O, Ellermeier M, Sanders M A, Merrell R C, et al. Effects of increased ambient pressure on colon cancer cell adhesion. J Cell Biochem. 2000; 78(1):47-61.
12. Shiratsuchi H, Basson M D. Extracellular pressure stimulates macrophage phagocytosis by inhibiting a pathway involving FAK and ERK. Am J Physiol Cell Physiol. 2004; 286(6):$C_{1358}$-66.
13. Thubrikar M J, Robicsek F. Pressure-induced arterial wall stress and atherosclerosis. Ann Thorac Surg. 1995; 59(6):1594-603.
14. Basson M D, Zeng B, Downey C, Sirivelu M P, Tepe J J. Increased extracellular pressure stimulates tumor proliferation by a mechanosensitive calcium channel and PKC-beta. Mol Oncol. 2015; 9(2):513-26.
15. Huynh K C, Gyenes M, Nguyen T H, Vo T V, Stoldt V R. Impact of shear stress on Src and focal adhesion kinase phosphorylation in fibrinogen-adherent platelets. Blood Coagul Fibrinolysis. 2016.
16. Thamilselvan V, Patel A, van der Voort van Zyp J, Basson M D. Colon cancer cell adhesion in response to Src kinase activation and actin-cytoskeleton by non-laminar shear stress. J Cell Biochem. 2004; 92(2):361-71.
17. Basson M D. An intracellular signal pathway that regulates cancer cell adhesion in response to extracellular forces. Cancer Res. 2008; 68(1):2-4.
18. Less J R, Posner M C, Boucher Y, Borochovitz D, Wolmark N, Jain R K. Interstitial hypertension in human breast and colorectal tumors. Cancer Res. 1992; 52(22): 6371-4.
19. Gutmann R, Leunig M, Feyh J, Goetz A E, Messmer K, Kastenbauer E, et al. Interstitial hypertension in head and neck tumors in patients: correlation with tumor size. Cancer Res. 1992; 52(7):1993-5.
20. Conway W C, Van der Voort van Zyp J, Thamilselvan V, Walsh M F, Crowe D L, Basson M D. Paxillin modulates squamous cancer cell adhesion and is important in pressure-augmented adhesion. J Cell Biochem. 2006; 98(6): 1507-16.
21. Perry B C, Wang S, Basson M D. Extracellular pressure stimulates adhesion of sarcoma cells via activation of focal adhesion kinase and Akt. Am J Surg. 2010; 200(5): 610-4.
22. Thamilselvan V, Craig D H, Basson M D. FAK association with multiple signal proteins mediates pressure-induced colon cancer cell adhesion via a Src-dependent PI3K/Akt pathway. FASEB J. 2007; 21(8):1730-41.

23. Thamilselvan V, Basson M D. Pressure activates colon cancer cell adhesion by inside-out focal adhesion complex and actin cytoskeletal signaling. Gastroenterology. 2004; 126(1):8-18.
24. van Zyp J, Conway W C, Craig D H, van Zyp N, Thamilselvan V, Basson M D. Extracellular pressure stimulates tumor cell adhesion in vitro by paxillin activation. Cancer Biol Ther. 2006; 5(9):1169-78.
25. van der Voort van Zyp J, Conway W C, Thamilselvan V, Polin L, Basson M D. Divalent cations influence colon cancer cell adhesion in a murine transplantable tumor model. Am J Surg. 2005; 190(5):701-7.
26. Craig D H, Owen C R, Conway W C, Walsh M F, Downey C, Basson M D. Colchicine inhibits pressure-induced tumor cell implantation within surgical wounds and enhances tumor-free survival in mice. J Clin Invest. 2008; 118(9):3170-80.
27. Craig D H, Downey C, Basson M D. SiRNA-mediated reduction of alpha-actinin-1 inhibits pressure-induced murine tumor cell wound implantation and enhances tumor-free survival. Neoplasia. 2008; 10(3):217-22.
28. Wang S, Basson M D. Akt directly regulates focal adhesion kinase through association and serine phosphorylation: implication for pressure-induced colon cancer metastasis. Am J Physiol Cell Physiol. 2011; 300(3): C657-70.
29. Craig D H, Gayer C P, Schaubert K L, Wei Y, Li J, Laouar Y, et al. Increased extracellular pressure enhances cancer cell integrin-binding affinity through phosphorylation of beta1-integrin at threonine 788/789. Am J Physiol Cell Physiol. 2009; 296(1): C193-204.
30. Basson M D, Zeng B, Wang S. Akt1 binds focal adhesion kinase via the Akt1 kinase domain independently of the pleckstrin homology domain. J Physiol Pharmacol. 2015; 66(5):701-9.
31. Ceccarelli D F, Song H K, Poy F, Schaller M D, Eck M J. Crystal structure of the FERM domain of focal adhesion kinase. J Biol Chem. 2006; 281(1):252-9.
32. Sieg D J, Hauck C R, Schlaepfer D D. Required role of focal adhesion kinase (FAK) for integrin-stimulated cell migration. J Cell Sci. 1999; 112 (Pt 16):2677-91.
33. Golubovskaya V, Curtin L, Groman A, Sexton S, Cance W G. In vivo toxicity, metabolism and pharmacokinetic properties of FAK inhibitor 14 or Y15 (1,2,4,5-benzenetetramine tetrahydrochloride). Arch Toxicol. 2015; 89(7): 1095-101.
34. Galvez-Peralta M, Flatten K S, Loegering D A, Peterson K L, Schneider P A, Erlichman C, et al. Context-dependent antagonism between Akt inhibitors and topoisomerase poisons. Mol Pharmacol. 2014; 85(5):723-34.
35. Parsons J T. Focal adhesion kinase: the first ten years. J Cell Sci. 2003; 116(Pt 8):1409-16.
36. Lietha D, Cai X, Ceccarelli D F, Li Y, Schaller M D, Eck M J. Structural basis for the autoinhibition of focal adhesion kinase. Cell. 2007; 129(6):1177-87.
37. Sporn M B. The war on cancer. Lancet. 1996; 347(9012): 1377-81.
38. Walsh M F, Woo R K, Gomez R, Basson M D. Extracellular pressure stimulates colon cancer cell proliferation via a mechanism requiring PKC and tyrosine kinase signals. Cell Prolif. 2004; 37(6):427-41.
39. Downey C, Craig D H, Basson M D. Isoform-specific modulation of pressure-stimulated cancer cell proliferation and adhesion by alpha-actinin. Am J Surg. 2011; 202(5):520-3.
40. Downey C, Alwan K, Thamilselvan V, Zhang L, Jiang Y, Rishi A K, et al. Pressure stimulates breast cancer cell adhesion independently of cell cycle and apoptosis regulatory protein (CARP)-1 regulation of focal adhesion kinase. Am J Surg. 2006; 192(5):631-5.
41. Umpleby H C, Fermor B, Symes M O, Williamson R C. Viability of exfoliated colorectal carcinoma cells. Br J Surg 1984; 71:659-63.
42. Curti B D, Urba W J, Alvord W G, Janik J E, Smith J W, 2nd, Madara K, et al. Interstitial pressure of subcutaneous nodules in melanoma and lymphoma patients: changes during treatment. Cancer Res 1993; 53:2204-7.
43. Dregelid E, Svendsen E. Endothelial cell injury in human saphenous veins after manipulation and tweezer grasping. J Cardiovasc Surg (Torino) 1988; 29:464-9.
44. Zhang J, Owen C R, Sanders M A, Turner J R, Basson M D. The motogenic effects of cyclic mechanical strain on intestinal epithelial monolayer wound closure are matrix dependent. Gastroenterology 2006; 131:1179-89.
45. Sadoshima J, Izumo S. The cellular and molecular response of cardiac myocytes to mechanical stress. Annu Rev Physiol 1997; 59:551-71.
46. Thomas J W, Cooley M A, Broome J M, Salgia R, Griffin J D, Lombardo C R, et al. The role of focal adhesion kinase binding in the regulation of tyrosine phosphorylation of paxillin. J Biol Chem 1999; 274:36684-92.
47. Zeng B W, S. Yang, R. Sunzy, Z. Xi, N. Kuhn, L. Basson, M D. Inhibition of Pressure-Stimulated FAK and Akt1 Interaction via a 33 Amino Acid FAK-derived Peptide. Gastroenterology 148 (4):5954-5955, 2015.
48. Craig L, Sanschagrin P C, Rozek A, Lackie S, Kuhn L A, Scott J K. The role of structure in antibody cross-reactivity between peptides and folded proteins. J Mol Biol 1998; 281:183-201.
49. Prevelige P, Fasman G D. Chou-Fasman Prediction of the Secondary Structure of Proteins: The Chou-Fasman-Prevelige Algorithm. In: Fasman G D, editor. Prediction of the Structure and the Principles of Protein Conformation. New York: Springer; 1989. p 391-416.
50. Ko H R, Kwon I S, Hwang I, Jin E J, Shin J H, Brennan-Minnella A M, et al. Akt1-Inhibitor of DNA binding2 is essential for growth cone formation and axon growth and promotes central nervous system axon regeneration. Elife 2016; 5.
51. Wu R, Liu X M, Sun J G, Chen H, Ma J, Dong M, et al. DJ-1 maintains energy and glucose homeostasis by regulating the function of brown adipose tissue. Cell Discov 2017; 3:16054.
52. Datta S R, Dudek H, Tao X, Masters S, Fu H, Gotoh Y, et al. Akt phosphorylation of BAD couples survival signals to the cell-intrinsic death machinery. Cell 1997; 91:231-41.
53. Li W, Zhang J, Flechner L, Hyun T, Yam A, Franke T F, et al. Protein kinase C-alpha overexpression stimulates Akt activity and suppresses apoptosis induced by interleukin 3 withdrawal. Oncogene 1999; 18:6564-72.
54. Manning B D, Cantley L C. AKT/PKB signaling: navigating downstream. Cell 2007; 129:1261-74.
55. Leng C, Zhang Z G, Chen W X, Luo H P, Song J, Dong W, et al. An integrin beta4-EGFR unit promotes hepatocellular carcinoma lung metastases by enhancing anchorage independence through activation of FAK-AKT pathway. Cancer Lett 2016; 376:188-96.
56. Riggio M, Perrone M C, Polo M L, Rodriguez M J, May M, Abba M, et al. AKT1 and AKT2 isoforms play distinct roles during breast cancer progression through the regulation of specific downstream proteins. Sci Rep 2017; 7:44244.

57. Cohen L A, Guan J L. Residues within the first subdomain of the FERM-like domain in focal adhesion kinase are important in its regulation. J Biol Chem 2005; 280: 8197-207.
58. Wu J S, Brasfield E B, Guo L W, Ruiz M, Connett J M, Philpott G W, et al. Implantation of colon cancer at trocar sites is increased by low pressure pneumoperitoneum. Surgery 1997; 122:1-7.
59. Shen M Y, Huang I P, Chen W S, Chang J T, Lin J K. Influence of pneumoperitoneum on tumor growth and pattern of intra-abdominal tumor spreading: in vivo study of a murine model. Hepatogastroenterology 2008; 55:947-51.
60. Lee B Y, Hochgrafe F, Lin H M, Castillo L, Wu J, Raftery M J, et al. Phosphoproteomic profiling identifies focal adhesion kinase as a mediator of docetaxel resistance in castrate-resistant prostate cancer. Mol Cancer Ther 2014; 13:190-201.
61. Srinivas V, Datta S A, Ramakrishna T, Rao C M. Studies on the alpha-crystallin target protein binding sites: sequential binding with two target proteins. Mol Vis 2001; 7:114-9.
62. Goreczny G J, Ouderkirk-Pecone J L, Olson E C, Krendel M, Turner C E. Hic-5 remodeling of the stromal matrix promotes breast tumor progression. Oncogene 2017; 36:2693-703.
63. Basson M D, Zeng B, Wang S. The c-terminal region of the focal adhesion kinase f1 domain binds Akt1 and inhibits pressure-induced cell adhesion. J Physiol Pharmacol. 68(3):375-383, 2017.
64. Zeng B, Devadoss D, Wang S, Vomhof-DeKrey E E, Kuhn L A, Basson M D. Inhibition of pressure-activated cancer cell adhesion by FAK-derived peptides. Oncotarget. 8(58):98051-98067, 2017.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1) A method comprising administering one or more inhibitors of FAK/Akt1 interactions to a mammal.
2) The method of statement 1, wherein the inhibitor is a peptide comprising a 15-150 amino acid sequence with at least 90% sequence identity to any portion of SEQ ID NO:1, 2, 3, 4, 6, 7, 10, 11, 12-20, 21, or 22, or a peptide each comprising a 25-150 amino acid sequence with at least 90% sequence identity to any portion of SEQ ID NO:1, 2, 3, 4, 6, 7, 10, 11, 12-20, 21, or 22.
3) The method of statement 1 or 2, consisting essentially of a 15-150 amino acid sequence from a portion of any of SEQ ID NO: 1, 2, 3, 4, 6, 7, 10, 11, 12-20, 21, or 22.
4) The method of statement 1, 2, or 3, wherein the inhibitor is a compound of formula I:

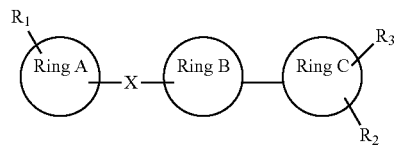

wherein:
Ring A and Ring C independently are each an aryl ring;
Ring B is a cycloalkyl ring;
$R_1$ is a hydrogen, lower alkyl or lower alkoxy;
X is a $C_1$ to $C_4$ alkyl linker comprising a carbonyl, a carboxylate, an amide, a carboxylate(amino), or an aminocarboxylate group or a $=N-O-SO_2-$ linker; and
$R_2$ and $R_3$ are independently each a carboxylate, an amide, or a nitro group.

5) The method of statement 1-3 or 4, wherein each aryl ring is a cyclic aromatic hydrocarbon that does not contain heteroatoms.
6) The method of statement 1-4 or 5, wherein each aryl ring has about five to about fourteen ring atoms and at least one aromatic ring.
7) The method of statement 1-5 or 6, wherein each aryl ring is a phenyl ring, a bicyclic ring (e.g., biphenyl), or tricyclic ring.
8) The method of statement 1-6 or 7, wherein each aryl ring is a phenyl, biphenyl, naphthalene, or anthracene group.
9) The method of statement 1-7 or 8, wherein the Ring A and Ring C groups are phenyl or naphthyl groups.
10) The method of statement 1-8 or 9, wherein the alkyl groups each have from 1 to about 20 carbon atoms, or from 1 to 12 carbons, or from 1 to 8 carbons, or from 1 to 6 carbon atoms.
11) The method of statement 1-9 or 10, wherein the alkyl groups are each lower alkyl groups with about 1 to 4 carbon atoms, or about 1 to about 3 carbon atoms.
12) The method of statement 1-10 or 11, wherein the Ring B group is a $C_1$ to $C_8$ cycloalkyl, or a $C_1$ to $C_6$ cycloalkyl.
13) The method of statement 1-11 or 12, wherein, the X group is a three to four atom linker, where atoms can include one or more carbon, oxygen, and nitrogen atoms, and where the carbon and/or nitrogen atoms can be substituted with an alkyl or an oxy group.
14) The method of statement 1-12 or 13, wherein, the X group is a three atom linker, with one carbon, one oxygen, and one nitrogen atom.
15) The method of statement 1-13 or 14, wherein, the X group comprises a carbonyl.
16) The method of statement 1-14 or 15, wherein X is a $C_1$ to $C_4$ alkyl linker comprising a carbonyl, a carboxylate, an amide, a carboxylate(amino), or an aminocarboxylate group.
17) The method of statement 1-15 or 16, wherein, the $R_2$ and $R_3$ groups are independently a carboxylate, or a nitro group.
18) The method of statement 1-16 or 17, wherein, the $R_2$ and $R_3$ groups are both nitro groups.
19) The method of statement 1-17 or 18, wherein, the inhibitor is the compound shown below:

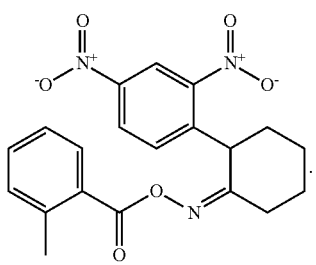

20) The method of statement 1-18 or 19, wherein the mammal is a human, a domesticated mammal, a zoo animal, or a laboratory animal.

21) The method of statement 1-19 or 20, which inhibits cancer cell adhesion and/or cancer cell metastasis in the mammal.

22) The method of statement 1-20 or 21, wherein the inhibitor is administered in an amount sufficient to inhibit cancer cell adhesion and/or cancer cell metastasis in the mammal.

23) The method of statement 1-21 or 22, wherein the inhibitor is administered in an amount sufficient to inhibit one or more symptom of cancer in the mammal.

24) The method of statement 23, wherein the at least one symptom of cancer is selected from the group consisting of cachexia, cancer cell adhesion, pain, fatigue, cancer cell growth, and metastatic spread.

25) The method of statement 1-23 or 24, wherein at least 20%, or at least 30%, or at least 40% of cancer cell adhesion is inhibited in the mammal.

26) The method of statement 1-24 or 25, wherein 20%-100% of cancer cell adhesion is inhibited.

27) The method of statement 1-25 or 26, wherein the cancer is selected from the group consisting of intestinal cancer, leukemia, sarcoma, osteosarcoma, lymphomas, melanoma, glioma, pheochromocytoma, hepatoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or liver cancer, and cancer at an unknown primary site.

28) The method of statement 1-26 or 27, wherein the cancer is colorectal cancer.

29) An isolated peptide comprising a 25-150 amino acid sequence with at least 90% sequence identity to any portion of SEQ ID NO:1, 2, 3, 4, 6, 7, 10, 11, 12-20, 21, or 22, or a peptide each comprising a 25-150 amino acid sequence with at least 90% sequence identity to any portion of SEQ ID NO:1, 2, 3, 4, 6, 7, 10, 11, 12-20, 21, or 22.

30) The isolated peptide of statement 29 that comprises SEQ ID NO:1.

31) The isolated peptide of statement 29 or 30, consisting essentially of a 25-150 amino acid sequence from a portion of any of SEQ ID NOs:1, 2, 3, 4, 6, 7, 10, 11, 12-20, 21, or 22.

32) The isolated peptide of statement 29, 30 or 31, consisting essentially of an amino acid sequence selected from SEQ ID NO:1, 2, 3, 4, 7, 21, 22, or a combination thereof.

33) The isolated peptide of statement 29-31 or 32, with a sequence comprising at least one amino acid substitution, insertion, deletion or replacement of SEQ ID NOs:1, 2, 3, 4, 6, 7, 10, 11, 12-20, 21, or 22.

34) An isolated nucleic acid encoding the isolated peptide of statement 29-32 or 33.

35) An expression cassette comprising a promoter operably linked to a nucleic acid segment encoding the isolated peptide of any of statements 29-33 or 34.

36) An expression vector comprising a promoter operably linked to a nucleic acid segment encoding the isolated peptide of statement 29-34 or 35.

37) A compound of formula I:

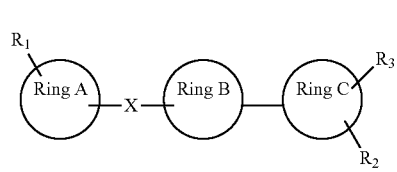

wherein:
Ring A and Ring C independently are each an aryl ring;
Ring B is a cycloalkyl ring;
$R_1$ is a lower alkyl or lower alkoxy;
X is a $C_1$ to $C_4$ alkyl linker comprising a carbonyl, a carboxylate, an amide, a carboxylate(amino), or an aminocarboxylate group or a =N—O—SO$_2$— linker; and
$R_2$ and $R_3$ are independently each a carboxylate, an amide, or a nitro group.

38) The compound of statement 37, wherein each aryl ring is a cyclic aromatic hydrocarbon that does not contain heteroatoms.

39) The compound of statement 37 or 38, wherein each aryl ring has about five to about fourteen ring atoms and at least one aromatic ring.

40) The compound of statement 37, 38 or 39, wherein each aryl ring is a phenyl ring, a bicyclic ring (e.g., biphenyl), or tricyclic ring.

41) The compound of statement 37-39 or 40, wherein each aryl ring is a phenyl, biphenyl, naphthalene, or anthracene group.

42) The compound of statement 37-40 or 41, wherein the Ring A and Ring C groups are phenyl or naphthyl groups.

43) The compound of statement 37-41 or 42, wherein the alkyl groups each have from 1 to about 20 carbon atoms, or from 1 to 12 carbons, or from 1 to 8 carbons, or from 1 to 6 carbon atoms.

44) The compound of statement 37-42 or 43, wherein the alkyl groups are each lower alkyl groups with about 1 to 4 carbon atoms, or about 1 to about 3 carbon atoms.

45) The compound of statement 37-43 or 44, wherein the Ring B group is a $C_1$ to $C_8$ cycloalkyl, or a $C_1$ to $C_6$ cycloalkyl.

46) The compound of statement 37-44 or 45, wherein, the X group is a three to four atom linker, where atoms can include one or more carbon, oxygen, and nitrogen atoms, and where the carbon and/or nitrogen atoms can be substituted with an alkyl or an oxy group.

47) The compound of statement 37-45 or 46, wherein, the X group is a three-atom linker, with one carbon, one oxygen, and one nitrogen atom.

48) The compound of statement 37-46 or 47, wherein, the X group comprises a carbonyl.
49) The compound of statement 37-47 or 48, wherein X is a $C_1$ to $C_4$ alkyl linker comprising a carbonyl, a carboxylate, an amide, a carboxylate(amino), or an aminocarboxylate group
50) The compound of statement 37-48 or 49, wherein, the $R_2$ and $R_3$ groups are independently a carboxylate, or a nitro group.
51) The compound of statement 37-49 or 50, wherein, the $R_2$ and $R_3$ groups are both nitro groups.
52) The compound of statement 37-50 or 51, wherein, the inhibitor is the compound shown below:

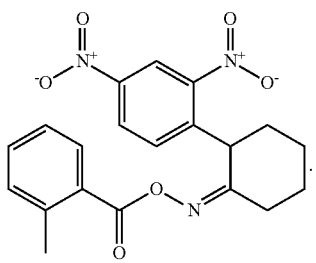

53) A composition comprising the isolated peptide of statement 29-32 or 33; the isolated nucleic acid of statement 34; the expression cassette of statement 35; the expression vector of statement 36; or the compound of statement 37-51 or 52, or a combination thereof
54) The composition of statement 31, further comprising a carrier.
55) The composition of statement 53 or 54, further comprising a pharmaceutically acceptable carrier.
56) The composition of statement 53, 54, or 55, formulated for parenteral administration.
57) The composition of statement 53-53 or 54, formulated for local administration.
58) The composition of statement 51-55 or 56, formulated for intravenous administration.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "an inhibitor" or "a molecule" or "a cell" includes a plurality of such inhibitors, molecules or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A method of reducing metastasis of cancer cells in a mammal comprising administering one or more inhibitors of FAK/Akt1 to a mammal in an amount sufficient to reduce metastasis of cancer cells in the mammal, wherein the inhibitor is:

one or more compounds with the following structure:

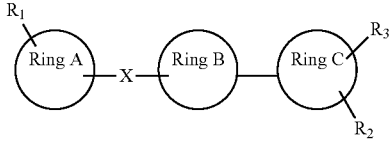

I wherein:

Ring A and Ring C independently are each an aryl ring;

Ring B is a cycloalkyl ring;

$R_1$ is a lower alkyl or lower alkoxy;

X is a $C_1$ to $C_4$ alkyl linker comprising a carbonyl, a carboxylate, an amide, a carboxylate(amino), or an aminocarboxylate group or a —N—O—SO$_2$— linker; and $R_2$ and $R_3$ are independently each a carboxylate, an amide, or a nitro group.

2. The method of claim 1, wherein the compound is:

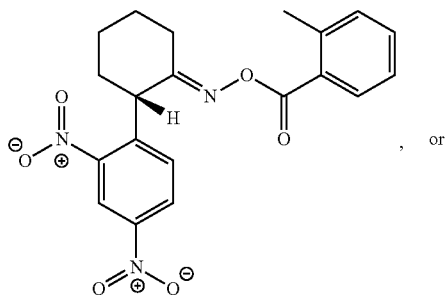, or

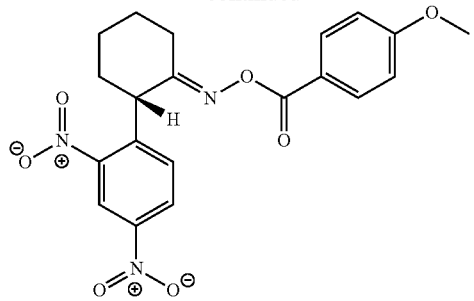

3. The method of claim 1 wherein each aryl ring is a cyclic aromatic hydrocarbon that does not contain heteroatoms.

4. The method of claim 1 wherein the alkyl groups each have from 1 to about 20 carbon atoms.

5. The method of claim 1 the Ring B group is a $C_1$ to $C_8$ cycloalkyl, or a $C_1$ to $C_6$ cycloalkyl.

6. The method of claim 1 wherein, the X group is a three to four atom linker, where atoms can include one or more carbon, oxygen, and nitrogen atoms, and where the carbon and/or nitrogen atoms can be substituted with an alkyl or an oxy group.

7. The method of claim 1 wherein X is a $C_1$ to $C_4$ alkyl linker comprising a carbonyl, a carboxylate, an amide, a carboxylate(amino), or an aminocarboxylate group.

8. The method of claim 1 wherein, the X group is a three-atom linker, with one carbon, one oxygen, and one nitrogen atom.

9. The method of claim 1 wherein, the X group comprises a carbonyl.

10. The method of claim 1 wherein, the $R_2$ and $R_3$ groups are independently a carboxylate, or a nitro group.

11. The method of claim 1 wherein, the inhibitor is the compound shown below:

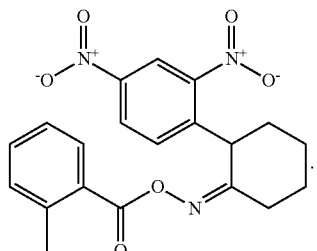

* * * * *